United States Patent [19]

Iacobucci et al.

[11] Patent Number: 5,350,681
[45] Date of Patent: * Sep. 27, 1994

[54] ENZYMATIC MEMBRANE METHOD FOR THE SYNTHESIS AND SEPARATION OF PEPTIDES

[75] Inventors: Guillermo A. Iacobucci, Atlanta, Ga.; Daniel J. Brose, Bend, Oreg.; Roderick J. Ray, Bend, Oreg.; Paul van Eikeren, Bend, Oreg.

[73] Assignee: The Coca-Cola Company, Atlanta, Ga.

[ * ] Notice: The portion of the term of this patent subsequent to Mar. 26, 2008 has been disclaimed.

[21] Appl. No.: 928,673

[22] Filed: Aug. 12, 1992

Related U.S. Application Data

[63] Continuation of Ser. No. 342,402, Apr. 24, 1989, abandoned, which is a continuation-in-part of Ser. No. 897,679, Aug. 18, 1986, Pat. No. 5,037,741, and a continuation-in-part of Ser. No. 78,504, Jul. 28, 1987, Pat. No. 5,002,871.

[51] Int. Cl.$^5$ .............................. C12P 21/00
[52] U.S. Cl. .................. 435/68.1; 435/70.1; 435/71.1; 435/41; 435/175; 435/182; 435/185; 435/284; 435/285; 435/286; 435/288; 435/280; 422/149; 422/236; 422/238; 530/344; 530/801; 560/38; 560/40; 560/41
[58] Field of Search ......... 435/68.1, 70.1, 71.1, 435/41, 175, 182, 185, 285, 286, 284, 280, 288; 422/149, 236, 238; 530/344, 801; 560/38, 40, 41

[56] References Cited

U.S. PATENT DOCUMENTS

| | | | |
|---|---|---|---|
| 3,625,734 | 12/1971 | Ward, III | 117/46 |
| 3,779,907 | 12/1973 | Li et al. | 210/22 |
| 3,813,317 | 3/1972 | Benoiton et al. | 435/280 |

(List continued on next page.)

FOREIGN PATENT DOCUMENTS

| | | |
|---|---|---|
| 0017485 | 10/1980 | European Pat. Off. . |
| 75160 | 3/1983 | European Pat. Off. . |
| 0121265 | 10/1984 | European Pat. Off. . |
| 0124313 | 11/1984 | European Pat. Off. . |
| 0149594 | 7/1985 | European Pat. Off. . |
| 0188342 | 7/1986 | European Pat. Off. . |
| 902474 | 5/1983 | France . |
| WO88/01298 | 2/1988 | PCT Int'l Appl. . |
| 2047564A | 3/1979 | United Kingdom . |

OTHER PUBLICATIONS

Liquid–Membrane Hollow Fiber Enzyme Reactors, Enzyme Engineering, vol. 3, pp. 19–28, (1978), Lo, et al.
Two Phase Biocatalytic Reaction, J. Chem. Tech. Biotechnol., vol. 32, 162–169, (1989), Lilly.

(List continued on next page.)

*Primary Examiner*—Shailendra Kumar
*Attorney, Agent, or Firm*—Kenyon & Kenyon

[57] ABSTRACT

The present invention discloses a method for the enzymatic synthesis of a peptide. A protected peptide having a C-terminal carboxylate group or a protected, N-acyl amino acid having an alpha carboxylate group is reacted with a protected peptide having an N-terminal ammonium group or a protected amino acid having an alpha ammonium group in the presence of a condensation enzyme under conditions in which the carboxylate group and the ammonium group condense to form a protected, uncharged, peptide product. This peptide product is transported across a water-immiscible hydrophobic phase into an aqueous product phase and prevented from back diffusing across the water-immiscible hydrophobic phase. The peptide product can be converted, chemically or enzymatically, to a charged species that cannot back diffuse across the water-immiscible phase into the aqueous reaction phase. The water-immiscible hydrophobic phase is an ion rejection membrane separating the aqueous reaction phase from the product phase creating oil/water interfaces with each of the aqueous phases.

32 Claims, 27 Drawing Sheets

U.S. PATENT DOCUMENTS

| | | | |
|---|---|---|---|
| 3,933,781 | 1/1976 | Bachman | 260/112.5 |
| 4,119,408 | 10/1978 | Matson | 422/177 |
| 4,119,493 | 10/1978 | Isowa | 435/68.1 |
| 4,187,086 | 2/1980 | Walmet et al. | 55/16 |
| 4,251,631 | 2/1981 | Simon | 435/106 |
| 4,455,210 | 9/1984 | Coker et al. | 204/283 |
| 4,622,417 | 11/1986 | Barnett et al. | 530/801 X |
| 4,670,151 | 6/1987 | Bitter | 210/648 X |
| 4,743,547 | 5/1988 | Kitamura et al. | 435/108 |
| 4,786,597 | 11/1988 | Matson et al. | 435/41 |
| 4,921,612 | 5/1990 | Sirkar | 435/182 X |
| 4,956,289 | 9/1990 | Wiasidlo et al. | 435/182 X |
| 5,002,871 | 3/1991 | Iacobucci | 435/68.1 |
| 5,037,741 | 8/1991 | Iacobucci | 435/68.1 |

OTHER PUBLICATIONS

"Immobilized Lactose for Whey Hydrolysis Stability and Operating Strategy", Enzyme Engineering, vol. 4, pp. 67–76, Pitcher et al., (1978).

Coupling Separation and Enrichment to Chemical Conversion in a Membrane Reactor, Aiche Annual Meeting, Nov. 8–12, 1981, (Matson, et al.).

Peptide Synthetic Chemistry, pp. 53 to 59.

Matson, Membrane Reactors in Bioprocessing, Ann. N.Y. Acad. Sci., 469, 152 (1986).

Oyama et al., Synthesis of an Aspartame Precursor by Immobilized Thermolysin in an Organic Solvent, Journal of Organic Chemistry, vol. 46, 5241–5242 (1981).

Continuous Synthesis of N–(Benzyloxycarbonyl)–L–Aspartyl L–Phenylalanine Methyl Ester with Inmobilized Thermolysis in an Organic Solvent Biotechnology, vol. 3, 459–464, (May, 1985).

Kagaku Sosethsu, 35, 195 (1982), (Toyo Soda).

Chem. Abstracts, vol. 47, 8015g, (1953), Rabinovich, et al.

J. Biol. Chem., 1986, 221, (1970), Arvid, et al.

Can. J. Biochem., 48, 1058–1065, (1970), Purdier et al.

Use of Nα–Formyl Protected Amino Acid Esters in Enzyme–Catalyzed Peptide Synthesis, Chemical Abstracts, vol. 113, 593–596, (1990), Floersheimer.

ENZYMATIC MEMBRANE METHOD FOR THE SYNTHESIS AND SEPARATION OF PEPTIDES

CROSS REFERENCE TO RELATED APPLICATIONS

This application is a continuation of Ser. No. 07/342,402 filed Apr. 24, 1989, now abandoned, which is a continuation-in-part of Ser. No. 06/897,679 filed Aug. 18, 1986, now U.S. Pat. No. 5,037,741 and a continuation-in-part of Ser. No. 07/078,504 filed Jul. 28, 1987, now U.S. Pat. No. 5,002,871.

FIELD OF THE INVENTION

The present invention relates generally to an enzymatic method for the synthesis and separation of peptides employing a membrane permeable to uncharged peptides but impermeable to charged molecules; and, more particularly, to the simultaneous synthesis and purification of peptides, L,L-dipeptides, and its application to the preparation of L-aspartyl-L-phenylalanine methyl ester (aspartame).

BACKGROUND OF THE INVENTION

The use of proteolytic enzymes as condensation catalysts for the stereospecific coupling of two L-amino acids to yield L, L-peptides is known since the early days of protein chemistry. As early as 1938, Bergmann and Fraenkel-Conrat described the formation of the water-insoluble dipeptide Bz-Leu-Leu-NHPh by reacting Bz-Leu-OH and H-Leu-NHPh in the presence of the protein degrading enzyme papain. M. Bergmann and H. Fraenkel-Conrat, *J. Biol. Chem.* 124, 1 (1938). This reaction is possible only between those amino acids that form peptide bonds that are susceptible to cleavage by the papain or other enzyme used. Indeed, the condensing reaction's equilibrium between the amino acid reactants and peptide product is largely displaced towards the reacting amino acids. Nevertheless, the condensing reaction can be driven to completion by mass action if, e.g., the dipeptide product is poorly soluble and precipitates out of the reaction phase.

Due to the commercial importance of certain peptides and the fact that enzymes are known to catalyze peptide formation under mild conditions there has been a great deal of research done on the enzymatic synthesis of peptides particularly simple dipeptides. K. Oyama and K. Kihara, *Kagaku Sosetsu* 35, 195 (1982); K. Oyama and K. Kihara, *ChemTech.* 14, 100 (1984).

The process for enzymatic synthesis of the peptide derivative aspartame, described in U.S. Pat. No. 4,165,311, hereinafter the '311 process, involves the thermolysin-catalyzed condensation of N-carbobenzoxy-L-aspartic acid with D,L-phenylalanine methyl ester and precipitation of an intermediary complex, D-phenylalanine methyl ester salt of N-carbobenzoxy-aspartame, to drive the reaction to the peptide product side. Further processing of this intermediary complex allows for the recovery of D-phenylalanine methyl ester, that may be recycled after racemization, and of the N-carbobenzoxy-aspartame derivative which can be converted to aspartame by elimination of the N-carbobenzoxy protecting group. The '311 process must be practiced on a batch basis which is cumbersome and complicates the recovery of enzyme. Also see: K. Oyama, S. Irino, T. Harada and N. Hagi, *Ann. N.Y. Acad. Sci.* 434, 95 (1985).

The N-carbobenzoxy protecting group plays an essential role in the '311 process by: fulfilling the structural requirement imposed by the active site of thermolysin; and by contributing to the insolubility of the intermediary complex thereby increasing the yield of the reaction. Elimination of the N-carbobenzoxy protecting group from the aspartame derivative must be effected under mild conditions, e.g., catalytic hydrogenation, to prevent cleavage of the methyl ester function. Catalytic hydrogenation involves the inconvenience of handling hydrogen gas on a large scale.

Alternative approaches for driving enzymatic condensation reactions to completion have also been described in the chemical literature. For example, the use of organic solvents as reaction media has been found effective for increasing the peptide product yields; although, the concomitant decrease in enzyme stability has precluded its practice on a large scale. K. Oyama, S. Nishimura, Y. Nonaka, K. Kihara and T. Hashimoto, *J. Org. Chem.* 46, 5241 (1981); H. Ooshima, H. Mori and Y. Harano, *Biotechnology Letters* 7, 789 (1985); K. Nakanishi, T. Kamikubo and R. Matsuno, *Biotechnology* 3, 459 (1985).

In view of the above-noted difficulties in the practice of prior art methods for enzymatic synthesis of peptides, particularly, the requirements for precipitation of an intermediary complex and handling of dangerous reagents, it would be desirable to provide an improved process that avoids these difficulties and that safely provides effective yields without rapid deactivation of the enzyme catalysts.

SUMMARY AND ADVANTAGES OF THE INVENTION

The present invention provides a process for the enzymatic synthesis of peptides which provides for simultaneous synthesis and purification of the peptide product.

The present invention provides a process for the safe, economical and efficient synthesis and purification of peptides and derivatives thereof, particularly aspartame.

Another advantage of the present invention is to provide an economical process for the enzymatic synthesis of peptides that provides for the efficient use of enzyme and the means to effect the synthesis on a continuous basis.

Another advantage of the present invention is to provide a process particularly adapted to the enzymatic synthesis of aspartame and its derivatives with D, L-phenylalanine and N-protected-β-substituted-L-aspartate in substantially quantitative yield.

The present invention provides a method for the synthesis and purification of a compound, comprising the steps of coupling a first reactant with a second reactant to produce a membrane transportable, uncharged compound; transporting the transportable compound across a membrane that will not transport the reactants; and preventing the transported compound from back-diffusing across the membrane.

The present invention also provides a process for the enzymatic synthesis and purification of compounds comprising the steps of coupling a first compound, including a protonated amino group (ammonium), and a second compound, including a free carboxylate group, using a condensation enzyme in an aqueous mixture to produce an uncharged (or non-ionized) coupled compound; continuously removing the uncharged coupled compound from the aqueous mixture by diffusion across a membrane that selectively transports the uncharged coupled compound to the product side of the membrane. Preferably, the transported coupled compound is a peptide or derivative thereof that is converted to a charged (or ionized) molecule so that it does not back-diffuse across the membrane. Thus, the formation of the coupled compound product is driven in the reaction mixture because it is constantly being removed therefrom.

The present invention also provides a method for the enzymatic synthesis of peptides comprising the steps of condensing first and second amino acid compounds in an aqueous initial reaction mixture to form an uncharged compound; transporting the uncharged compound into an aqueous second reaction mixture across a membrane that will not transport substantial amounts of the amino acid compounds; and converting the transported uncharged compound to a form that cannot be retransported across the membrane to the initial reaction mixture. The transported compound, converted to a form that is not retransportable across the membrane, can be removed from the second reaction mixture. Also, small amounts of first and second amino acid compounds copermeating the membrane with the uncharged compound into the second reaction mixture can be separated from the second reaction mixture and optionally returned to the initial reaction mixture.

The present invention also provides a process for the enzymatic synthesis of aspartame and its analogs, comprising the steps of condensing a N-acyl-$\beta$-substituted-L-aspartic acid including an $\alpha$-carboxylate group with a phenylalanine lower alkyl ester including an $\alpha$-ammonium group in an aqueous reaction mixture including a condensation enzyme, to form N-acyl-L-aspartyl-($\beta$-substituted)-L-phenylalanine lower alkyl ester (i.e. 1–6 carbons), an uncharged peptide; and transporting the uncharged peptide from the aqueous reaction mixture to a product mixture across a permselective membrane. In one embodiment, for proteosynthesis done at or above pH 5, the preferred acyl group is formyl, the preferred beta substituent is methyl, the preferred lower alkyl ester is isopropyl, and the preferred condensation enzyme is thermolysin. In another embodiment, for proteosynthesis done at or below pH 4, the preferred acyl group is carbobenzoxy, the preferred beta substituent is hydrogen ($\beta$-COOH), the preferred lower alkyl ester is methyl and the preferred enzyme is pepsin. In the latter case the permeable aspartame intermediate is N-CBZ-asp-phe-OMe, where the charge of the free $\beta$-carboxylate of the aspartic acid has been suppressed by protonation in order to make the peptide permeable.

The present invention also provides a method for the enzymatic resolution of racemic alpha amino acid compounds comprising the steps of: hydrolyzing an uncharged D,L-alpha amino acid derivative carrying at least one hydrolyzable functional group attached to the chiral carbon, in an aqueous reaction mixture in the presence of a hydrolase enzyme capable of hydrolyzing a sensitive functional group, to form a charged L-amino acid compound and an uncharged D-amino acid derivative, and transporting the uncharged D-amino acid derivative from the aqueous reaction mixture across an ion rejection membrane into a product mixture. The uncharged D-amino acid derivative in the product mixture can be converted to a species that cannot back-diffuse across the membrane. The method for the enzymatic resolution of racemic alpha amino acid compounds can be practiced in combination with the peptide synthesis methods discussed above. An example of racemic alpha amino acid derivative is DL-phenylalanine methyl ester. An example of hydrolase enzyme is the esterase aminoacylase I.

The present invention also provides a method for the enzymatic synthesis of a peptide, comprising the steps of: reacting a protected, peptide first reactant having a C-terminal carboxylate group with a protected, peptide second reactant having a N-terminal ammonium group in the presence of a condensation enzyme in an aqueous reaction phase under conditions in which the C-terminal carboxylate group and the N-terminal ammonium group condense forming a protected, uncharged, peptide product; transporting the protected, uncharged, peptide product across a water-immiscible hydrophobic phase into an aqueous product phase; and preventing the protected, uncharged, peptide product in the aqueous product phase from back-diffusing across the water-immiscible hydrophobic phase.

The present invention also provides a method for the enzymatic synthesis of a peptide, comprising the steps of: reacting a protected, N-acyl amino acid first reactant having an alpha carboxylate group with a protected, peptide second reactant having a N-terminal ammonium group in the presence of a condensation enzyme in an aqueous reaction phase under conditions in which the alpha carboxylate group and the N-terminal ammonium group condense forming a protected, uncharged, peptide product; transporting the protected, uncharged, peptide product into a water-immiscible hydrophobic phase into an aqueous product phase; and preventing the protected, uncharged, peptide product from back-diffusing across the water-immiscible hydrophobic phase.

The present invention also provides a method for the enzymatic synthesis of a peptide, comprising the steps of: reacting a protected, peptide first reactant having a C-terminal carboxylate group with a protected, amino acid second reactant having an alpha ammonium group in the presence of a condensation enzyme in an aqueous reaction phase under conditions in which the C-terminal carboxylate group and the alpha ammonium group condense forming a protected, uncharged, peptide product; transporting the protected, uncharged, peptide product across a water-immiscible hydrophobic phase into an aqueous product phase; and preventing the protected, uncharged, peptide product from back-diffusing across the water-immiscible hydrophobic phase.

The present invention also provides a method for the enzymatic synthesis of a peptide, comprising the steps of: combining a protected, N-acyl amino acid first reactant having an alpha carboxylate group with a protected, amino acid second reactant having an alpha ammonium group in the presence of a condensation enzyme in an aqueous reaction phase under conditions in which the alpha carboxylate group and the alpha ammonium group condense forming a protected, uncharged, peptide product; transporting the protected, uncharged, peptide product across a water-immiscible hydrophobic phase into an aqueous product mixture; and preventing the protected, uncharged, peptide product from back-diffusing across the water-immiscible hydrophobic phase.

The peptides of the present invention comprise a plurality of amino acid residues. The peptides of the present invention include, but are not limited to dipeptides. The peptides of the present invention include but are not limited to peptides comprising from three to eight amino acid residues. An example of protected, N-acyl amino acid first reactant is N-formyl-($\beta$-methyl)-aspartic acid. Examples of protected, amino acid second reactants are L-phenylalanine methyl ester and L-phenylalanine isopropyl ester. An example of a condensing enzyme is thermolysin. Another example of a protected, peptide first reactant is N-formyl-(O-Bzl)-tyr-gly-OH. Another example of a protected, peptide second reactant is H-gly-phe-leu-OMe. Another example of a condensing enzyme is papain. Another example of a protected, peptide first reactant is N-formyl-($\beta$-methyl)-asp-phe-OH. Another example of a protected, amino acid second reactant is Ht-trp-OMe. Another example of a condensing enzyme is pepsin.

In another embodiment of the present invention N-carbobenzoxy-aspartic acid having an alpha carboxylate group is the first reactant and L-phenylalanine methyl ester having an alpha ammonium group is the second reactant. The alpha carboxylate group of the first reactant and the alpha ammonium group of the second reactant condense in the presence of pepsin in an aqueous reaction phase to form a protected, uncharged, peptide product. This product is transported across a water-immiscible hydrophobic phase and prevented from back diffusing across the same.

The present invention also provides a method for the enzymatic synthesis of a peptide, comprising the steps of: reacting N-acyl-($\beta$-substituted) aspartic acid first reactant having an alpha carboxylate group with L-phenylalanine lower alkyl ester second reactant derived from a secondary alcohol having 3 to 6 carbon atoms having an alpha ammonium group in the presence of a condensation enzyme in an aqueous reaction phase under conditions in which the alpha carboxylate group and the alpha ammonium group condense forming a protected, uncharged, peptide product; transporting the protected, uncharged, peptide product across a water-immiscible hydrophobic phase into an aqueous product phase; and preventing the protected, uncharged, peptide product from back-diffusing across the water-immiscible hydrophobic phase. The aqueous reaction phase can be maintained at a temperature range of from about 20° C. to about 65° C. An example of a N-acyl-($\beta$-substituted) aspartic acid first reactant is N-formyl-($\beta$-methyl)-aspartic acid. Another example of a L-phenylalanine lower alkyl ester second reactant is L-phenylalanine isopropyl ester. An example of the condensing enzyme is thermolysin wherein the temperature of the aqueous reaction phase is about 50° C.

In one embodiment of the present invention an ILM module is utilized comprising a plurality of microporous hollow fibers made of polymeric materials. These hollow fibers can support water-immiscible organic liquids immobilized by capillarity within the microporous walls. This immobilized water-immiscible organic liquid constitutes a hydrophobic phase that functions as an ion rejection membrane separating the aqueous reaction phase from the aqueous product phase. The aqueous reaction phase, also referred to herein as the "tube phase," is located within the lumen of hollow fibers. The aqueous product phase, also referred to herein as the "shell phase" is located in the shell spaces existing in the module between hollow fibers. Oil/water interfaces are thus created with each of the two aqueous phases. A schematic representation of this ILM module is shown in FIGS. 2, 9, 25 and 26. In a preferred ILM configuration the ends of the hollow fibers are sealed or potted in resinous material so that aqueous solution being circulated through the lumens will not mix with aqueous solution being circulated through the shell spaces. Hollow fibers made of microporous polypropylene exemplify a preferred material. While this embodiment describes the shell phase as the aqueous product phase and the tube phase as the aqueous reaction phase, alternatively, the shell phase can be the aqueous reaction phase and the tube phase can be the aqueous product phase.

Alternatively, the water-immiscible hydrophobic phase comprises an organic liquid located within the lumen defined by the walls of a hollow fiber comprising hydrophilic material. An example of the hydrophilic material is cellulose. In one embodiment of the present invention, oil/water interfaces can be created by utilizing two membrane modules comprising hydrophilic hollow fibers arranged as shown in FIGS. 17, 27 and 28. In a preferred membrane module configuration the ends of the hollow fibers are sealed or potted in a resinous material so that organic liquid being circulated through the lumens will not mix with the aqueous solution (phase) being circulated through the shell spaces. Each module comprises a plurality of hydrophilic hollow fibers. The lumens of the hydrophilic hollow fibers are filled with a water immiscible organic liquid. The two membrane modules having a connecting means such as a common loop of circulating organic liquid comprise a membrane contactor. The water-immiscible organic liquid located within the lumens of the hydrophilic hollow fibers comprises the water-immiscible hydrophobic phase of each membrane module, and the two isolated aqueous phases located outside of the walls of the hydrophilic hollow fibers respectively comprise the aqueous reaction and product phases. The water-immiscible hydrophobic phase functions as an ion rejection membrane separating the aqueous reaction phase in the first membrane module from the aqueous product phase in the second membrane module.

A membrane contactor comprises a first membrane module for transferring the protected, uncharged peptide product from the aqueous reaction into the water-immiscible hydrophobic phase; a second membrane module for transferring the protected, uncharged peptide product from the water-immiscible hydrophobic phase into the aqueous product phase; and a connecting means between the water-immiscible hydrophobic phase in the first membrane module and the water-immiscible hydrophobic phase in the second membrane module of the membrane contactor. The aqueous reaction phase in the first membrane module is located outside of the hollow fibers and wets the walls of the hollow fibers creating an oil/water interface between the aqueous reaction phase and the water-immiscible hydrophobic phase; and the aqueous product phase in the second membrane module is located outside of the hollow fibers and wets the walls of the hollow fibers creating an oil/water interface between the aqueous product phase and the water-immiscible hydrophobic phase. The circulation of liquids at the oil/water interfaces is countercurrent. The aqueous product phase may be processed repeatedly through a plurality of membrane contactors.

One example of the step of preventing the protected, uncharged, peptide product from back-diffusing across the water-immiscible hydrophobic phase comprises converting the protected, uncharged, peptide product to a charged species. The conversion can be chemical or enzymatic. Chemical means include pH dependent ionization of a prototropic functional group, ionization resulting from a dissociation of a carboxylic acid function and/or resulting from a protonation of a free amino group. An example of an enzymatic conversion is the hydrolysis of an ester function utilizing a protease having esterolytic activity. An example of the protease enzyme having esterolytic activity is aminoacylase I. The enzyme having esterolytic activity can be circulated against the membrane in the aqueous product phase. The enzyme having esterolytic activity can be immobilized on a water insoluble support and the aqueous product phase can be circulated over the enzyme.

The present invention also provides peptide compounds selected from the group consisting of N-formyl-(β-benzyl)-L-aspartyl-L-phenylalanine methyl ester, N-formyl-(β-benzyl)-L-aspartyl-L-phenylalanine, N-carbobenzoxy-(β-methyl)-L-aspartyl-L-phenylalanine methyl ester, N-carbobenzoxy-(β-methyl)-L-aspartyl-L-phenylalanine, N-formyl-(β-methyl)-aspartyl-phenylalanine methyl ester, N-formyl-(β-methyl)-aspartyl-phenylalanine, N-formyl-(β-methyl)-L-aspartyl-L-phenylalanine, N-formyl(β-methyl)-aspartyl-phenylalanyl-tryptophan methyl ester, N-formyl(β-methyl)-aspartyl-phenylalanyl-tryptophan, N-carbobenzoxy-phenylalanyl-glycyl-glycyl-phenylalanine methyl ester, N-carbobenzoxy-phenylalanyl-glycyl-glycyl-phenylalanine, N-formyl-(O-benzyl-tyrosyl)-glycyl-glycyl-phenylalanyl-leucine methyl ester, N-formyl-(O-benzyl-tyrosyl)-glycyl-glycyl-phenylalanyl leucine, N-formyl-(β-methyl)-aspartyl-phenylalanine isopropyl ester.

The present invention provides a method for the enzymatic synthesis of a peptide, comprising the steps of: reacting a first compound selected from the group consisting of a protected peptide having a C-terminal carboxylate group and a protected, N-acyl amino acid having an alpha carboxylate group with a second compound selected from the group consisting of a protected peptide having a N-terminal ammonium group and a protected amino acid having an alpha ammonium group in the presence of a condensation enzyme in an aqueous reaction phase under conditions in which the carboxylate group and ammonium group condense forming a protected, uncharged, peptide product; transporting the protected, uncharged, peptide product across a water-immiscible hydrophobic phase into an aqueous product phase; and separating the protected, uncharged, peptide product from the aqueous product mixture to prevent that product from back-diffusing across the water-immiscible hydrophobic phase.

The present invention also provides a method for the enzymatic synthesis of a peptide, comprising the steps of: reacting N-acyl-(β-substituted) aspartic acid first reactant having an alpha carboxylate group with L-phenylalanine lower alkyl ester second reactant having an alpha ammonium group in the presence of a condensation enzyme in an aqueous reaction phase under conditions in which the alpha carboxylate group and the alpha ammonium group condense forming a protected, uncharged, peptide product; transporting the protected, uncharged, peptide product across a water-immiscible hydrophobic phase into an aqueous product phase; and separating the protected, uncharged, peptide product from the aqueous product phase to prevent that product from back-diffusing across the water-immiscible hydrophobic phase. The step of separating the protected, uncharged, peptide product from the aqueous product phase may be carried out utilizing a trapping means such as reverse osmosis or the formation of specific molecular complexes. Specific cavities comprising zeolites and/or cyclodextrins may be utilized. The step of separating may also be carried out utilizing solvent extraction, adsorption on a matrix or by precipitation with a reagent. The aqueous reaction phase can be maintained at a temperature in a range of from about 20° C. to about 65° C. An example of the phenylalanine reactant is a lower alkyl ester derived from a secondary alcohol having 3 to 6 carbon atoms. An example of the condensing enzyme is thermolysin wherein the temperature of the aqueous reaction phase is about 50° C. An example of the aspartic acid N-acyl-(β-substituted) first reactant is N-formyl-(β-methyl)-asp-OH. An example of the phenylalanine lower alkyl ester second reactant is L-phenylalanine isopropyl ester.

In general, the amino acids which can be utilized for peptide synthesis according to the present invention comprise the L-enantiomers of the 20 natural amino acids recognized by the genetic code as protein building blocks, plus their various protected derivatives available through standard procedures commonly used in the field of peptide synthesis. The preferred protecting groups will vary according with the choice of condensing enzyme, nature of the hydrophobic phase, pH, temperature and nature of the solvent for any particular proteosynthesis.

BRIEF DESCRIPTION OF THE DRAWINGS

The foregoing and other objects and advantages are attained by the invention, as will be apparent from the following detailed description taken in conjunction with the accompanying drawings, wherein.

DETAILED DESCRIPTION OF THE INVENTION

The invention disclosed herein provides a procedure for driving to completion the enzymatic synthesis of peptides in an aqueous reaction mixture at equilibrium, by separating the uncharged peptide intermediate, or derivative thereof, from the reaction mixture by means of a membrane that selectively transports the uncharged peptide out of the reaction mixture into a product mixture. Because the membrane is substantially impermeable to the reactants (charged molecules) removal of the peptide intermediate from the reaction mixture causes a decrease of peptide concentration at equilibrium that pushes the reaction toward completion by mass action.

Figure 25:
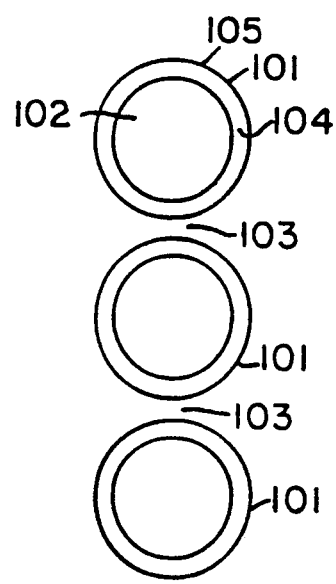
FIG. 25 is a partial view (enlarged) of a cross section of hollow fibers in an ILM module.

The membranes most useful in the practice of the present invention are Immobilized Liquid Membranes (ILM) comprising a nonpolar liquid embedded in microporous support material providing an oil-water interface that is substantially impervious to the enzymes, reactants and other charged products. Hydrophobic polymers such as polypropylene are preferred support materials. ILM modules can be produced utilizing polypropylene hollow fibers. Celgard, a registered trademark of the Celanese Corporation, 1211 Avenue of the Americas, New York, N.Y. 10036 and sold by Celanese Fibers Marketing Corporation, Charlotte, N.C., is an example of commercially available hollow fibers comprising polypropylene. Potting compounds known in tile art and polyvinyl chloride pipe or tubing may optionally be utilized in fabricating an ILM module. Another polymer for fabricating the microporous support material is TEFLON, a trademark of E. I. DuPont de Nemours & Co. for fluorinated hydrocarbon polymers. A typical microporous support is GORE-TEX, a trademark of W. C. Gore & Associates, Inc. FIG. 25 is a partial view (enlarged) of a cross section of hollow fibers in an ILM module. The partial view which is enlarged shows hydrophobic hollow fibers 101 having a lumen (bore) 102, made from microporous polymeric material 105 which can support water-immiscible organic liquid by capillarity within microporous walls. A capillary 104 is shown in the microporous polymeric material 105; however, the microporous polymeric material 105 actually includes many such capillaries 104 extending from the lumen to the exterior of the hollow fiber 101. The lumen 102 comprises the tube phase (e.g., aqueous reaction phase). The space 103 between hollow fibers comprises the shell phase (e.g., aqueous product phase).

Figure 26:
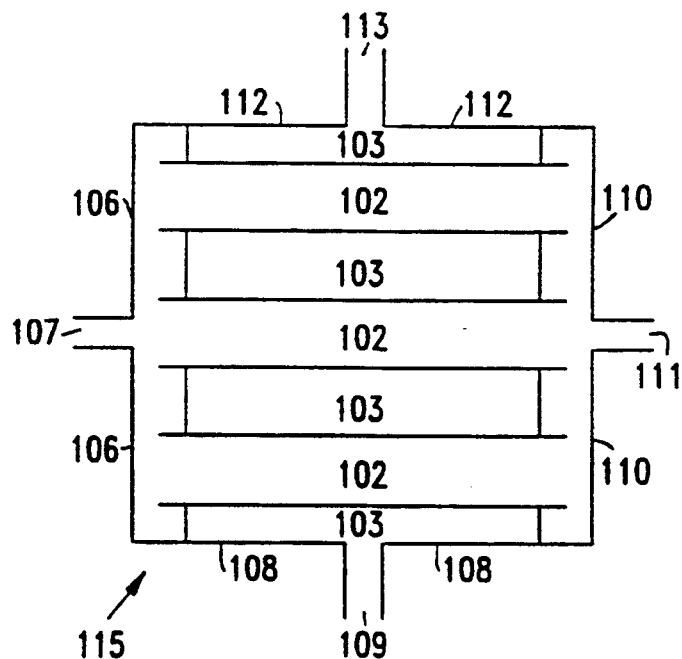
FIG. 26 is a partial schematic view (enlarged) of an ILM module.

FIG. 26 is partial schematic view (enlarged) of an an ILM module 115. The partial view which is enlarged shows hydrophobic hollow fibers 101. The ends of each hollow fiber are potted in a resinous material (potting compound) so that the tube phase being circulated through the lumen 102 through opening 107 on first wall 106 and returned through opening 111 on third wall 110 will not mix with the shell phase being circulated through space 103, through opening 109 on second wall 108 and returned through opening 113 on fourth wall 112. In ILM module 115 actually comprises many hydrophilic hollow fibers 101 although only three are shown in this figure.

The micropores pass through the support material and should be sized so that an immobilized liquid will be held therein by capillarity and will not escape therefrom when subjected to, e.g., pressure differentials across the membrane or other ordinary reaction conditions. Subject to the foregoing limitations is advantageous to maximize the contact area between the immobilized liquid and reaction mixture to maximize the rate of transfer (flux) of the uncharged peptide product across the membrane. It will be appreciated that the preferred pore size will vary depending on the properties of the particular immobilized liquid, reactants employed, products produced, and like factors; and further, that the optimum pore size can be determined empirically by those skilled in the art. A useful discussion of pore size selection is found in U.S. Pat. No. 4,174,374 the text of which is incorporated herein by reference. The use and preparation of immobilized liquid membranes are described in the following references, texts of which are also incorporated herein by reference, S. L. Matson, J. A. Quinn, *Coupling Separation and Enrichment to Chemical Conversion in a Membrane Reactor*, paper presented at the AICHE Annual Meeting, New Orleans La. (Nov. 8–12, 1981) and S. L. Matson and J. A. Quinn, *Membrane Reactors in Bioprocessing*, Ann, N.Y. Acad, Sci, 469, 152 (1986), The immobilized liquid held in the microporous support by capillarity should be water immiscible and a good solvent for the uncharged peptide product which must be transported across the membrane (diffused) at a reasonable rate, i.e., good transport characteristics/high flux; while, charged or ionized molecules on both the reaction side and product side of the membrane are, for the most part, not transported across the membrane in either direction, i.e., good selectivity/ion rejection.

Selection of the best combination of support material and immobilized liquid for use in an enzymatic synthesis of a peptide in accordance with the present invention will depend, in part, on the nature of the particular reactants employed, products desired and solvents in the system.

The generally preferred immobilized liquids for the practice of the present invention include water-immiscible organic solvents, such as alcohols of 6 to 20 carbons, branched and unbranched, for example, n-decanol, n-dodecanol, iso-hexadecanol and mixtures thereof. Also preferred are mixtures of water immiscible organic solvents including mixtures thereof. Such solvents include but are not limited to N,N-diethyl-dodecanamide, dodecane and 2-undecanone.

Another type of membrane useful in the practice of the invention comprises hydrophobic solid films made of organic polymers such as polyvinyl chloride or the like. The preparation of these polymer membranes is well described in the literature, for example, O. J. Sweeting, Editor, *Science and Technology of Polymer Films,* Interscience, New York (1968), while extensive application of such membranes to the separation of gases and liquids are discussed in S. T. Hwang and K. Kammermeyer, *Membranes in Separations, Techniques of Chemistry,* Vol. VII, (A. Weissberger, editor) John Wiley & Sons, Inc., New York (1975).

A preferred embodiment of the invention employs a membrane reactor/separator system which provides an aqueous reaction mixture or phase circulating in contact with one side of an ILM membrane and a product aqueous phase or mixture circulating countercurrently at the opposite surface of the membrane. S. L. Matson and J. A. Quinn, *Ann. N.Y. Acad. Sci.* 469, 152 (1986). The pH and temperature of the reaction and product phases are maintained at a value that keeps the reactants in a form that minimizes their transport across the membrane at pH's between about 4.0 and 9.0. Transport of the uncharged peptide intermediate from the reaction phase to the product phase is driven by the concentration gradient across the membrane created by increasing uncharged peptide concentration in the reaction phase. The transport activity or flux across the membrane can be significantly enhanced by the simultaneous, irreversible conversion of the transported peptide, in the product phase, to a species that cannot back-diffuse. For example, the latter conversion may result in the formation of a polar peptide that cannot back-diffuse and thus generating the driving force needed to achieve completion of the coupling reaction. An example of a membrane reactor/separator that could be adapted for the practice of the present invention is found in U.S. Pat. No. 4,187,086.

Available alternative membrane reactor/separator configurations that could be adapted to practice of the present invention include the hollow fiber modules described in U.K. Patent Application 2,047,564 A, and conventional plate and frame-type filter devices well known in the art.

In addition to selective transport of the uncharged peptide the membrane provides a barrier between the reaction phase and product phase that prevents undesirable mixing of, and reactions between, the components of each phase.

In a preferred membrane reactor/separator configured in accordance with the present invention, the chemical equilibrium between the reactants is actually "pulled" across the membrane by conducting an irreversible conversion of the transported uncharged peptide, to a membrane impermeable species, on the product side of the membrane, This type of membrane reactor/separator employs a coupled two enzyme ($E^1$ and $E^2$) process of the general type:

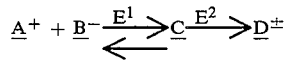

The charged reactants A and B are amino acids and/or small peptides which are condensed with the aid of peptide forming enzyme $E^1$ to form the uncharged intermediary peptide C which is selectively transported across the membrane to the product side. It is understood that reactive functional groups in the reactants that do not participate in the desired reaction may be protected or blocked, where necessary, to prevent undesirable side reactions and/or charges in the products. On the product side of the membrane uncharged peptide C is converted to charged peptide D which cannot back-diffuse across the membrane, causing the chemical equilibrium in the reaction mixture to shift toward the production of more C.

Figure 1:
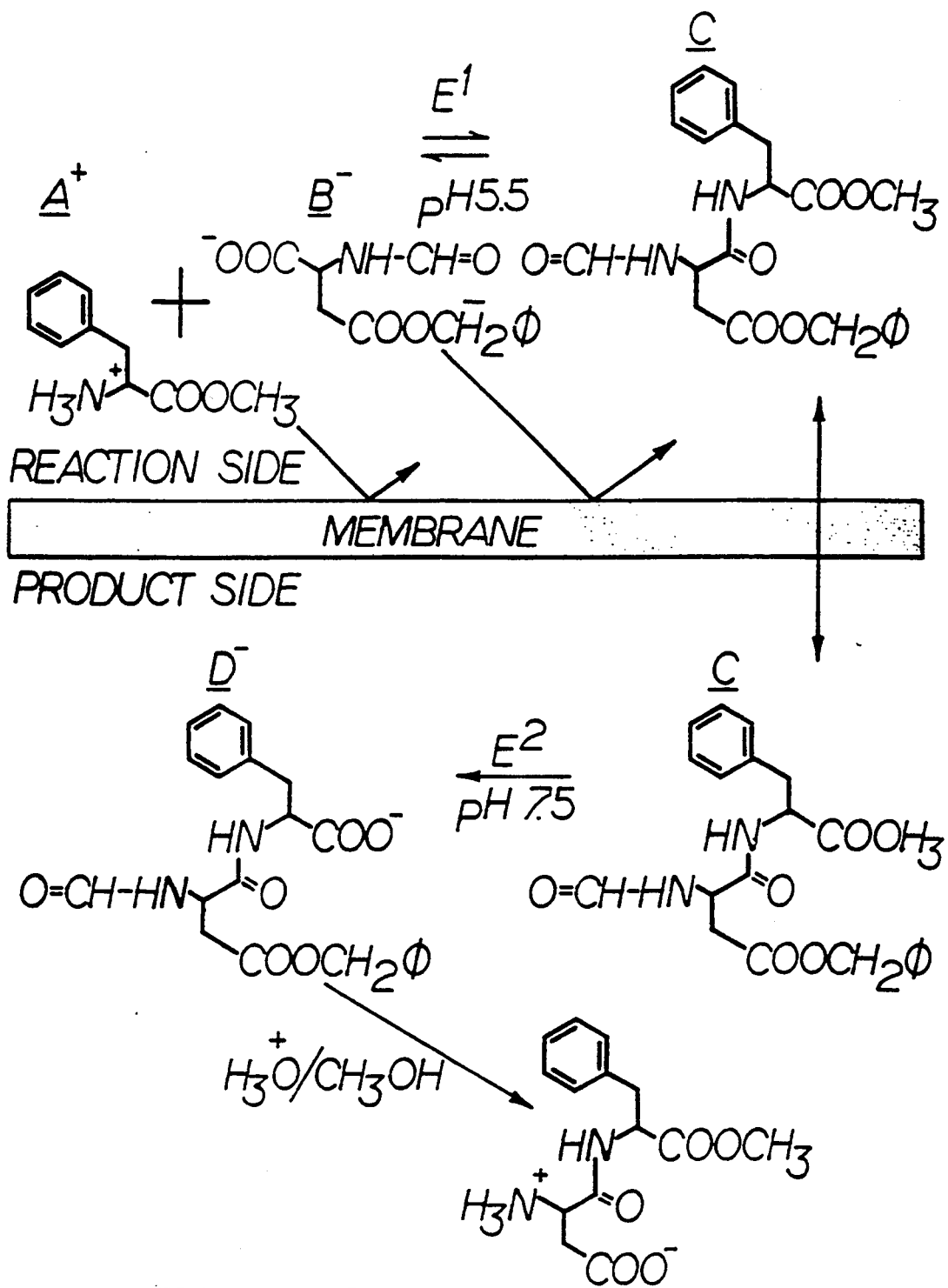
FIG. 1 is schematic illustration of the enzymatic synthesis of aspartame in accordance with the present invention.

This concept is illustrated in FIG. 1, for the specific case of the enzymatic condensation of D,L-phenylalanine methyl ester with (N- and β-protected) N-formyl-β-benzyl-L-aspartate, in the presence of thermolysin at about pH 5.5.

In the reaction scheme illustrated in FIG. 1 the reactant $A^+$ is D, L-phenylalanine methyl ester and $B^-$ is N-formyl-β-benzyl-L-aspartate. The reactants are condensed on the reaction side of the membrane by the enzyme $E^1$thermolysin forming the uncharged peptide C. The pH is selected to maintain the reactants in their charged state and thus minimize their diffusion across the membrane along with uncharged peptide C.

Although the chemical equilibrium for the condensation reaction largely favors the reactant $A^+$ and $B^-$ species, diffusion of the uncharged peptide product C across the membrane to the product side requires the constant production of C to maintain the chemical equilibrium on the reaction side of the membrane.

In one embodiment, on the product side of the membrane an esterase enzyme $E^2$ quickly and irreversibly converts the uncharged peptide C diffused across the membrane to charged peptide D which cannot back-diffuse to the reaction side. Thus the chemical equilibrium on the reaction side is effectively "pulled" across the membrane and toward the production of uncharged product C. Thereafter, the peptide D is converted to aspartame by acid hydrolysis, which removes the formyl and benzyl protecting groups, followed by C-terminal esterification with methanol. In another embodiment the esterase is not utilized and the uncharged product C is directly separated from the product mixture by physical means.

Figure 2:
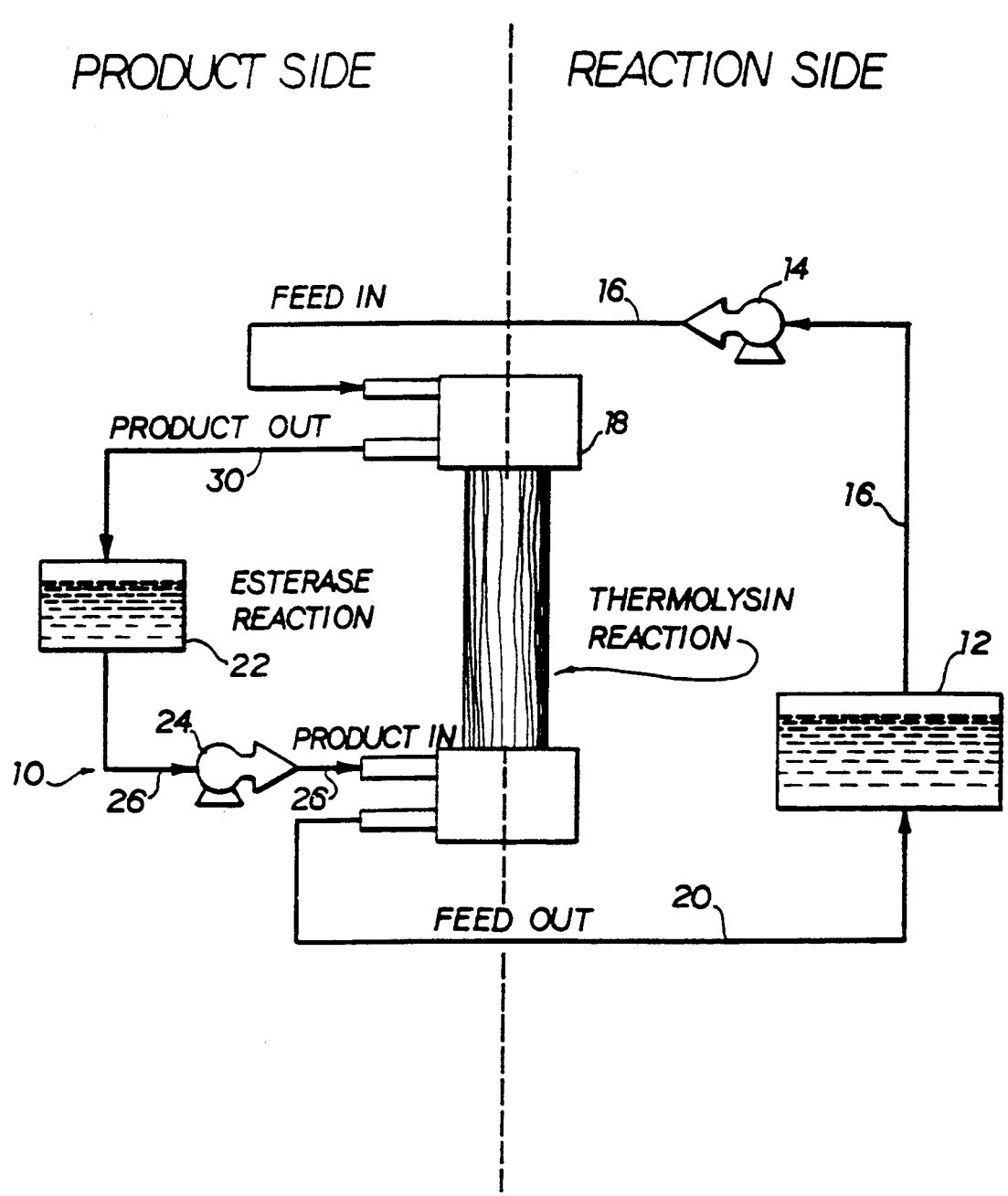
FIG. 2 is a schematic representation of an apparatus for practicing the process of the present invention.

The foregoing method may be practiced in a countercurrent flow membrane reactor/separator 10, as shown in FIG. 2, operating under controlled conditions of pH and temperature, so that a reaction mixture comprising a N-acyl-β-substituted-L-aspartic acid, e.g., N-formyl-β-benzyl-L-aspartate, having a free α-carboxylate group (electronegative species) which is allowed to condense with a reactant, e.g, D, L-phenylalanine methyl ester, having a protonated free α-amino group (electropositive species), under the catalytic action of proteases active in the pH range of about 4.0–9.0, to yield a fully protected L-aspartyl-L-phenylalanine dipeptide bearing no ionized groups (electroneutral species). On the reaction side of the membrane, the reaction mixture is circulated from reactor tank 12 aided by pump 14, through feed-in conduit 16 through separator 18 to feed-out conduit 20 which returns to reactor tank 12. On the product side of the membrane a product mixture or sweep including fully protected uncharged peptide, e.g., N-formyl-β-benzyl-L-aspartyl-L-phenylalanine methyl ester transported across the membrane, is circulated from product reactor tank 22, aided by pump 24, through product sweep in-conduit 26, through the product side of separator 18, to product sweep out-conduit 30. This product mixture in product reactor tank 22 includes a second enzyme E², an esterase or other suitable reagent, that can cleave at least one of the protected groups borne by the uncharged peptide, thus generating an electrocharged species that cannot escape the sweep stream by back-diffusing through the membrane. If an esterase is utilized, a preferred esterase will have a preferred pH range of from about 6.0 to 9.0. Aminoacylase I, α-chymotrypsin and subtilisin A are examples of esterases considered useful in the present invention.

The conversion to charged species that cannot back diffuse across the water-immiscible hydrophobic phase can be carried out utilizing chemical or enzymatic means. Chemical means include pH dependent ionization of a prototropic functional group, ionization resulting from dissociation of a carboxylic acid function and/or resulting from a protonation of a free amino group or hydrolysis of an ester function. For example, the conversion of an uncharged product into a charged product that cannot back-diffuse can be achieved by an appropriate pH gradient between the two aqueous phases separated by the hydrophobic membrane. This is physically possible as the hydrophobic phase is impervious to ions, thus allowing the existence of two aqueous phases of different pH in equilibrium with respect to non-ionic solutes. For example, a diffusible free amine R-NH₂, bearing no charges in an aqueous phase at pH 8, can be transferred across a hydrophobic membrane into a second aqueous phase at pH 3 and be irreversibly trapped by protonation to form the non-diffusible ammonium salt $$R-\overset{+}{N}H_3.$$

Similarly, a diffusible acid R-COOH bearing no charges at pH 2 can be transferred at pH 2 and trapped at pH 6 through dissociation to the non-diffusible carboxylate R-COO⁻. The utilization of a pH gradient is particularly useful in the synthesis and separation of peptides and other similar compounds bearing carboxyl and ammonium groups.

Figure 17:
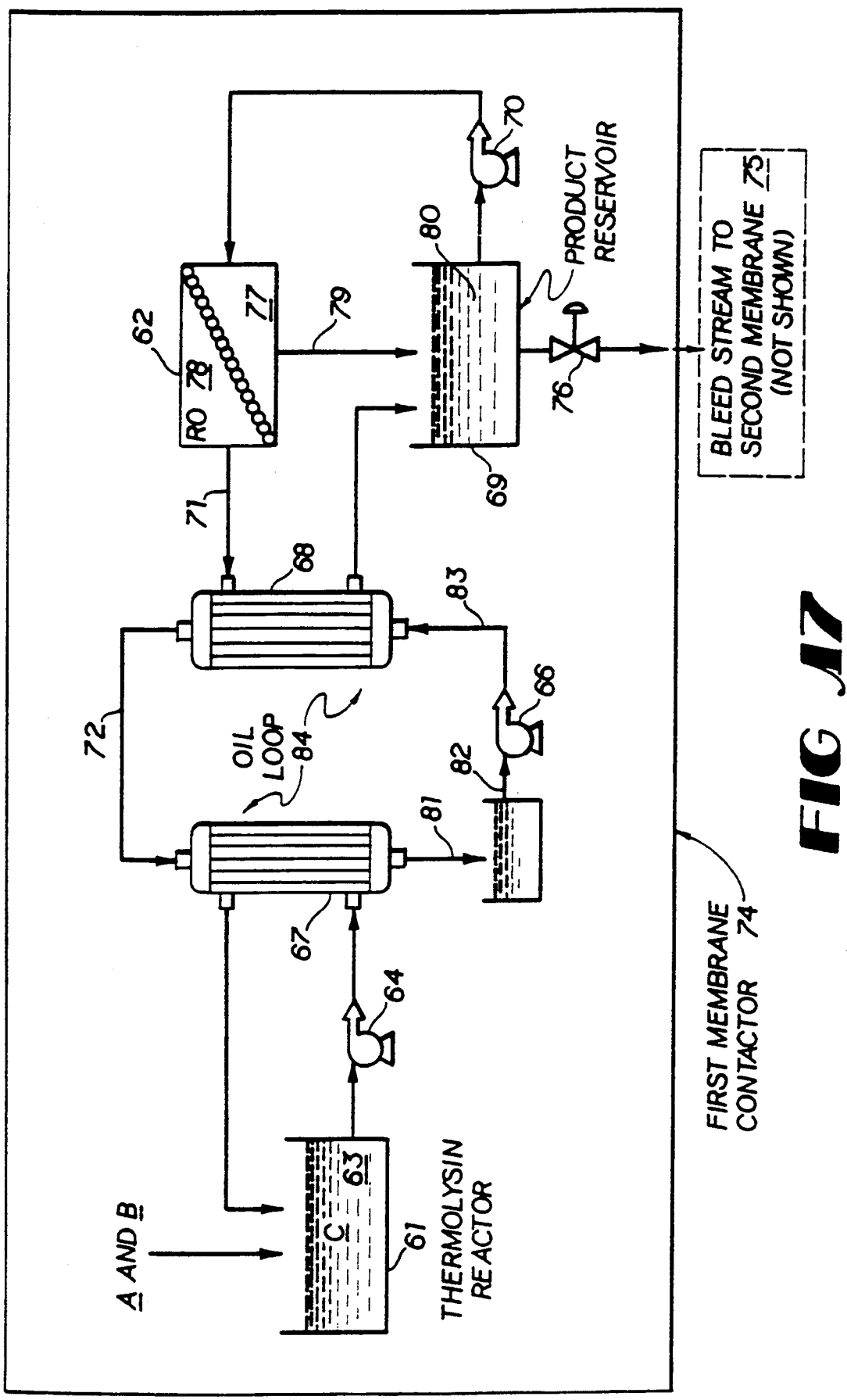
FIG. 17 describes the process in which RO is used to trap product on one side of the membrane contactor.

A similar way of practicing this invention but using a different liquid membrane configuration is illustrated in FIG. 17. The liquid membrane configuration of FIG. 17 is preferred under conditions wherein the water-immiscible hydrophobic phase may leak as a result of higher reacting temperatures such as temperatures above 40° C. In this oil/water contactor the organic membrane is created at the inner walls of hydrophilic cellulose fibers, whose bores or lumens are filled with the desired hydrophobic organic phase, and having the bulk aqueous phase located outside of the fibers and wetting the walls of said fibers. Packing of bundles of said fibers in a modular arrangement allows for the creation of two compartments, separated by an oil/water interface. Circulation of said oil phase between two separated aqueous phases contained in two individual modules constituting a single contactor is shown in FIG. 17. A plurality of contactors may be utilized. Each aqueous phase representing the reaction and product phases discussed above, allows for the transport of permeable product from one aqueous phase to the second one containing the esterase enzyme. Membrane separators of the general type shown in FIG. 17 are well known in the art. U.S. Pat. No. 4,754,089 describes the utilization of such membranes in phase transfer catalysis. U.S. Pat. No. 4,778,688 describes a similar membrane. U.S. Pat. Nos. 4,572,824, 4,563,337 and 4,443,414 also describe such oil water contactors. Another example of similar membranes is described in U.S. Pat. No. 4,664,808. Membrane variations in multiphase assymetric reactor systems are described in U.S. Pat. No. 4,795,704.

The charged product may be periodically discharged and/or continuously removed from the product phase by conventional separation means such as ion exchange resins and other techniques including reverse osmosis and the like, and the remaining effluent may be recycled through the system. Where this separation is by ion-exchange the resulting product bound to the ion-exchange resin may be desorbed and recovered using conventional procedures.

In the case of reverse osmosis separation, it may be first necessary to retain the esterase enzyme utilizing an ultrafiltration membrane of adequate porosity that will produce an ultrafiltrate containing only the charged product. This ultrafiltrate can then be concentrated over a reverse osmosis membrane and the charged product isolated from the resulting retentate.

Alternatively, in another embodiment the uncharged peptide can be prevented from back-diffusing across the membrane utilizing a trapping such as a reverse osmosis membrane. In this case the second enzyme may not be required to efficiently operate the process. Reverse osmosis is well-known in the art. James S. Johnson, Jr., "Reverse Osmosis," in Kirk-Othmer's Encyclopedia of Chemical Technology, Third Edition, Vol. 20, pp. 230-248 John Wiley & Sons, New York, N.Y. (1984) and U.S. Pat. No. 4,643,902.

Other trapping means include the formation of specific molecular complexes. Specific cavities of zeolites and/or cyclodextrins may be utilized. In addition to trapping, solvent extraction, adsorption on a matrix or precipitation with a reagent may be utilized for the step of separating the protected, uncharged, peptide product from the aqueous product phase. The use of membrane contactors in conjunction with reverse osmosis, as described in Examples 14 and 17, will cause the desired displacement of the proteosynthetic equilibrium without affecting the kinetics of peptide synthesis in the enzyme reactor. This approach is considered as a viable alternative to the use of a second enzyme for the purpose of driving the proteosynthesis to completion. Its usefulness, however, is dictated in practice by the relative affinity of the uncharged peptide intermediate towards the oil/water phase. The higher the partition towards the oil phase is, the lower the permeability of the peptide towards the aqueous product phase will become, making the transfer from oil to water the rate-limiting step of the process. This phenomenon is illustrated in Example 16, and FIG. 21, where the rate of release of the peptide N-formyl-(β-methyl)-asp-phe-O-< from the oil phase into the aqueous product phase, called here $V_{perm}$, is increased by a factor of two when the aqueous phase contains the enzyme aminoacylase able to convert that peptide into the more hydrophilic N-formyl-($\beta$-methyl)-asp-phe-OH.

The selection of appropriate deprotection reagent(s) is determined by the chemical nature of the protecting groups used on the reactants, such as, N-protected-L-aspartic acid, and as indicated above the choice of protecting groups is in turn dictated by structural constraints imposed by the active site of the condensing enzyme.

In general, the condensing enzymes useful in the practice of the present invention are proteolytic enzymes, sometimes called proteases, which may be divided into two groups. The more commonly used are endopeptidases, which only cleave inner linkages, and exopeptidases, which preferably cleave terminal linkages. Useful enzymes include serine proteinases, (EC 3.4.21) such as chymotrypsin, trypsin, subtilisin BNP' and Achromobacter protease; thiol proteinases (EC 3.4.22), such as, papain; carboxyl proteinases (EC 3.4.23), such as, pepsin; and metalloproteinases (EC 3.4.24), such as, thermolysin, prolisin, Tacynasen N (*St. caespitosus*) and Dispase. Binding of the enzymes to insoluble supports, following procedures well known to practitioners of the art, may be incorporated to the practice of this invention; and although binding the enzymes is not an essential step, it may be desirable in certain applications. Among the many proteases potentially useful for the practice of this invention, thermolysin [E.C. 3.4.24] is the condensing enzyme most preferred because of its remarkable thermostability, wide availability, low cost and broad useful pH range between about 5.0 to 9.0. Other preferred proteases include pepsin and penicillopepsin [T. Hofmann and, R. Shaw, *Biochim. Biophys. Acta* 92 543 (1964)] and, the thermostable protease from *Penicillium duponti* [S. Emi, D. V. Myers and G. A. Iacobucci, *Biochemistry* 15, 842 (1976)]. They would be expected to function at about pH 4.5 or below, exhibit good stability at such pHs, and do not require the presence of $Zn^{++}$ and $Ca^{++}$ ions to maintain their activity.

The practical realization of enantiomeric selectivity that is, in the case described above, production of only the L,L isomer of the peptide C, is directly related to the enzyme selected, optimal functioning of the membrane, chemical nature of the support material and pH of the aqueous reaction phase.

One preferred membrane for practicing the above-described specific method is a microporous polypropylene support material including a mixture of iso-hexadecanol and n-dodecane immobilized therein. This membrane is available from Bend Research, Inc., 64550 Research Road, Bend, Oreg. 97701, U.S.A. under the tradename/designation "Type 1 Hollow Fiber Selective Dialysis Membrane" and is preferred with the reactions of Examples 1–4. Another preferred membrane utilizes Celgard Type 2400 polypropylene hollow fibers (Celgard is a registered trademark of the Celanese Corporation, 1211 Avenue of the Americas, New York, N.Y. 10036. Celgard can be obtained from Celanese Fibers Marketing Corporation, Charlotte, N.C.) as the microporous material supporting a mixture of 30% v/v N,N-diethyl-dodecanamide in dodecane as the water-immiscible organic liquid ILM. This membrane was obtained from Bend Research, Inc., 64550 Research Road, Bend, Oreg. 97701, U.S.A. under the tradename/designation "Type 2 Hollow Fiber Selective Dialysis Membrane" and is preferred with the reactions of Examples 5–9. Celgard Type 2400 polypropylene hollow fibers having a pore size of 0.025–0.050 $\mu$m and a wall thickness of 25 $\mu$m were utilized in the Type 2 Hollow Fiber Selective Dialysis Membrane of Bend Research, Inc. When operated at pHs of about 5.5, these membranes exhibit a high selectivity, for example, when practicing the process of FIG. 1, selectivity in the range of about 500:1 (w/w) in favor of the uncharged peptide species have been measured. That is, 500 milligrams of the uncharged peptide (C) are transported across the membrane for each milligram of charged reactant $A^+$ or $B^-$ transported.

As mentioned above, for the application of the present invention it will be necessary, or desirable, to block or protect various functional groups on the reactants and products to prevent undesirable side reactions that could prevent production of the desired product and/or reduce its yield and to suppress electrocharges in intermediate peptide C. Table I below lists a series of selected combinations of protecting groups and deprotection conditions useful in connection with the practice of this invention.

TABLE I

| PROTECTING GROUPS AND DEPROTECTION REAGENTS USEFUL IN THE SYNTHESIS OF ASPARTAME (APM). | | | | |
|---|---|---|---|---|
| $R^1$ | $R^2$ | $R^3$ | Group Removed/Reagent | Product |
| $\emptyset CH_2O-$ | $\emptyset CH_2OCO-$ | $CH_3O-$ | $R^1,R^2/(Pd)H_2$ | APM |
| $\emptyset CH_2O-$ | $-CH=O$ | $CH_3O-$ | $R^2/H_3O^+$ | $\beta$-benzyl-APM |
| $\emptyset CH_2O-$ | $-CH=O$ | $CH_2O-$ | $R^3$/Fungal esterase | N-formyl-$\beta$-benzyl-L-aspartyl-L-phenylalanine |
| ter-BuO | $-CH=O$ | $CH_3O-$ | $R^1,R^2/H_3O^+$ | APM |
| $CH_3O-$ | $-CH=O$ | $CH_3O-$ | $R^3$/fungal esterase | N-formyl-isoAPM |
| $CH_3O-$ | $-CH=O$ | i-Pro$-$O$-$ | $R^3$/fungal esterase | N-formyl-isoAPM |
| $CH_3O-$ | $-CH=O$ | $CH_3O-$ | $R^3/\alpha$-chymotrypsin | N-formyl-isoAPM |

TABLE I-continued
PROTECTING GROUPS AND DEPROTECTION REAGENTS USEFUL IN THE SYNTHESIS OF ASPARTAME (APM).

| R¹ | R² | R³ | Group Removed/Reagent | Product |
|---|---|---|---|---|
| $NH_2-$ | $\phi CH_2OCO-$ | $CH_3O-$ | R¹/asparaginase | N—CBZ—APM |
| L-dihydroorotyl-L-phenylalanine methyl ester | | | R¹,R²/hydantoinase | APM |
| H | $\phi CH_2OCO-$ | $CH_3O-$ | R¹/OH⁻ | N—CBZ—APM |
| $CH_3O-$ | $\phi CH_2OCO-$ | $CH_3O-$ | R³/fungal esterase | N—CBZ-iso APM |
| $CH_3O-$ | $\phi CH_2CO-$ | $CH_3O-$ | R²/penicillin acylase | APM-β-methylester |

As a result of the enantioselectivity of selected condensation enzymes and the functional discrimination exerted by the membrane, the practice of the invention using N-formyl-L-aspartyl-β-benzyl ester and D,L-phenylalanine methyl ester could achieve a 99.8% enantiomeric resolution of the racemic phenylalanine methyl ester reactant, the L-enantiomer appearing as N-formyl-L-aspartyl(β-benzyl)-L-phenylalanine methyl ester, an aspartame derivative, with the unreacted D-enantiomer remaining in the reaction phase.

The D-phenylalanine methyl ester remaining in the reaction phase may be recovered therefrom, re-racemized to the D,L-stage, and recycled into the feedstock. Racemization is a necessary step for processes employing racemic amino acid reactants, e.g., the '311 process described above.

The economic advantages of the present invention derive, at least in part, from the use of a racemate feed reactant rather than a more expensive pre-resolved L-enantiomer. This advantage is made possible by the in situ optical resolution of the D,L-phenylalanine methyl ester due to: (a) the enantioselectivity of the condensing enzyme; and (b) the high selectivity of the membrane in favor of the uncharged species.

Preferred methods for the low-cost synthesis of racemic phenylalanine are those based on the utilization of benzaldehyde via 5-benzalhydantoin sometimes called the Grace process, or the catalytic carbonylation of benzyl chloride to phenylpyruvic acid, a procedure developed by Sagami Chemical Research Center, Tokyo, Japan (sometimes referred to as the Toyo Soda process of Toyo Soda Manufacturing Co., Ltd., Yamaguchi, Japan).

It will be appreciated by those skilled in the art that the practice of this invention is not necessarily restricted to the synthesis of peptide sweeteners, such as, aspartame or its analogs and derivatives. The invention may also be used for the synthesis of other useful peptides, di-, tri-, tetra- and pentapeptides, or peptides of higher complexity, that are capable of diffusing through a permselective membrane at a reasonable rate. For example, considering the bond specificity of thermolysin, and assuming the presence of only one thermolysin sensitive bond in the product (indicated by the arrow in the formula below), one could synthesize met-enkephalin (1) by following scheme:

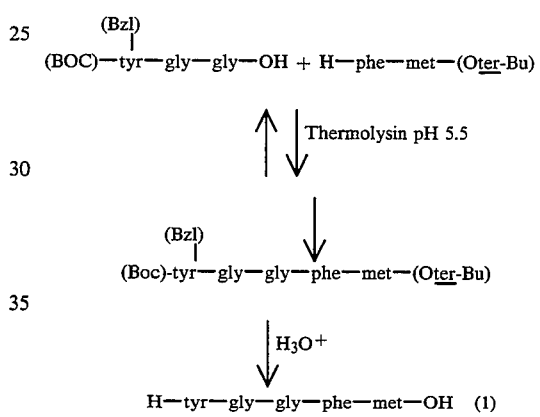

The feasibility of a stepwise total enzymatic synthesis of met-enkephalin using α-chymotrypsin and papain has been documented in the literature. See: W. Kullmann, *J. Biol. Chem* 255, 8234 (1980).

Another potentially useful application of the present invention is in the enzymatic synthesis of Gramicidin S (2) by the following scheme:

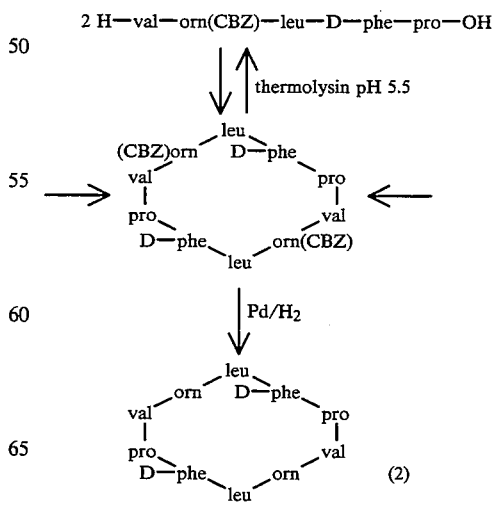

Various other examples of the enzymatic synthesis of useful peptide products where the present invention may find application and described in the literature are the synthesis of angiotensin, substance P, eledoisin, caerulein and leu-enkephalin.

Another useful class of peptide compounds amenable to proteosynthesis according to the present invention are the β-lactam antibiotics. This group comprises the well-known penicillins and cephalosporins, that are characterized by the presence of a β-lactam function in their chemical structure.

The high reactivity of the β-lactam function has made the chemical synthesis of those antibiotics difficult, and is responsible for their poor stability in aqueous solutions in the presence of nucleophiles. The enzyme β-lactamase specifically catalyzes the hydrolysis of the amide bond in the β-lactam ring of penicillins and cephalosporins. Nathan Citri, "Penicillinase and other β-Lactamases", in Paul D. Boyer (Ed.), "The Enzymes," Volume IV, 3rd Edition, Academic Press, New York 1971.

The presence of β-lactamases in the microbial world, particularly in Gram-negative bacteria, is considered a defensive mechanism against β-lactam antibiotics. The facile induction of this enzyme with penicillin has made possible the production of β-lactamase (penicillin β-lactam amidohydrolase, EC 3.5.2.6) by fermentation of resistant strains of *Bacillus cereus, Bacillus licheniformis* and *Escherichia coli*, E. J. Vandamme, "Penicillin acylases and β-lactamases," in A. H. Rose (Editor), "Microbial Enzymes and Bioconversions," Chapter 9, pp. 504–522, Academic Press, New York, 1980.

β-Lactamase may be used as a reverse hydrolase for the synthesis of a penicillin methyl ester B from the corresponding penicilloic acid A, according with the teachings of the present invention, the uncharged B being selectively transported over A across a hydrophobic membrane, and further made non-permeable by the action of an esterase to give the polar penicillin C.

chiral dicarboxylic acid diesters into chiral monoesters is well known [C. J. Sih et al., *Ann N.Y. Acad. Sci.* 471, 239 (1986)], the text of which is incorporated herein by reference. The same enzyme can be used in the fashion described in this invention for the resolution of racemic carboxylic acid compounds, through the selective transport of a chiral ester through the membrane and the retention of the non-reactive enantiomeric acid in the reaction phase.

The present invention utilizes standard biochemical terminology as follows: "H-val-" indicates that valine is the N-terminal amino acid residue of a peptide having the terminal amino group free; "-phe-OH" indicates that phenylalanine is the C-terminal amino acid residue of the peptide which has a C-terminal free carboxy group. Also "$V_{syn}$" indicates the average rate of synthesis and "$V_{perm}$" indicates the average rate of permeation.

The following detailed Examples are presented to further illustrate the present invention.

EXAMPLE 1

An aspartame derivative was prepared in accordance with the present invention as follows:

To a solution containing 5.02 g (20 mmoles) N-formyl-L-aspartyl-β-benzylester, 4.31 g (20 mmoles) L-phenylalanine methyl ester in 100 mL in water, adjusted to pH 5.5, was added 500 mg thermolysin enzyme (Daiwa Chem. Co., Osaka, Japan) representing a total of $8 \times 10^5$ proteolytic units.

The resulting clear reaction mixture was incubated for 15 hrs at 40° C., when the presence of insoluble dipeptide N-formyl-β-benzyl-L-aspartyl-L-phenylalanine methyl ester became apparent. The resulting mixture was then placed in a 200 mL vessel, connected to the reaction side, in this case tube side, of an experimental hollow-fiber separator of a Bend Research, Inc. "Type 1 Hollow Fiber Selective Dialysis Membrane" that provided 1 square foot of membrane area. The

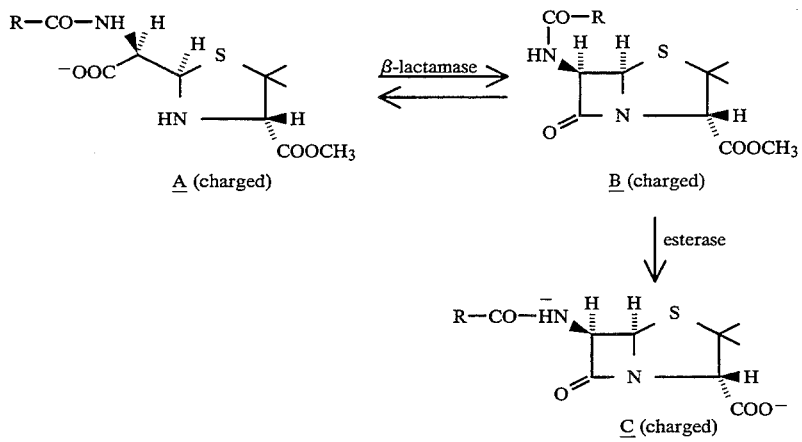

This approach could facilitate the synthesis of penicillins from penicilloic acid precursors, that are per se amenable to total synthesis. J. C. Sheehan and K. R. Henery-Logan, *J. Am. Chem. Soc.* 84, 2983 (1962).

Those skilled in the art will appreciate that the present invention may also find application to compounds other than peptides, peptide like compounds and equivalents thereof.

For example, the use of ester hydrolases like pig liver esterase [3.1.1.1] for the asymmetric resolution of proproduct side of the membrane (shell side of the separator) was connected to a source of aqueous (product) mixture (total volume=200 mL) containing 500 mg of the enzyme Acylase I (EC 3.5.1.14) from *Aspergillus sp.* (Sigma A 2156), at pH 7.5. This enzyme, usually described as an aminoacylase, was found to function as a C-terminal esterase, on both N-acetyl- and N-formyl-β-benzyl aspartame.

The reaction and product mixtures were circulated at room temperature through the hollow fiber separator countercurrently at the rate of 600 mL/min, with the assistance of peristaltic pumps. The configuration of this apparatus resembles that illustrated in FIG. 2. Since the pH in both the reaction and product mixtures drops as the process progresses, constancy of pH was maintained through the use of pH stats.

The formation of N-formyl-$\beta$-benzyl-L-aspartyl-L-phenylalanine was monitored by HPLC. Chromatographic analysis was conducted on a Tracor Model 995 instrument along with a LDC Spectromonitor II detector set at 254 nm for the detection of the amino acids, fully protected product dipeptide, and dipeptide. The column used was NOVA-PAK $C_{18}$ Radial-Pak cartridge, 8 mm×10 cm, housed in a Millipore Waters RCM-100 Radial Compression Module.

The mobile phase used for the detection of the fully protected dipeptide was a v/v mixture of 45% methanol (HPLC grade) 5% tetrahydrofuran (HPLC grade); and 50% of a $KH_2PO_4$ buffer solution. For the detection of the product dipeptide, the mobile phase consisted of a v/v mixture of 40% methanol and 60% of a 1% $KH_2PO_4$ buffer solution (1 mL of triethylamine per liter solvent was added to minimize tailing and the pH was adjusted down to 4.3 using phosphoric acid). The flow rate was kept at 1 mL/minute.

The HPLC data relating to formation of N-formyl-$\beta$-benzyl-L-aspartyl-L-phenylalanine is summarized in Table II below, and is expressed as the total amount (mg) of product dipeptide accumulated in the product solution as a function of time.

Figure 3:
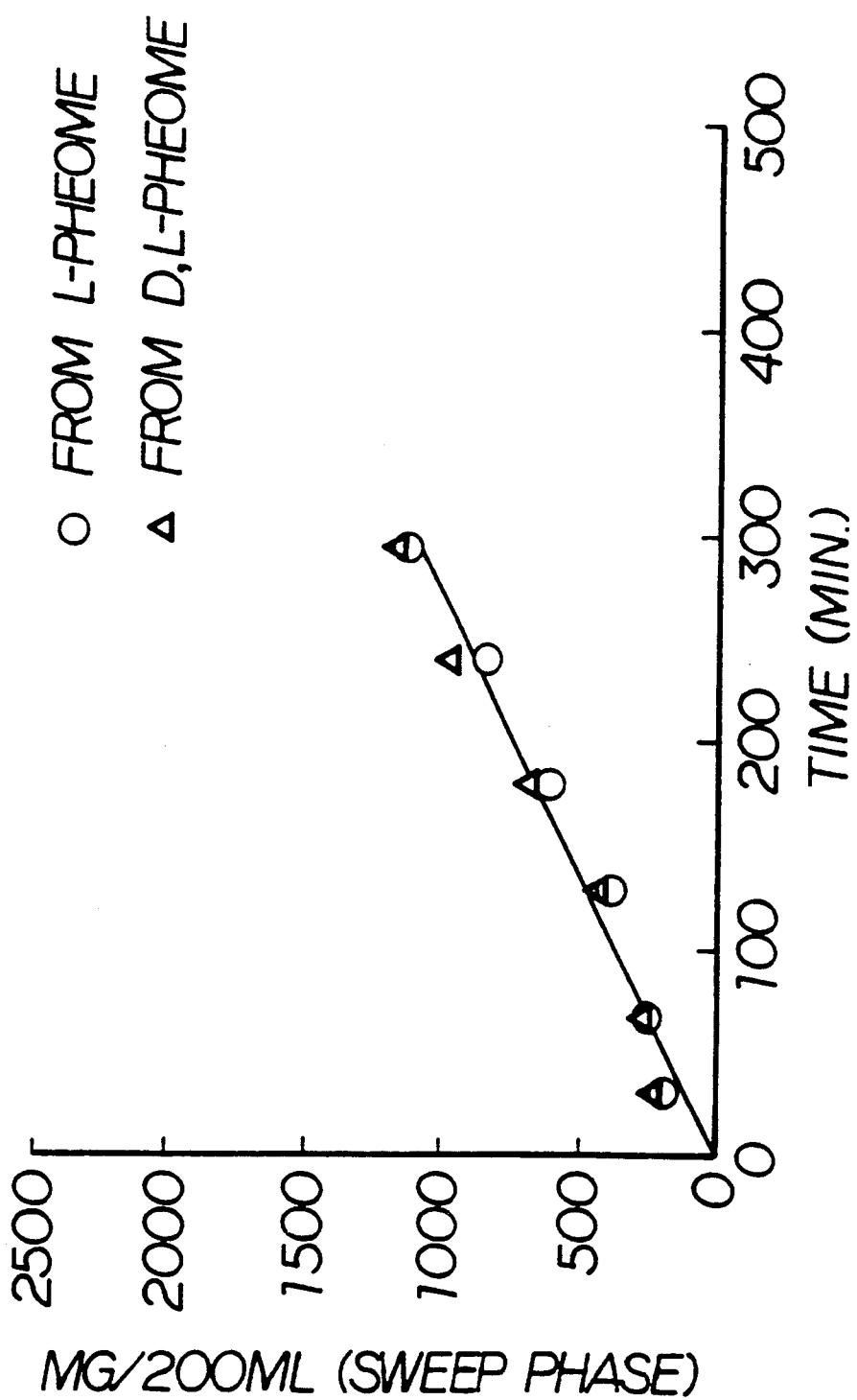
FIG. 3 is a graph illustrating the quantity of product (aspartame derivative) formed over time in Examples 1 and 2.

The value of the uncharged dipeptide concentration at equilibrium which corresponds to its saturation point in water at pH 5.5, was found to be about 0.05% at 25° C. The amount of uncharged dipeptide transported per square foot of membrane per hour was found to be about 200 mg, indicating that maintenance of the equilibrium required dissolution of insoluble dipeptide and/or dipeptide synthesis de novo. Almost complete dissolution of the insoluble uncharged phase dipeptide in the reaction mixture was observed after about 5 hrs, when the reaction was stopped. A plot of the data of Table II is shown in FIG. 3. The linear function indicates that the transfer of peptide across the membrane proceeds at a steady state. The observed rate of formation of product dipeptide of about 200 mg/ft²/hr (Table II) was confirmed similar to the flux of uncharged dipeptide across the membrane (190 mg/ft²/hr) measured at 0.05% in water as was anticipated on theoretical grounds.

At this point the described system would be expected to continue in steady state if continuous addition were made to the reaction mixture of the two amino acid reactants, at a rate of about 120 mg/hr each, to keep the system saturated in uncharged dipeptide.

In order to fully realize the membrane's selectivity the intercalation of a second membrane in series with the first membrane before the contact with the second enzyme may be necessary because the selectivity across a single membrane is lower due to the high amino acid concentration in the reaction solution.

The product solution (200 mL) was recovered, adjusted to pH 2.5 and cooled at 4° C. overnight. The precipitate collected was recovered and recrystallized from MeOH:H₂O to give 307 mg of N-formyl-$\beta$-benzyl-L-aspartyl-L-phenylalanine $[\alpha]_D^{25°} = -5.6°$ (C=1.2; EtOH), identical (IR, 13C-NMR) to an authentic sample prepared by the batch hydrolysis of N-formyl-$\beta$-benzyl-aspartame with Aspergillus esterase, $[\alpha]_D^{25°} = -5.3°$ (C=1.3; EtOH).

TABLE II

| Time (min) | Amount peptide/product solution (mg) |
|---|---|
| 30 | 124 |
| 60 | 228 |
| 120 | 412 |
| 180 | 617 |
| 240 | 882 |
| 300 | 1015 |

EXAMPLE 2

An experiment similar to that of Example 1 was conducted, except for the use of 8.63 g D,L-phenylalanine methyl ester instead of the L-enantiomer. The results are summarized in Table III. Isolation of the uncharged peptide from the 200 mL of product solution gave 310 mg of product, $[\alpha]_D^{25°} = -6.4°$ (C=1.4; EtOH), identical in all respects (IR, 13C-NMR) to an authentic sample of N-formyl-$\beta$-benzyl-L-aspartyl-L-phenylalanine.

TABLE III

| Time (min) | Amount peptide/product solution (mg) |
|---|---|
| 30 | 166 |
| 60 | 258 |
| 120 | 475 |
| 180 | 686 |
| 240 | 996 |
| 300 | 1073 |

A plot of the data summarized in Table III (FIG. 3) again showed the existence of a steady state process when the reactor was operated with D,L-phenylalanine methyl ester. The stereospecificity of thermolysin is demonstrated by the exclusive formation of the same L,L-dipeptide described in Example 1. The D-phenylalanine methyl ester retained in the tube phase (reaction mixture) did not inhibit the overall kinetics of peptide formation.

EXAMPLE 3

A mixture of 1.0 g N-formyl-$\beta$-benzyl-L-aspartyl-L-phenylalanine, prepared in accordance with Example 1, 4.0 mL water, 4.0 mL tetrahydrofuran, and 1.0 mL conc. hydrochloric acid (12N) was heated at reflux for 9 hrs. The mixture was then cooled and the pH adjusted to 4.0 with 50% NaOH solution. The tetrahydrofuran was then removed by evaporation at <35° and 20 mm Hg. Crystallization was completed by storage at 5° C. for 1 hr, the sample then filtered, washed with 1 mL ice water, and dried in vacuo to give 367 mg of white solid. This material was identical to an authentic sample of aspartyl phenylalanine by HPLC and IR comparison $[\alpha]_D^{25°} = +12°$ (C=0.5; 0.1N HCl in 50% MeOH).

Aspartyl phenylalanine has been converted to aspartame by treatment with methanol and hydrochloric acid, as described in G. L. Bachman and B. D. Vineyard, U.S. Pat. No. 4,173,562, example #1.

EXAMPLE 4

An experiment similar to that of Example 1 was conducted, except for the use 5.65 g (20.1 mmoles) N-carbobenzoxy-L-aspartic acid $\beta$-methyl ester and 4.38 g (20.3 mmoles) L-phenylalanine methyl ester as reactants. The amino acids were dissolved in 100 mL water, the pH of the solution adjusted to 5.5, and 500 mg of thermolysin Daiwa (8×10⁵ proteolytic units) was added. The solution was preincubated for 15 hours at 40° C., when a substantial amount of N-CBZ-(β-methyl ester)-L-asp-L-phenylalanine methyl ester was precipitated. The suspension was connected to the tube side of a "Type 1 Hollow Fiber Selective Dialysis Membrane" (Bend Research Inc.) containing 1 ft² of membrane surface, and the machine was operated at room temperature for 5 hours against a shell side phase of 200 mL water containing 500 mg Acylase I (Sigma) at pH 7.5. The accumulation of peptide product in shell phase was monitored by HPLC, and the results are reproduced in Table IV and FIG. 4.

After 5 hours run the reaction was stopped, the shell side phase (200 mL) was recovered, adjusted to pH 2.5, and stored overnight at 4° C. The product precipitated was collected and recrystallized from CH$_3$OH:H$_2$O to yield 405 mg (86% recovery) of N-CBZ-(β-methyl ester)-L-asp-L-phenylalanine (N-CBZ-iso-APM) $[\alpha]_D^{25°} = +6.0°$ (C=1.1, EtOH), identical (¹³C-NMR) to an authentic sample of N-CBZ iso-APM, $[\alpha]_D^{25°} = +5.5°$ (C=1.1, EtOH), prepared by chemical coupling and partial esterolysis with Acylase I.

TABLE IV

| Time (min) | Amount peptide/product solution (mg) |
| --- | --- |
| 30 | 177 |
| 60 | 214 |
| 120 | 333 |
| 180 | 381 |
| 240 | 459 |
| 300 | 470 |

Figure 4:
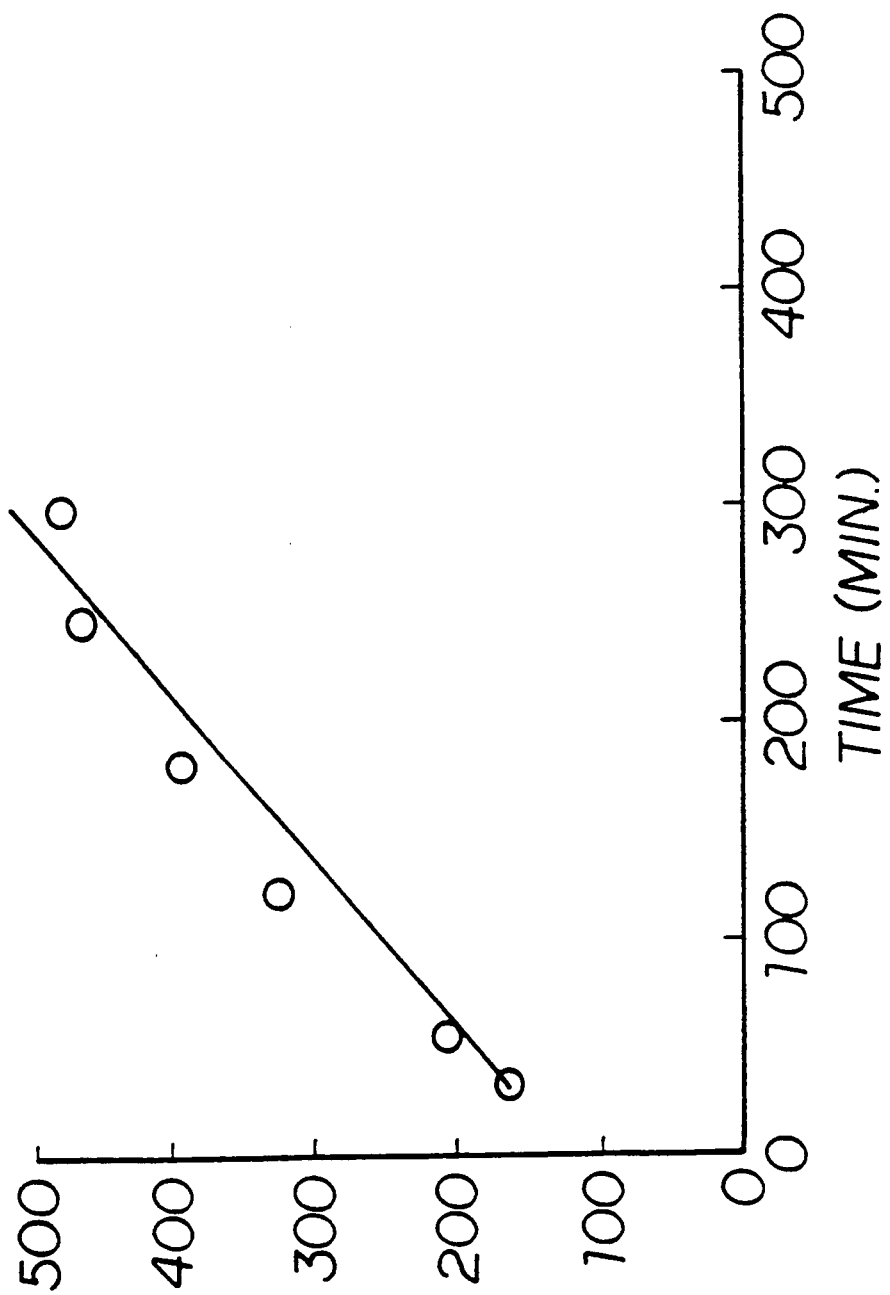
FIG. 4 is a graph illustrating the quantity of product (aspartame derivative) formed over time in Example 4.

As observed before in the experiments of Examples 1 and 2, the plot of FIG. 4 indicates that the accumulation of N-CBZ-iso-APM proceeded at a steady rate of about 200 mg/hr.

The conversion of N-CBZ-iso-APM to APM can be practiced under the conditions described in Example 3.

EXAMPLE 5

The aspartame derivative, N-formyl-(β-methyl)-asp-phe-OH was prepared in accordance with the present invention as follows: To a solution containing 6.00 g (35 mmoles) of N-formyl-(β-methyl)-L-aspartic acid, 10.00 g (48 mmoles) L-phenyl alanine methyl ester in 100 mL water, adjusted to pH 7.0, was added 770 mg thermolysin enzyme (Daiwa Chemical Co., Osaka, Japan) representing a total of 1.2×10⁶ proteolytic units. The resulting clear solution was incubated for 1 hr at 40° C., when HPLC analysis indicated the presence of 433.8 mg of N-formyl-(β-methyl)-asp-phe-OMe. The solution was cooled to 25° C., the pH adjusted to 5.0, and the solution placed in a 200 mL vessel connected to the tube side of hollow-fiber separator ("Type 2 Hollow Fiber Selective Dialysis Membrane", Bend Research Inc.) that provided 0.5 ft² (450 cm²) of a ILM made of 30% v/v N,N-diethyl-dodecanamide in dodecane. The shell side of the separator was connected to the product vessel containing 500 mg of the enzyme Acylase I (EC 3.5.1.14) from *Aspergillus Sp.* (Aminoacylase AMANO, Nagoya, Japan), at pH 7.5.

The two phases were circulated at 25° C. countercurrently, at the rates of 50 mL/min. (tube phase) and 500 mL/min. (shell phase), with the assistance of two peristaltic pumps using the configuration illustrated in FIG. 2. Constancy of pH in both phases was secured through the use of pH stats.

The formation of N-formyl-(β-methyl)-asp-phe-OH was monitored by HPLC, using a Tracor Model 995 instrument together with a LDC Spectromonitor II detector set at 254 nm. The column used was a NOVA-PAK C18 Radial-Pak cartridge, 8 mm×100 mm, housed in a Millipore Waters RCM-100 Radial Compression Module.

The mobile phases used for the analysis were:
(a) for N-formyl-(β-methyl)-asp-phe-OMe: 40% v/v methanol in 0.1% KH$_2$PO$_4$ buffer pH 4.6;
(b) for N-formyl (β-methyl)-asp-phe-OH: 20% v/v methanol in 0.1% KH$_2$PO$_4$ pH 4.6; flow rates used were 1 mL/min for both analyses.

The data relating to the formation of N-formyl-(β-methyl)-asp-phe-OH (product dipeptide) is reproduced in Table V below, and is expressed as the total amount (mg) accumulated in the 200 mL shell phase as a function of time.

TABLE V

| Time (min) | Amount peptide/product solution (mg) |
| --- | --- |
| 60 | 130 |
| 120 | 230 |
| 180 | 280 |
| 240 | 360 |
| 300 | 400 |

Figure 5:
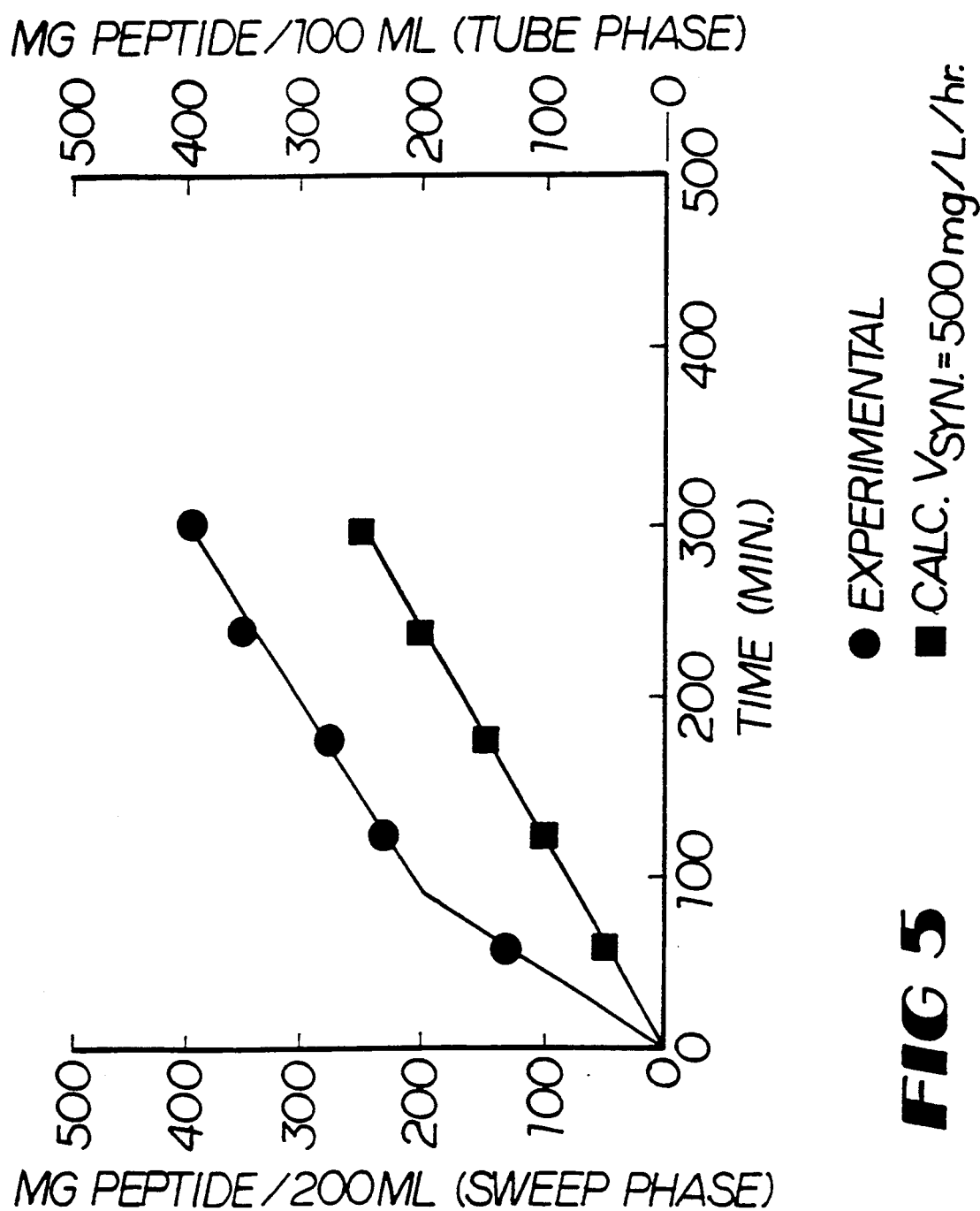
FIG. 5 is a graph illustrating the quantity of product (aspartame derivative) formed over time in Example 5.

A plot of the data of Table V shown in FIG. 5.

At the end of the run, HPLC analysis indicated the presence of 283 mg of N-formyl-(β-methyl)-asp-phe-OMe in the tube phase. These values permitted calculation of the amount of peptide synthesized during the operation of the reactor.

$P_{tr}$ = peptide transferred into shell phase = 400.

$$\frac{336}{322} = 417.4 \text{ mg};$$

$P_o$ = initial peptide in tube phase = 433.8 mg;

$P_T$ = peptide remaining in tube phase at the end of the run = 283 mg;

$$P_{tr} = (P_o - P_T) + P_{syn};$$

$$P_{syn} = P_{tr} - (P_o - P_T) = 266.6 \text{ mg};$$

and $$V_{syn} = \frac{266.6}{5} = 53.5 \text{ mg/hr. 100 mL.}$$

The $V_{syn}$ of 53.5 mg/hr. 100 mL coincides with the rate of synthesis (500 mg/hr. L) measured for the forward velocity in equilibration studies done with N-formyl-(β-methyl)-L-aspartic acid and L-phenylalanine methyl ester in the presence of thermolysin.

The product solution (200 mL) was recovered, adjusted to pH 2 with 1N HCl and extracted twice with 200 mL EtOAc. The combined extracts left a white residue upon evaporation, that after recrystallization from EtOAc/hexane yielded 100 mg of N-formyl-(β-methyl)-L-asp-L-phe-OH, $[\alpha]_D^{25°} = +0.70°$ (c, 0.29;MeOH), identical (IR, ¹³C-NMR) to an authentic sample prepared by the batch hydrolysis of synthetic N-formyl-(β-methyl)-L-asp-L-phe-OMe with Aspergillus esterase, $[\alpha]_D^{25°} = +0.80°$ (c, 0.29; MeOH).

EXAMPLE 6

The experiment described in Example 5 was scaled up in a Type 2 Hollow fiber Dialysis Membrane (Bend Research Inc.), containing 1 ft$^2$ of liquid membrane (30% v/v N,N-diethyl-dodecanamide in dodecane). The tube phase contained 40 g L-phe-OMe, 24 g N-formyl-($\beta$-methyl)-L-asp and 3.08 g thermolysin Daiwa (a total of 5×10$^6$ proteolytic units) in 400 ml water, adjusted to pH 7.0. After an incubation period of 1 hr at 40° C., the amount of 1,068 g (2.7 g/L) of N-formyl-($\beta$-methyl)-L-asp-L-phe-OMe was found to be present. The solution was cooled to 25° C., adjusted to pH 5.0 with 1N HCl, and connected to the tube side of the hollow fiber separator. The shell phase was made of 400 mL water, pH 7.5, containing 2 g aminoacylase I (Amano). The two phases were circulated countercurrently at 25° C. for 5 hrs., as described in Example 5. The results are summarized in Table VI and FIG. 6.

TABLE VI

| Time (min) | Amount peptide/product solution (mg) |
| --- | --- |
| 30 | 204 |
| 60 | 251 |
| 120 | 445 |
| 180 | 634 |
| 240 | 748 |
| 300 | 843 |

At the end of the run, the amount of N-formyl-($\beta$-methyl)-asp-phe-OMe remaining in tube phase was 586 mg.

Figure 6:
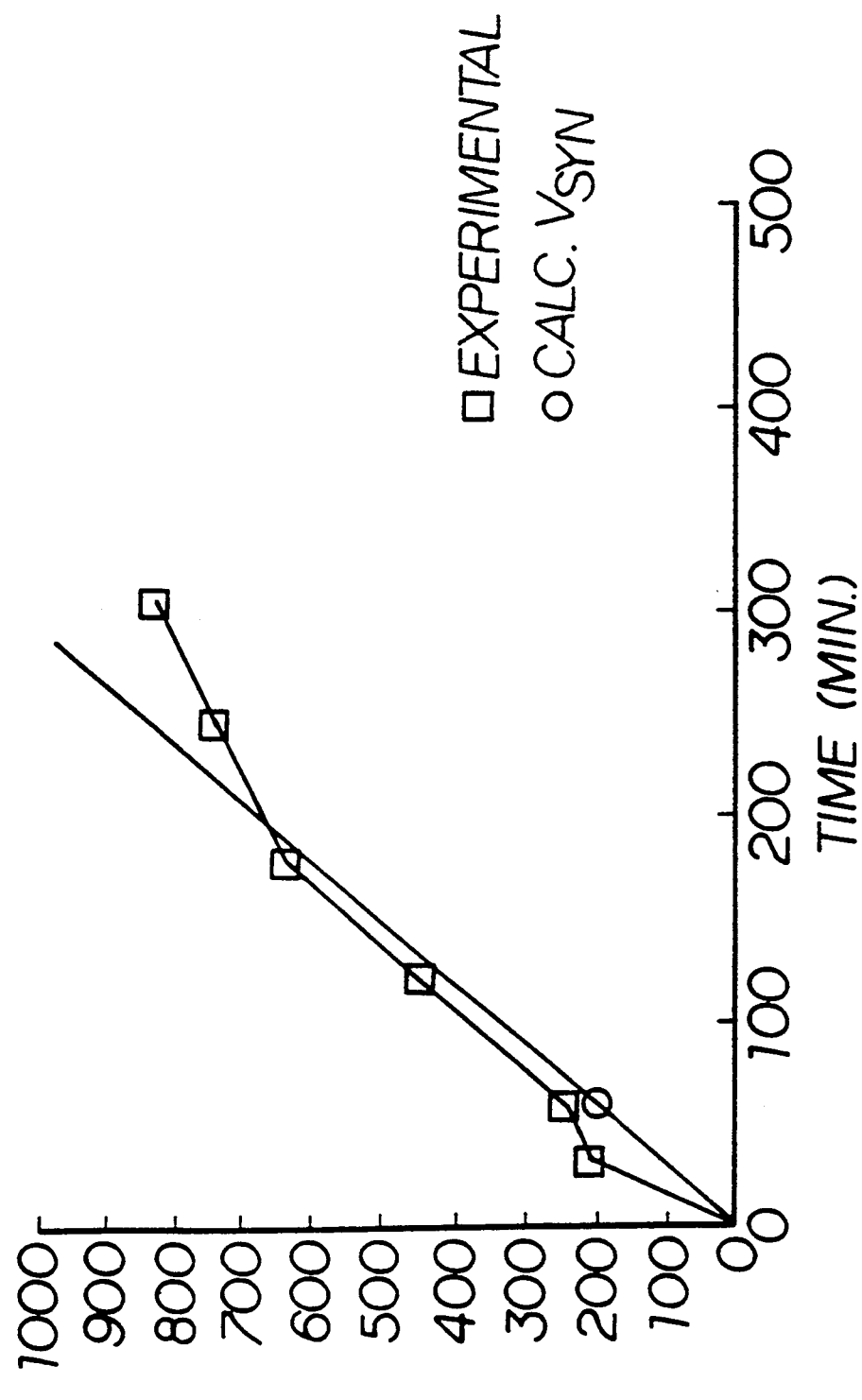
FIG. 6 is a graph illustrating the quantity of product (aspartame derivative) formed over time in Example 6.

The highest transport value observed (404 mg/hr) during the first 30 min. is the result of the high initial peptide concentration produced during the preincubation period. Departure from equilibrium caused by the transport of peptide set in the synthesis of more peptide, thus establishing a steady state condition after the first hour into the run, at the expected level of 200 mg/hr (FIG. 6).

EXAMPLE 7

Figure 7:
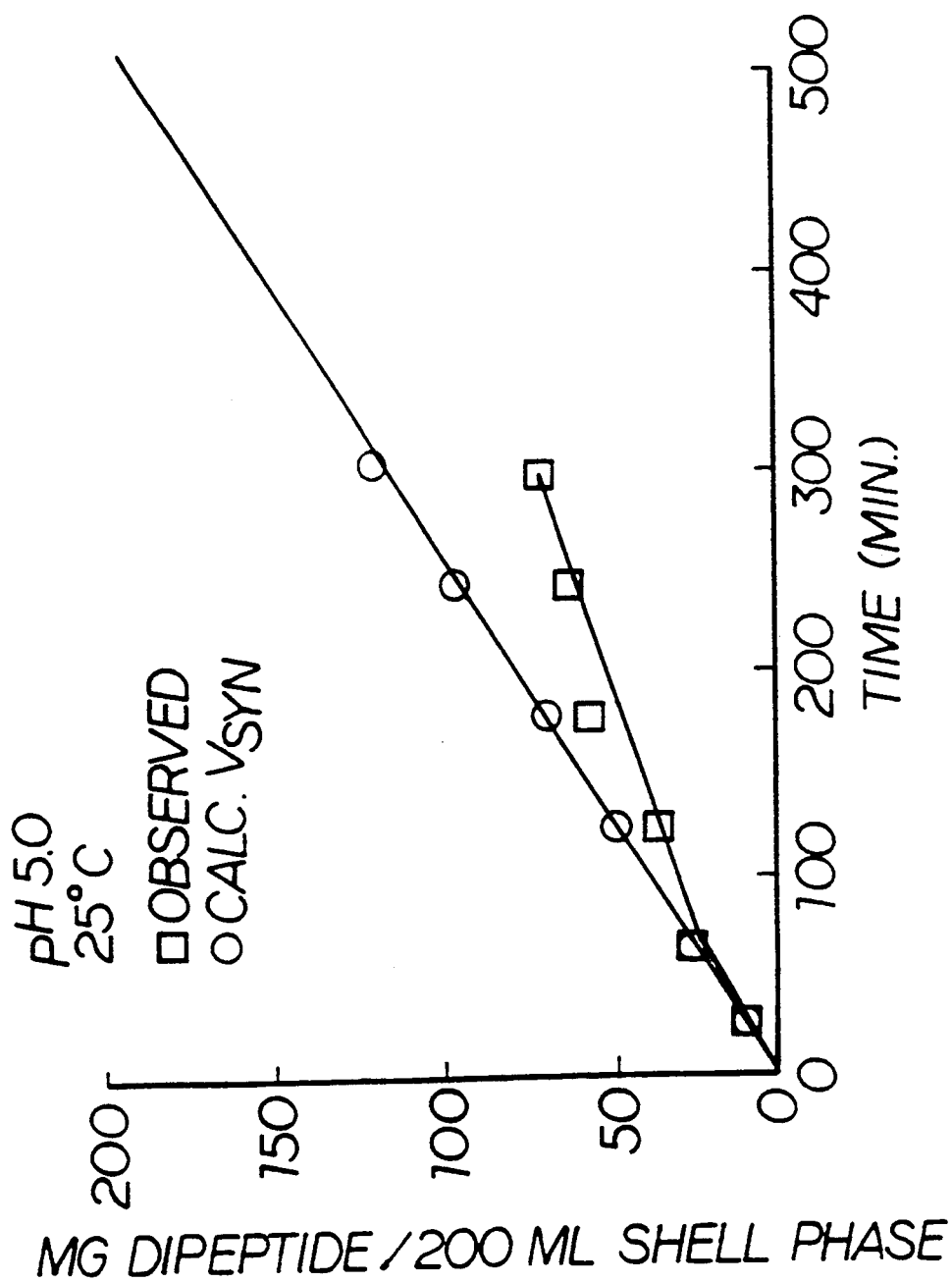
FIG. 7 is a graph illustrating the quantity of product (aspartame derivative) formed over time in Example 7.

An experiment similar to that of Example 5 was conducted, except for the use of 10.00 g of D,L-phenylalanine methyl ester instead of the L-enantiomer. The results, presented in Table VII and FIG. 7, clearly show that the observed rate of formation of N-formyl-($\beta$-methyl)-L-asp-L-phe-OH was one-half of that seen with L-phe-OMe (Example 5, Table V), as expected from the enantioselectivity of thermolysin and the prior results of Examples 1 and 2.

TABLE VII

| Time (min) | Amount peptide/product solution (mg) |
| --- | --- |
| 30 | 10.6 |
| 60 | 25.5 |
| 120 | 33.2 |
| 180 | 55.3 |
| 240 | 59.6 |
| 300 | 69.1 |

EXAMPLE 8

Membrane-assisted enzymatic resolution of D,L-phenylalanine methyl ester was utilized in accordance with the present invention as follows: To a solution of 1.0 g (5.6 mmoles) of D,L-phenylalanine methyl ester in 100 mL water, pH 7,5, was added 500 mg of aminoacylase I (Areano Pharmaceutical Co., Nagoya, Japan). The mixture was allowed to react at 25° C. for SO min., at the end of which the presence of 266 mg L-phe-OH (1.6 mmoles) and 712 mg D,L-phe-OMe (4 mmoles) was observed by HPLC analysis. This solution was fed to the tube (reaction) side of a hollow-fiber Celgard supported ILM separator ("Type 2 Hollow Fiber Selective Dialysis Membrane", Bend Research Inc.) containing 0.5 ft$^2$ of a 30% v/v N,N-diethyl-dodecanamide in dodecane liquid film in it. The product side of the membrane (shell side of the separator) was filled with 200 mL water adjusted to pH 2.0 with diluted HCl. The two phases were circulated through the separator countercurrently at the rate of 200 mL/min., with the assistance of peristaltic pumps (FIG. 2). The separation proceeded through the continuous addition of D,L-phe-OMe to the tube phase, done at a rate of about 1 g D,L-phe-OMe per hour. A total of 30 mL of a 7% solution of D,L-phe-OMe (2.1 g; 11.7 mmoles) in water pH 7.5 was added in a period of 2 hrs. The pH of both phases was kept constant by the use of pH stats.

Figure 8:
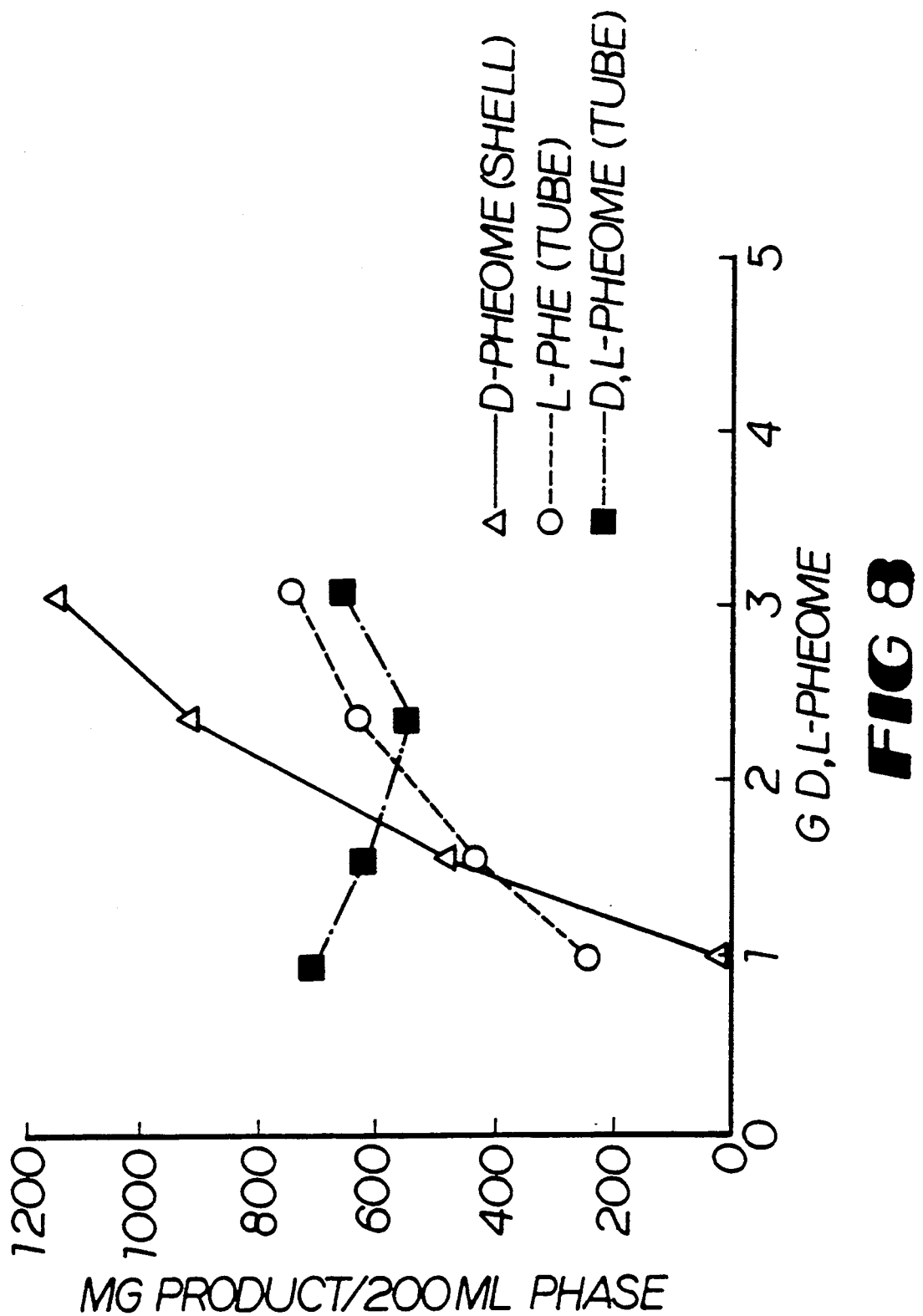
FIG. 8 is a graph illustrating the enzymatic resolution of DL-phe-OMe described in Example 8.

The course of the resolution was followed by HPLC, on samples taken from both phases every 30 min. The HPLC instrumentation and procedures are those described in Example 5. The mobile phase used in this case was 20% v/v methanol in 0.1% KH$_2$PO$_4$ buffer pH 4.6; with a flow rate of 1 mL/min. The results, presented in Table VII and plotted in FIG. 8, showed the accumulation of L-phe-OH in tube phase and of D-phe-OMe in shell phase. At the end of the experiment both phases were recovered and worked out as follows:

(a) Tube phase: The contents (130 mL) were adjusted to pH 8.5 with 1N NaOH, then extracted with 2×50 mL EtOAc. The aqueous phase was then adjusted to pH 4.0 with 1N HCl and the solution passed through a 2.5×20 cm Dowex 50 (NH$_4$) column. After washing with 200 mL water, the product was eluted with 200 mL of 10% NH$_4$OH. The eluate was concentrated to 50 mL in vacuo, and the solution freeze-dried. Yield: 249 mg, white solid, L-phenylalanine, $[\alpha]_D^{25°}=-29.2°$ (c, 2; H$_2$O), lit. (Aldrich) $[\alpha]_D^{25°}=-35.0°$ (c2;H$_2$O), optical purity 92%.

(b) Shell phase: (200 mL) was adjusted to pH 8.5 with diluted NaOH and extracted with 2×50 mL EtOAc. The organic extract was dried over anh. Na$_2$SO$_4$, evaporated to dryness, dissolved in 50 mL water acidified to pH 3.0 with 1N HCl and then freeze-dried, to yield 989 mg (4.6 mmole) of D-phe-OMe. HCl, white solid, $[\alpha]_D^{25°}=-21.0°$ (c, 2; EtOH) lit (Aldrich) $[\alpha]_D^{25°}=-32.4°$ (c, 2; EtOH), optical purity 83%.

Based on the permeability value of 32 mg/cm$^2$. min found for phe-OMe (water, pH 8, 25° C.) on this membrane, the expected flux for a membrane area of 450 cm$^2$ (0.5ft$^2$) was 880 mg/hr. Table VIII shows that the amount of phe-OMe transferred into the shell phase at the end of the first hour was 860 mg, suggesting that the transport was operating under membrane-limiting conditions.

TABLE VIII

| D,L—phe—OMe added (g) | Tube Phase | | Shell Phase |
| --- | --- | --- | --- |
| | L—phe—OH (mg) | D,L—phe—OMe (mg) | D—phe—OMe (mg) |
| 1.0 | 2.46 | 712 | 0 (0 min) |

TABLE VIII-continued

| D,L—phe—OMe added (g) | Tube Phase | | Shell Phase |
| --- | --- | --- | --- |
| | L—phe—OH (mg) | D,L—phe—OMe (mg) | D—phe—OMe (mg) |
| 1.7 | 473 | 617 | 537 (30 min) |
| 2.4 | 615 | 531 | 860 (60 min) |
| 3.1 | 743 | 628 | 1154 (90 min) |

Batch resolution of D,L-phe-OMe through the enantioselective hydrolysis of the methyl ester function catalyzed by subtilisin A (a serine-type alkaline protease) has been recently disclosed [Shui-Tein Chen, Kung-Tsung Wang and Chi-Huey Wong, *J. Chem. Soc. Chem. Commun.* 1986, 1514]. A hydrolase is required for membrane resolution of racemic carboxylic acid ester compounds. A hydrolase which is a protease having esterolytic activity such as aminoacylase I, α-chymotrypsin and subtilisin A can be utilized to resolve a D,L-amino acid compounds such as D,L-phenylalanine methyl ester. Also, the membrane-assisted process of the present invention can be practiced by substituting subtilisin A or α-chymotrypsin for the preferred aminoacylase I. Aminoacylase I is generally preferred for the esterolysis of peptides over other esterolytic enzymes such as subtilisin A and α-chymotrypsin also having endo-proteolytic activities.

If the above described resolution of D,L-phenylalanine methyl ester is utilized to produce a peptide as described in the present invention, the L-phenylalanine produced is converted to L-phenylalanine methyl ester by standard procedures known in the art.

This example may be adaptable for resolution of other racemic carboxylic acid esters. For example, a racemic carboxylic acid ester compound in an aqueous reaction mixture including a hydrolyzing enzyme can be hydrolyzed to form a charged enantiomeric compound and an uncharged enantiomeric ester compound in the aqueous reaction mixture. The uncharged enantiomeric ester compound is then transported from the aqueous reaction mixture across an ion rejection membrane of the present invention including Type 1 or Type 2 Hollow Fiber Selective Dialysis Membranes from Bend Research, Inc. In one type of example such as Example 8, the racemic carboxylic acid ester compound is a D,L-amino acid ester compound; the charged enantiomeric compound is a L-amino acid compound and the uncharged enantiomeric ester compound is a D-amino acid ester compound. It will be appreciated that the selection of enzymes and reaction conditions is within the understanding and knowledge of persons skilled in the art of the present invention.

Continuous or batch processing means are provided by this Example in that the desired enantiomer of the reactant can be produced and added to the reaction mixture.

EXAMPLE 9

Synthesis of N-formyl-($\beta$-methyl)-L-asp-L-phe-OH in accordance with the present invention was conducted utilizing immobilized aminoacylase I and ion-exchange resins for the removal of permeable products as follows: To a solution of 10.0 g (48 moles) L-phenylalanine methyl ester and 6.0 g (35 mmoles) of N-formyl-($\beta$-methyl)-L-aspartic acid in 100 L deionized water, adjusted to pH 7.0, was added 770 mg of thermolysin ($E_1$) (Daiwa Chemical Company, Osaka, Japan) representing a total of $1.2 \times 10^6$ proteolytic units. The resulting solution was incubated for 1 hr. at 40° C., when HPLC analysis indicated the presence of 383 mg of N-formyl-($\beta$-methyl)-asp-phe-OMe. The solution was cooled to 25° C., the pH adjusted to 5.0, and the solution was placed in a 200 mL vessel 40 connected to the tube side 46 of a hollow fiber separator 44 ("Type 2 Hollow Fiber Selective Dialysis Membrane", Bend Research, Inc.) containing 900 cm² (1 ft²) of a hydrophobic liquid membrane made of 30% N,N-diethyldodecanamide in dodecane. The shell side of the separator 48 was arranged as a closed circuit made of a series of connecting vessels illustrated in FIG. 9. The solution returning to the separator 44 was adjusted to pH 4.0 in order to protonate the L-phe-OMe copermeating with the dipeptide N-formyl-($\beta$-methyl)-asp-phe-OMe. Circulation through a column of Dowex 50 (Na+) 50 removed the positively charged L-phe-OMe, leaving the uncharged dipeptide in solution. The effluent was adjusted to pH 7.0 and submitted to the action of the aminoacylase I ($E_2$), immobilized over DEAE-Sephadex 52 IT. Tosa, T. Mori and I. Chibata, *Agr. Biol. Chem.* 33, 1053 (1969)]. The resulting dipeptide N-formyl-($\beta$-methyl)-asp-phe-OH was negatively charged at that pH, and was subsequently captured by the Dowex 1 (Cl-) resin 54. The column effluent 57 was returned to the membrane separator with prior adjustment to pH 4.0 58, thus closing the loop.

The tube 46 (100 mL) and shell 48 (500 mL) phases were circulated at 25° C. countercurrently through the membrane separator, at the rates of 50 mL/min. (tube phase) and 120 mL/min. (shell phase).

Figure 9:
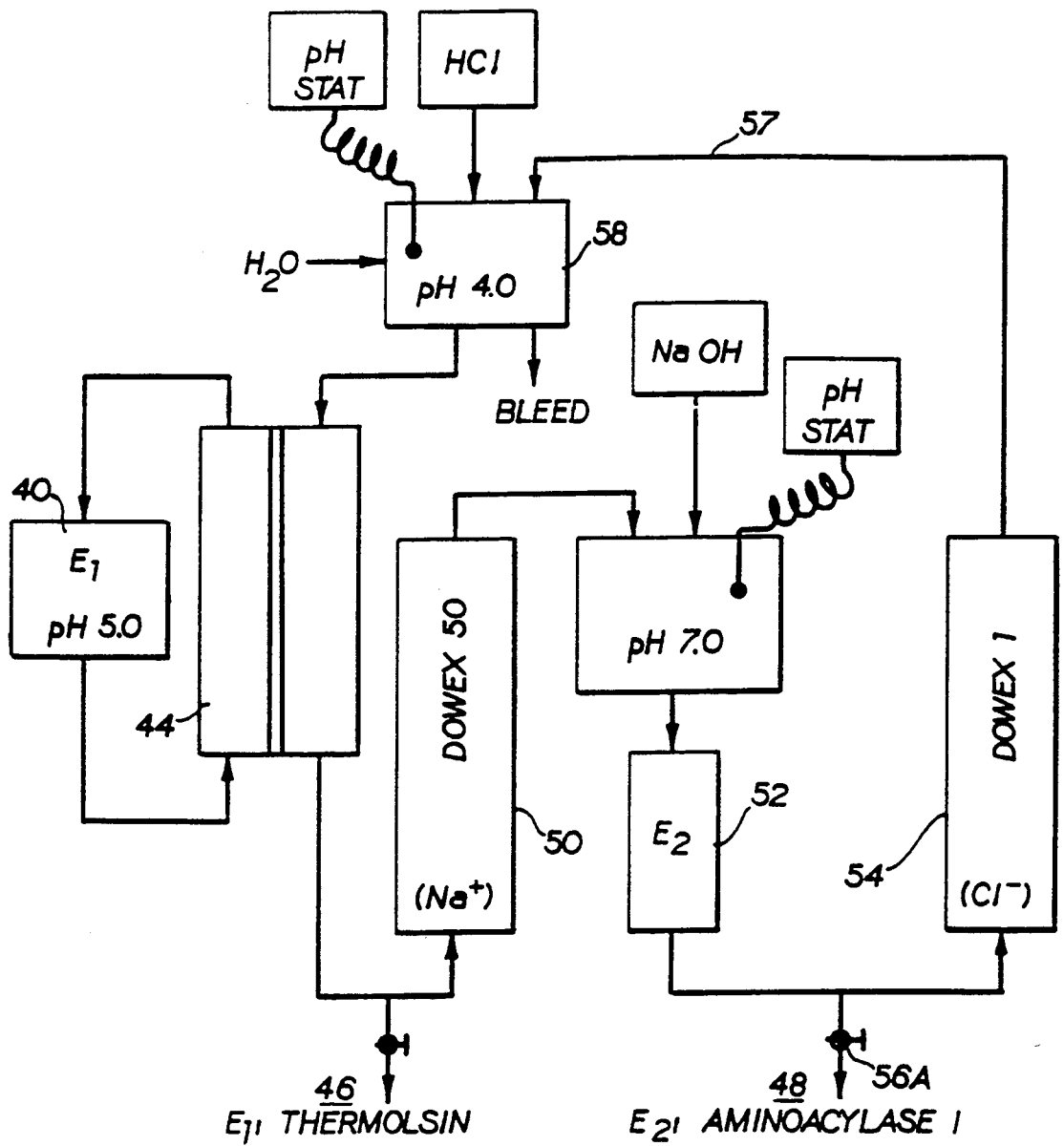
FIG. 9 is a schematic representation of an apparatus for practicing the present invention which illustrates the vessels on the product side as described in Example 9.

Periodic sampling of the shell phase was done on the effluent from the second enzyme ($E_2$), (FIG. 9, sampling port 56, before entering the Dowex 1 (Cl-) column 54) and the samples monitored by HPLC following the procedures described in Example 5. As expected, at this point of the circuit (FIG. 9) no L-phe-OH that could result from the enzymatic hydrolysis of L-phe-OMe by $E_2$ (see Example 8) was detected; only a circulating steady-state level of N-formyl-($\beta$-methyl)-asp-phe-OH (average concentration: 54 mg/L) was observed, reflecting the continuous transfer of the dipeptide N-formyl-($\beta$-methyl)-APM across the membrane and its subsequent hydrolysis by $E_2$. The efficient trapping of the charged dipeptide by the Dowex-1 resin is indicated by the low concentration of it observed at the column effluent 57 throughout the run.

Figure 10:
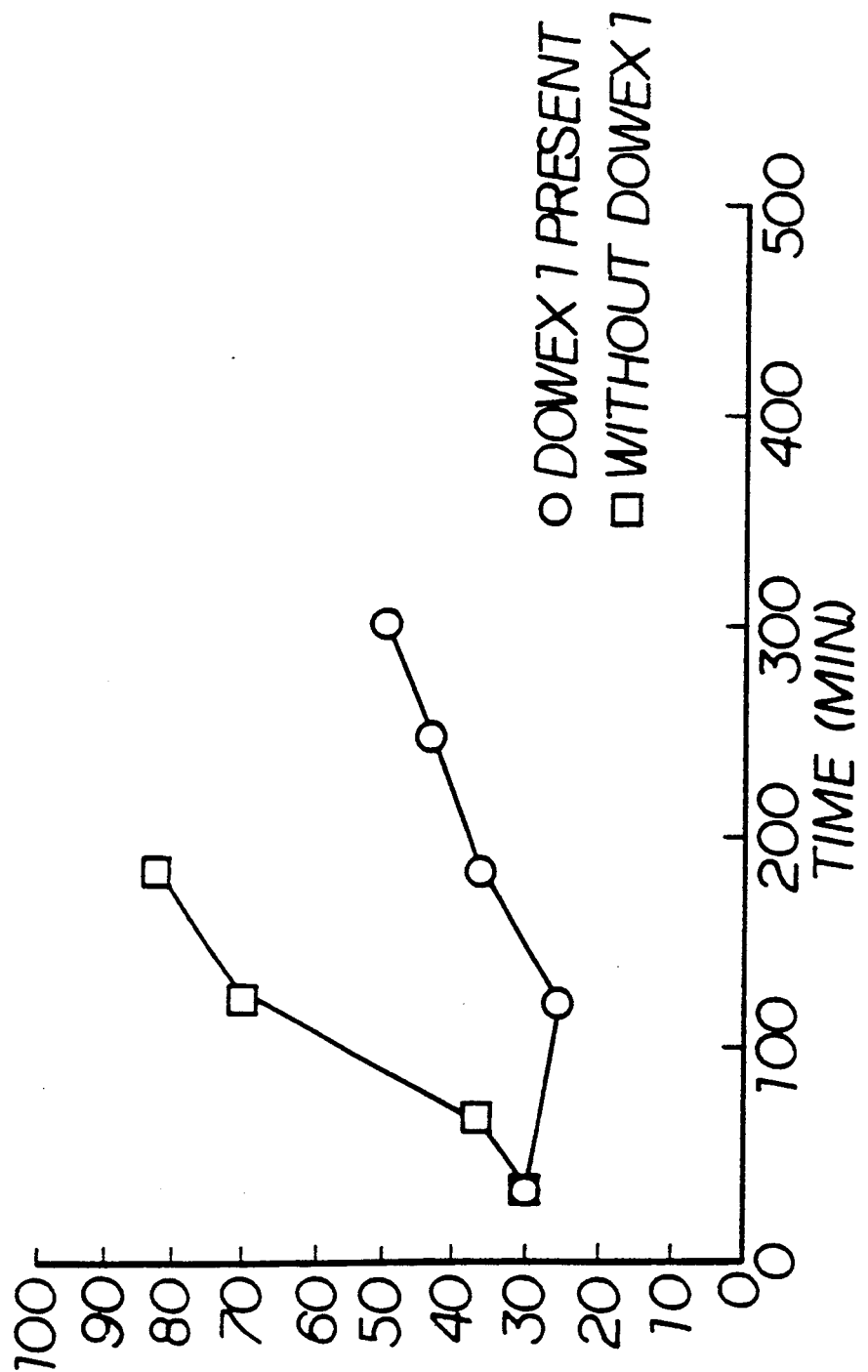
FIG. 10 is a graph illustrating the quantity of product (aspartame derivative) formed over time in Example 9 with and without the utilization of an ion exchange resin.

A similar parallel experiment performed in the absence of Dowex-1 showed the rapid accumulation of N-formyl-($\beta$-methyl)-asp-phe-OH in the shell phase, as could be anticipated from the results discussed above. Again, no L-phe-OH was found in the circulating shell phase. A comparison of both experiments is seen in FIG. 10, and Table IX.

TABLE IX

| | mg N-formyl-($\beta$-methyl)-asp—phe—OH/shell phase | |
| --- | --- | --- |
| Time (min.) | Exp.1. Dowex 1 present | Exp.2. without Dowex 1. |
| 30 | 31.6 | 30.2 |
| 60 | — | 37.8 |
| 120 | 26.0 | 71.8 |
| 180 | 35.4 | 83.1 |

TABLE IX-continued

| | mg N-formyl-(β-methyl)-asp—phe—OH/shell phase | |
|---|---|---|
| Time (min.) | Exp.1. Dowex 1 present | Exp.2. without Dowex 1. |
| 240 | 45.6 | — |
| 300 | 51.2 | — |

In addition to separating phenylalanine lower alkyl ester copermeating the ion rejection membrane into the product mixture utilizing ion exchange resins as described in this Example, aspartic acid copermeating the ion rejection membrane into the product mixture can be separated utilizing such resins. The species or product that cannot back-diffuse across the membrane from the product mixture can be removed utilizing such ion exchange resins. Also, other separation methods known in the art including but not limited to electrophoresis, electrodialysis and membrane separations which are equivalents of ion exchange resin separations can be utilized in the present invention.

Immobilizing the condensing enzyme allows the enzymatic reaction in the tube phase to be conducted at an initial reaction mixture pH preferred for optimum efficiency of the enzymatic reaction considering the reactants, product(s) and enzyme including the desired equilibrium of the enzymatic reaction. Optionally, the initial reaction mixture pH in the tube phase can be readjusted to a second reaction mixture pH prior to contact with the membrane so that the second reaction mixture pH will maximize the membrane efficiency in transporting the uncharged product from the tube phase across the membrane into the shell phase. FIG. 9 does not show adjusting the initial reaction mixture pH in the tube phase to a second reaction mixture pH.

Similarly, the esterase in the shell phase can be immobilized and the pH of the product mixture in the shell phase can be adjusted and readjusted as necessary to effect the most efficient processing. Examples 8 and 9 provide additional means for efficient continuous or batch processing utilizing the present invention. In continuous processing the desired enantiomer of reactants and any copermeating compounds can be returned to the tube phase or reaction mixture.

EXAMPLE 10

The dipeptide N-formyl-(β-methyl)-asp-phe-OH synthesized in Example 5 was reacted with L-trp-OMe, in the presence of pepsin, to yield the protected tripeptide N-formyl-(β-methyl)-asp-phe-trp-OMe. After permeation, the protected tripeptide was irreversibly hydrolyzed by the enzyme aminoacylase, to yield N-formyl-(β-methyl)-asp-phe-trp-OH.

To a solution of 2.04 g (8 mmoles) L-trp-OMe and 0.484 g pepsin in 250 mL 0.1M citrate buffer pH 4.5, was added 0.642 g (2.1 mmoles) N-formyl-(β-methyl)-asp-phe-OH dissolved in 25 mL absolute MeOH, and the clear 10% MeOH solution resulted was incubated at room temperature for one hour. HPLC analysis at this point indicated the presence of 144 mg/L of the tripeptide N-formyl-β-methyl)-asp-phe-trp-OMe. The solution was then connected to the tube side of an experimental hollow-fiber separator (Bend Research, Inc.), that provided 0.5 ft² (450 cm²) of a ILM made of 50% N,N-diethyldodecanamide in dodecane. The shell side of the separator was connected to the product vessel containing 0.160 g of the enzyme aminoacylase AMANO (AMANO Pharmaceutical Co., Nagoya, Japan) dissolved in 250 mL 10% MeOH at pH 6.0. The two phases were circulated countercurrently at 25° C. at the rates of 50 mL/min. (tube phase) and 250 mL/min. (shell phase) with the assistance of two peristaltic pumps (FIG. 2). The shell phase was kept at pH 6.0 constant through out the run by the use of a pH stat, with 0.5N NaOH as titrant.

Throughout the experiment, the concentration of N-formyl-β-methyl)-asp-phe-OH in the reaction vessel (tube side) was kept approximately constant by the continuous addition of this reactant at the rate of 0.5 mmole/hr. (0.8 g in 5 hrs.), to compensate for its rate of permeation at pH 4.5, in an effort to maintain constant the pepsin-catalyzed velocity of proteosynthesis synthesis during the run.

The formation of the intermediate N-formyl-(β-methyl)-asp-phe-trp-OMe and its product of hydrolysis was monitored by HPLC, using a TRACOR 995 isochromatographic pump together with an LDC Spectro Monitor II (1202) detector, set at 254 nm. The column used was a NOVA-PAK $C_{18}$ cartridge (8 mm I.D.×10 cm) housed in a Millipore Waters RCM-100 Radial Compression Module. The mobile phases used for the analysis were:

A. N-formyl-(β-methyl)-asp-phe-trp-OMe. A v/v mixture of 40% $CH_3CN$ and 60% 0.1% $KH_2PO_4$ buffer solution containing 0.1% triethylamine v/v, adjusted to pH 4.2, was utilized. Retention time was 12.6 minutes (1 mL/min. flow rate).

B. N-formyl-(β-methyl)-asp-phe-trp-OH. A v/v mixture of 30% $CH_3CN$ and 70% 0.1% $KN_2PO_4$ buffer solution containing 0.1% triethylamine v/v, adjusted to pH 4.2, was utilized. Retention time was 10.2 minutes (1 mL/min. flow rate). The data relating to the formation of the tripeptide N-formyl-(β-methyl)-asp-phe-trp-OH is reproduced in Table X below, and is expressed as mg tripeptide accumulated per liter shell phase as a function to time.

Figure 11:
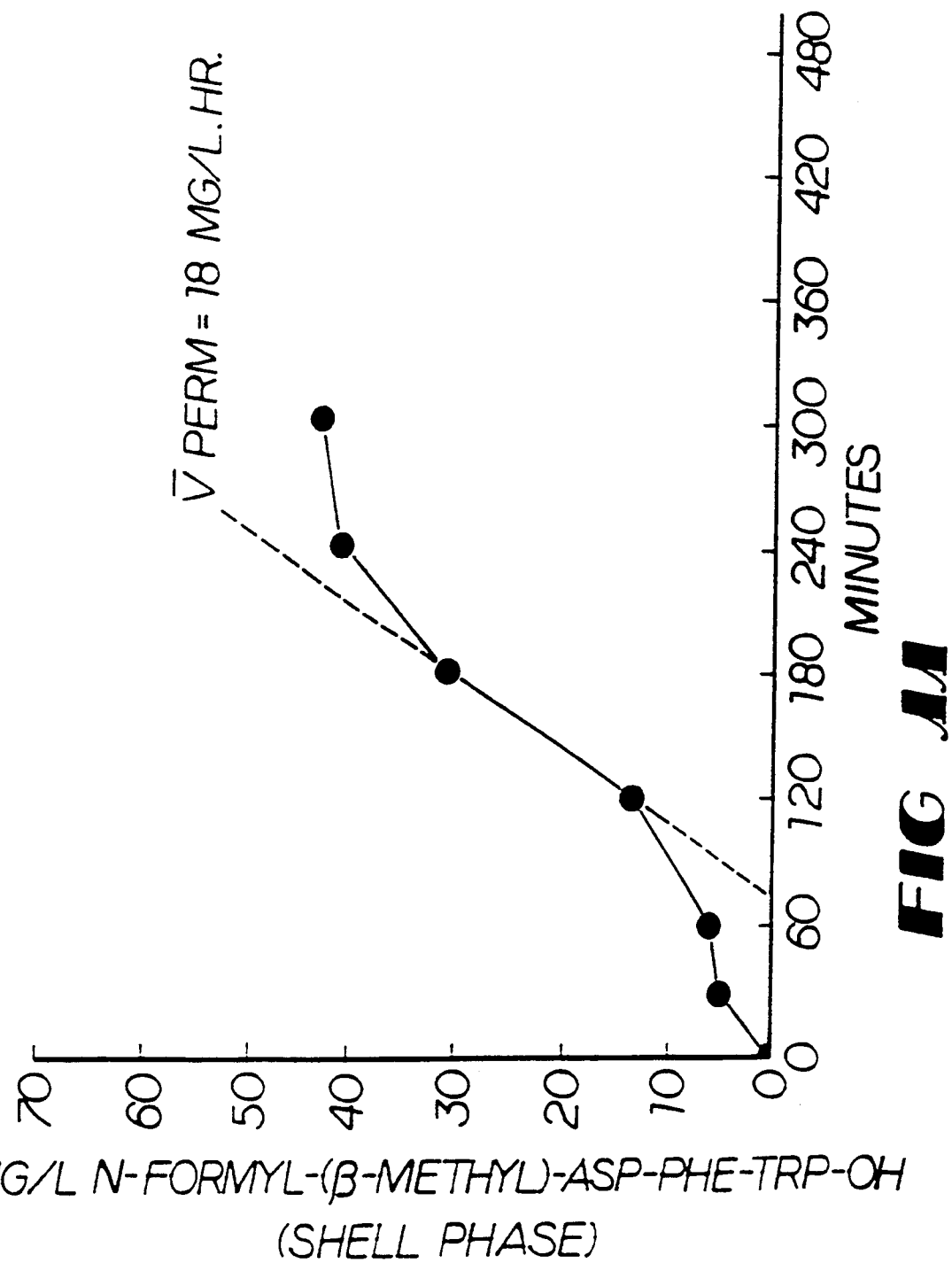
FIG. 11 describes the pepsin catalyzed proteosynthesis of N-formyl-(β-methyl)-asp-phe-trp-OH over time.

A plot of the data is shown in FIG. 11.

TABLE X

| Time (min) | N-formyl-(β-methyl)-asp—phe—trp—OMe (mg/L, tube phase) | N-formyl-(β-methyl)-asp—phe—trp—OH (mg/L, shell phase) |
|---|---|---|
| 0 | 39.6 | 0.0 |
| 30 | | 2.8 |
| 60 | | 5.8 |
| 120 | | 13.7 |
| 180 | | 31.3 |
| 240 | | 40.7 |
| 300 | 50.4 | 42.8 |
| | + Δ = 10.8 mg | + Δ = 42.8 |

Peptide synthesized: 10.8 + 42.8 = 53.6 mg

Figure 12:
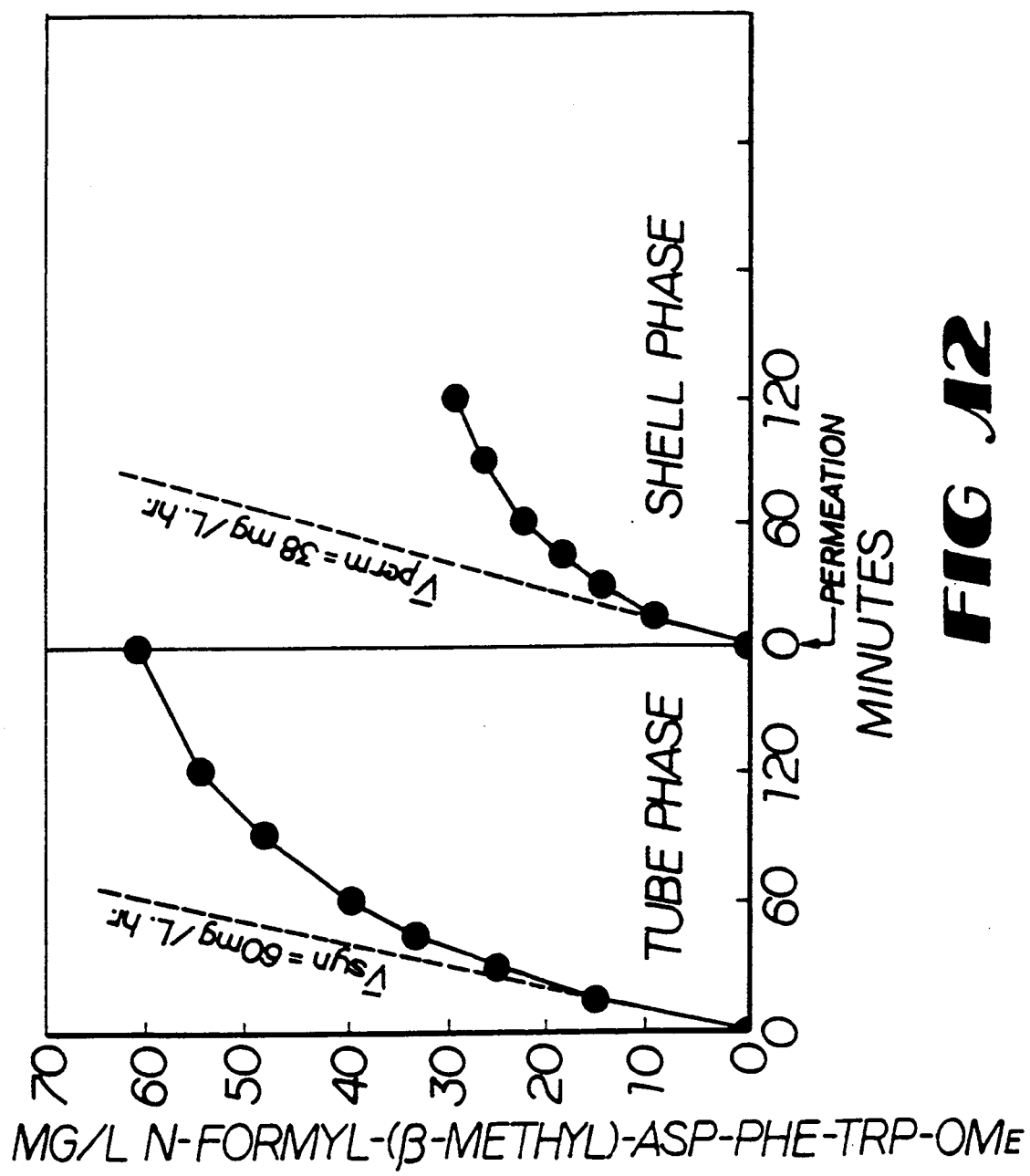
FIG. 12 compares the $V_{syn}$ and $V_{perm}$ for the pepsin catalyzed proteosynthesis of N-formyl-(β-methyl)-asp-phe-trp-OMe.

The hourly averaged rate is $\frac{53.6}{5}$ = 10.7 mg/L. hr., a value of the same order of magnitude as the average rate of a pepsin-catalyzed batch proteosynthesis (FIG. 12).

Identification of the product was done by the comparison of retention times in the above HPLC system, against an authentic sample of N-formyl-(β-methyl)-asp-phe-trp-OH prepared by chemical synthesis as follows:

A. Synthesis of N-formyl-(β-methyl)-asp-phe-trp-OMe. To a solution of 406 mg (1.6 mmoles) L-trp-OMe.HCl (Aldrich) and 0.23 mL (1.7 mmoles) $(Et)_3N$ in 50 mL dioxane was added 500 mg (1.6 mmoles) N-formyl-(β-methyl)-asp-phe-OH, prepared as indicated in Example 5. The solution was immersed in a ice bath, and 350 mg dicyclohexylcarbodiimide (Aldrich) plus 275 mg N-hydroxy-5-norbornene-2,3-dicarboximide (Aldrich) was added to the cold dioxane solution. After stirring for 15 minutes in the ice bath, the solution was left overnight at room temperature. Next morning, the precipitated dicyclohexylurea was filtered off, the dioxane evaporated and the residue dissolved in 200 mL EtOAc, washed with 200 mL 4% citric acid, NaHCO$_3$, water and dried over anh. Na$_2$SO$_4$. Removal of the solvent gave a colorless residue, that was crystallized from EtOAc/hexane to give 630 mg yield) of N-formyl-($\beta$-methyl)-asp-phe-trp-OMe, m.p. 153°–154° C. [$\alpha$]$_D^{22}$ = −35.4° (c=0.8, MeOH). Analysis: Calculated for C$_{27}$H$_{29}$N$_4$O$_7$: C, 62.22; H, 5.56; N, 10.74. Found: C, 61.95; H, 5.85; N, 10.72. $^{13}$C-NMR spectrum confirmed the structure.

B. Synthesis of N-formyl-($\beta$-methyl)-asp-phe-trp-OH. One gram (1.9 mmoles) N-formyl-($\beta$-methyl)-asp-phe-trp-OMe was dissolved in 150 mL MeOH, and the solution added to a solution of 203 mg aminoacylase AMANO 1350 mL water adjusted to pH 6.0. The solution was kept at pH 6.0 at room temperature for 6 hrs., using a pH stat and 0.2N NaOH as titrant. The course of hydrolysis of the C-terminal methyl ester was monitored by HPLC using the conditions described before.

The N-formyl-($\beta$-methyl)-asp-phe-trp-OH formed was extracted with EtOAc at pH 2. Evaporation of the solvent gave a clear residue, that was crystallized from EtOAc/hexane to yield 475 mg (49%) of a white crystalline solid, m.p. 155°–158° C. [$\alpha$]$_D^{22}$ = −30.2° (c, 1.19; MeOH).

Analysis. Calculated for C$_{26}$H$_{27}$N$_4$O$_7$: C, 61.53; H, 5.36; N, 11.04. Found: C, 60.31; H, 5.62; N, 10.66. $^{13}$C-NMR spectrum confirmed the structure.

Under the HPLC conditions described above, the peptide N-formyl-($\beta$-methyl)-asp-phe-trp-OH had a retention time of 10.2 min., identical (alone or in admixture) to the product formed in the pepsin-catalyzed reaction.

EXAMPLE 11

Independent proof that the rate of accumulation of N-formyl-($\beta$-methyl)-asp-phe-trp-OH (V$_{perm}$) observed in Example 10 is solely determined by the rate of pepsin proteosynthesis (V$_{syn}$), is given in the following experiment.

A. Batch proteosynthesis of N-formyl-($\beta$-methyl)-asp-phe-trp-OMe. Comparison of V$_{syn}$ and V$_{perm}$. 1.02 g L-trp-OMe (4 mmoles) and 242 mg pepsin were dissolved in 125 mL of 0.1M citrate buffer pH 4.5, and to this was added 324 mg (1 mmole) N-formyl-($\beta$-methyl)-asp-phe-OH dissolved in 12 mL methanol. The resulting 10% MeOH solution was incubated for 3 hours at room temperature, and the rate of synthesis of N-formyl-($\beta$-methyl)-asp-phe-trp-OMe was followed by HPLC, as described in Example 10. After the 3 hours of reaction, the solution was circulated in a hollow fiber separator with 0.5ft$^2$ ILM of N,N-diethyldodecanamide in dodecane, against 150 mL MeOH in 0.1M citrate buffer pH 5.0. The course of permeation of N-formyl-($\beta$-methyl)-asp-phe-trp-OMe was followed by HPLC, as described before. The data, shown in Table XI and FIG. 12, indicates that the rate of permeation of intermediate tripeptide methyl ester follows closely the rate of proteosynthesis catalyzed by pepsin, measured in a batch reaction without transport.

TABLE XI

| Time (min) | N-formyl-($\beta$-methyl)-asp—phe—trp—OMe (mg/L) |
|---|---|
| 15 | 14.9 |
| 30 | 24.7 |
| 45 | 33.5 |
| 60 | 39.6 |
| 90 | 48.0 |
| 120 | 54.5 |
| 180 | 61.0 |
| Start permeation across ILM 50% N,N-diethyldodecanamide in dodecane | |
| 15 | 9.2 |
| 30 | 14.3 |
| 45 | 18.4 |
| 60 | 22.1 |
| 90 | 25.8 |
| 120 | 29.5 |

B. Rate of permeation of N-formyl-($\beta$-methyl)-asp-phe-trp-OMe under synchronous proteosynthesis, in the absence of aminoacylase. A confirmatory experiment to the one described in Example 10 was done in the absence of aminoacylase during which V$_{perm}$ was measured under synchronous synthesis of tripeptide methyl ester intermediate.

2.04 g L-trp-OMe (8 moles) and 484 mg pepsin were dissolved in 225 mL of 0.1M citrate buffer pH 4.5, and to this was added 642 mg (2 mmoles) of N-formyl-($\beta$-methyl)-asp-phe-OH dissolved in 25 mL MeOH. The solution was left overnight at room temperature, after which HPLC analysis indicated the presence of 167.4 mg/L of N-formyl-($\beta$-methyl)-asp-phe-trp-OMe at equilibrium. The solution was circulated through the tube side of a hollow fiber separator with Celgard fibers containing 1 ft$^2$ ILM of 50% v/v N,N-diethyl dodecanamide in dodecane, countercurrently against a shell phase of 250 mL 10% MeOH in 0.1M citrate buffer pH 5.0. The permeation of the intermediate tripeptide methyl ester into the shell phase was followed by HPLC, as described in Example 10. The corresponding data is tabulated in Table XII, and plotted in FIG. 13.

TABLE XII

| | N-formyl-($\beta$-methyl)-asp—phe—trp—OMe | |
|---|---|---|
| Time (min) | Reaction phase (mg/L) | Product phase (mg/L) |
| 0 | 167.4 | 0.0 |
| 15 | 204.9 | 8.6 |
| 30 | 192.4 | 22.3 |
| 45 | 183.0 | 29.8 |
| 60 | 204.2 | 37.6 |
| 120 | 182.6 | 59.1 |
| 180 | 177.3 | 73.1 |
| 240 | 142.8 | 85.4 |
| 300 | 192.4 | 91.4 |
| | + $\Delta$ = 25.0 mg | + $\Delta$ = 91.4 mg |

Total peptide synthesized: 25.0 + 91.4 = 116.4 mg

Per hour rate: $\frac{116.4}{5}$ = 23.3 mg/L. hr.

Figure 13:
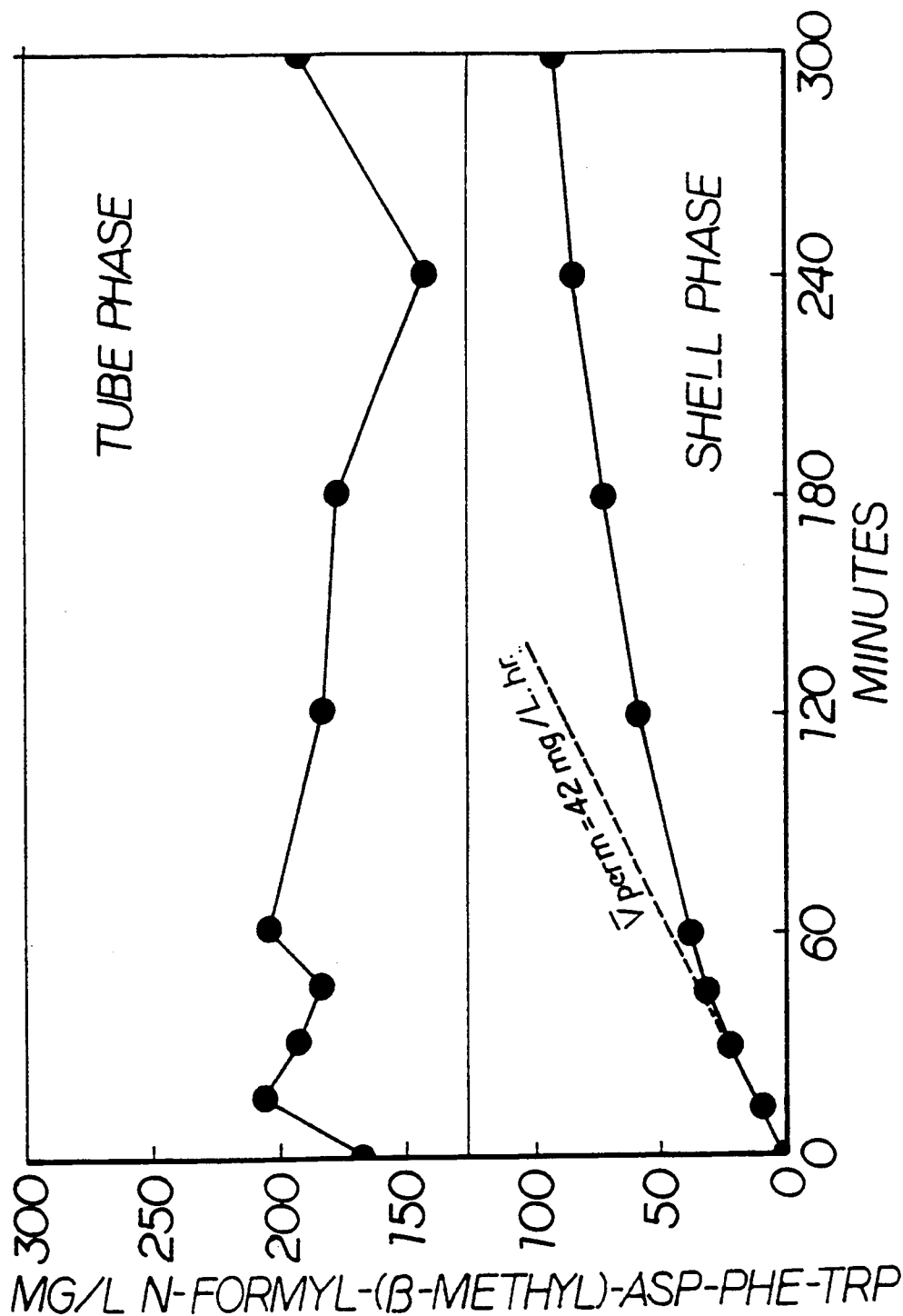
FIG. 13 describes the pepsin catalyzed proteosynthesis of N-formyl-(β-methyl)-asp-phe-trp-OMe over time.

From the comparison of the initial rates of permeation V$_{perm}$ of N-formyl-($\beta$-methyl)-asp-phe-trp-OMe shown in FIG. 12 and FIG. 13, it is obvious that the aminoacylase plays no role in the kinetics of peptide transfer across the ILM, as both rates are similar at about 40 mg/L. hr. ft$^2$. Consequently, the rate-determining step in the permeation experiments of Examples 10 and 11 is the rate of pepsin proteosynthesis, while the role of the aminoacylase is simply to secure the displacement of the equilibrium through the quantitative transfer of intermediate peptide from the reaction to the product phase.

Figure 14:
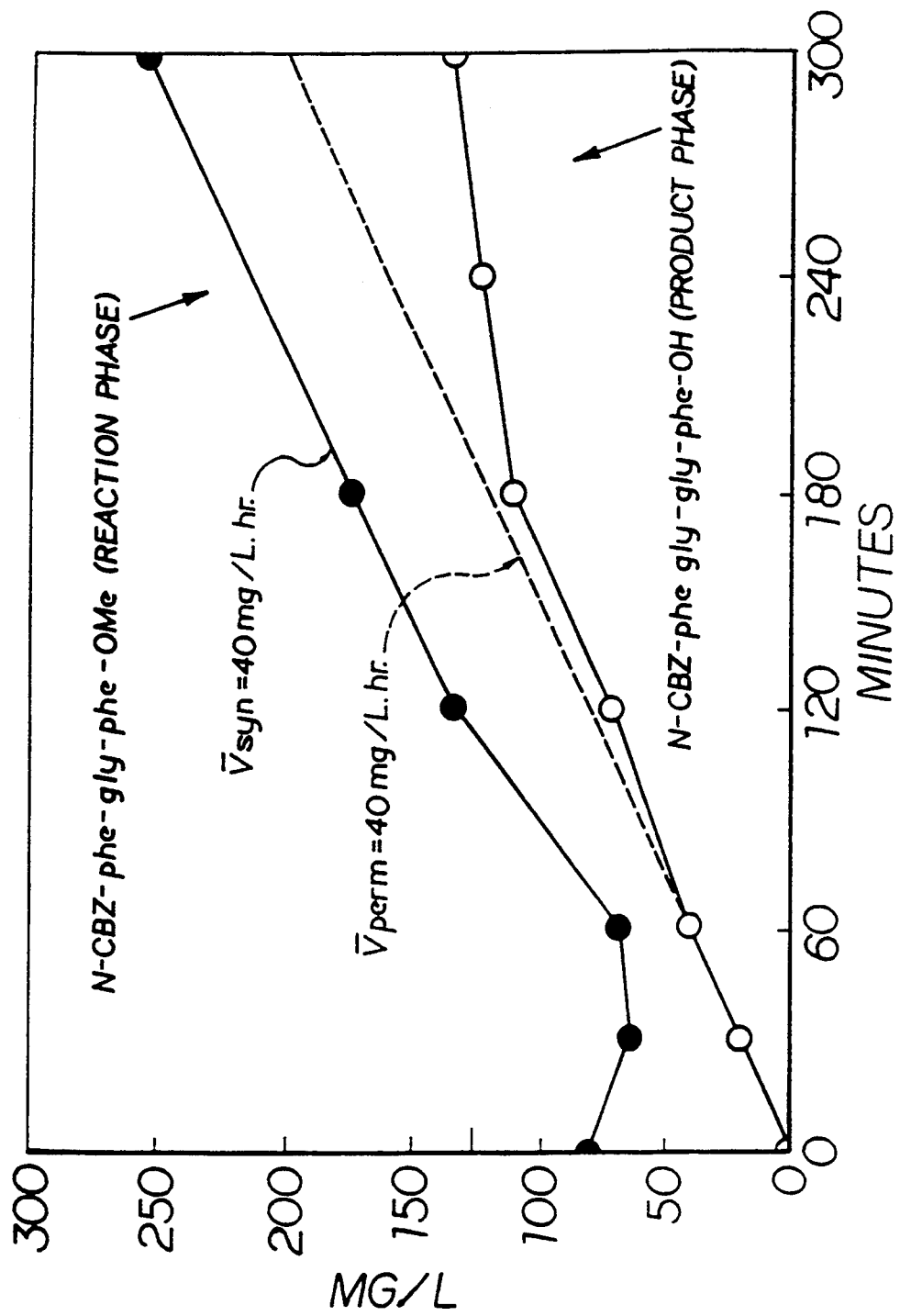
FIG. 14 describes the papain catalyzed proteosynthesis of N-CBZ-phe-gly-gly-phe-OH over time.

The results of this experiment are detailed in Table XIII and FIG. 14.

TABLE XIII

| Time (min) | N—CBZ—phe—gly—gly—phe—OMe Reaction phase (mg/L) | N—CBZ—phe—gly—gly—phe—OH Product phase (mg/L) |
| --- | --- | --- |
| 0 | 78.3 | 0.0 |
| 30 | 64.3 | 19.0 |
| 60 | 69.0 | 41.1 |
| 120 | 133.0 | 72.8 |
| 180 | 174.4 | 107.6 |
| 240 | — | 120.2 |
| 300 | 252.2 | 132.9 |
|  | + Δ = 173.9 mg | + Δ = 132.9 mg |

Synthesized peptide: 306.8 mg

Hourly rate: $\frac{306.8}{5} = 61.4$ mg/L. hr.

On the other hand, physical factors affecting the permeability of the intermediate peptide through the ILM, like the relative solubility oil/water phase (partition coefficient), membrane composition and temperature, will determine the steady-state concentration of peptide intermediate in the reactor during continuous operations.

EXAMPLE 12

This example demonstrates the feasibility of the proteosynthesis of a tetrapeptide, achieved through the papain-catalyzed coupling of two dipeptides.

To a solution of 1084 mg (4 mmoles) of H-gly-phe-OMe.HCl in 112 mL McIlvaine buffer pH 6.0 was added a solution of 20 mg papain plus 0.5 mL 2-mercaptoethanol in 20 mL of the same buffer. After the addition of 356 mg (1 mmole) of N-CBZ-phe-gly-OH dissolved in 15 mL methanol, the resulting solution (10% MeOH, buffer pH 6.0) was incubated for 1 hour at room temperature. HPLC analysis at this point indicated the presence of 78.3 mg/L N-CBZ-phe-glygly-phe-OMe. This solution was circulated through the tube side of a hollow fiber separator made of Celgard hollow fibers, containing 0.5 ft$^2$ of a ILM of 50% v/v N,N-diethyl-dodecanamide in dodecane. The shell phase (150 mL, 10% MeOH, pH 6.0) was unbuffered and contained. dissolved 80 mg aminoacylase AMANO. It was circulated countercurrently through the separator at room temperature, and the pH was kept constant at 6.0 with the help of a pH-stat, using 0.5N NaOH as titrant. The synthesis of N-CBZ-phe-gly-gly-phe-OMe in the reaction phase (tube) and the accumulation of N-CBZ-phe-gly-gly-phe-OH in the product (shell) phase were followed by HPLC analysis, using a Perkin-Elmer System consisting of a 410 LC Pump, LC 235 Diode Array detector set at 210 run and a LCI-100 Laboratory Computing Integrator for data analysis. The analytical column chosen was a NOVA-PAK C$_{18}$ cartridge (8 mm×10 cm, 4μ) housed in a Millipore/Waters RCM-100 radial compression unit. The mobile phase was a v/v mixture of 50% CH$_3$CN and 50% 0.1% KH$_2$PO$_4$ buffer solution containing triethylamine v/v, adjusted to pH 4.2—flow rate was 1 mL/min. Retention times for the N-CBZ-phe-gly-gly-phe-OMe and N-CBZ-phe-gly-gly-phe-OH were 7.05 minutes and 4.16 minutes, respectively.

In an effort to compensate for the permeation losses of H-gly-phe-OMe at pH 6.0, this reactant was continuously added to the reaction phase during the 5-hour run, at the rate of 0–5 mmole/hr. (total 680 mg).

Figure 15:
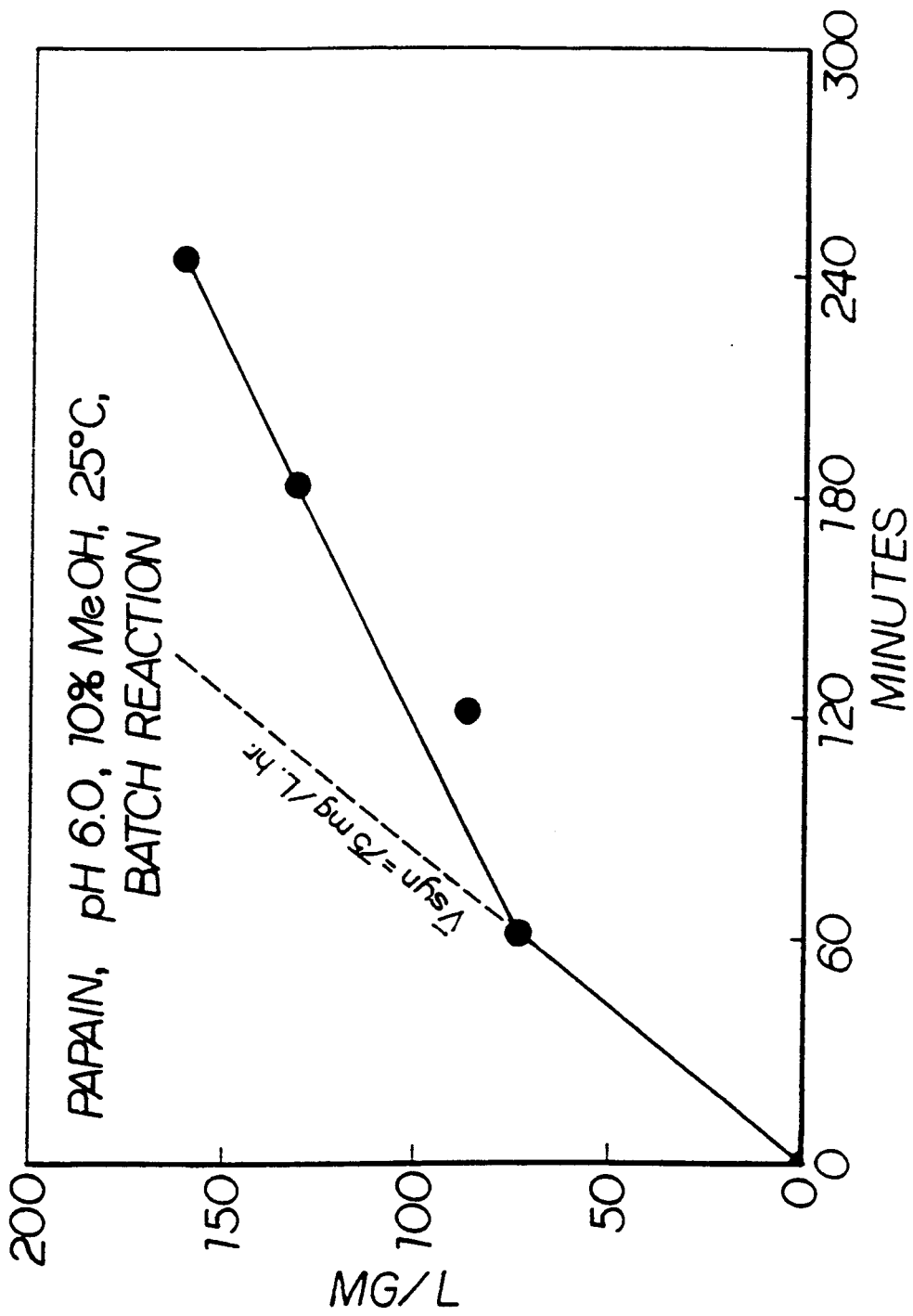
FIG. 15 describes the rate of synthesis of N-CBZ-phe-gly-gly-phe-OMe.

This rate value corresponds to the value $V_{syn}=75$ mg/L.hr. found in a batch papain-catalyzed proteolysis (FIG. 15), proving again that the rate of accumulation of product reflects the rate of proteosynthesis in the reaction phase. This is quite evident in the FIG. 14, where the $V_{perm}=V_{syn}=40$ mg/L/hr.

Identification of the product accumulated in the shell phase was done by HPLC comparison against an authentic sample of N-CBZ-phe-gly-gly-phe-OH prepared as follows:

A. Synthesis of N-CBZ-phe-gly-gly-phe-OMe. To a solution of 500 mg (1.8 moles) of H-gly-phe-OMe. HCl 50 mL was added 0.4 mL (1.9 mmoles) Et$_3$N, the solution immersed in an ice bath, followed by the addition of 640 mg (1.8 mmoles) N-CBZ-phe-gly-OH, 280 mg of dicyclohexylcarbodiimide and 220 mg of N-hydroxy-5-norbornene-2,3-dicarboximide.

The mixture was allowed to react overnight at room temperature, after which the precipitated dicyclohexylurea was filtered off, the dioxane removed by evaporation to yield a colorless residue. The crude product was dissolved in 200 mL EtOAc, washed with 200 mL each of 5% citric acid, 5% NaHC$_3$, prior to drying over anh. Na$_2$SO$_4$. Removal of the solvent gave 720 mg of a clear glassy residue, that crystallized from EtOAc/hexane to yield 600 mg (58%) of N-CBZ-phe-gly-gly-phe-OMe, white crystals, m.p. 85°-86° C., $[\alpha]_D^{22}=0.0°$ (c, 1.0; MeOH). Analysis. Calculated for C$_{31}$H$_{34}$N$_4$O$_7$: C, 64.79; H, 5.96; N, 9.75, Found: C, 64.23; H, 6.05; N, 9.66. $^{13}$C-NMR spectrum substantiated the structure.

B. Synthesis of N-CBZ-phe-gly-gly-phe-OH. To a solution of 100 mg aminoacylase AMANO in 90 mL deionized water pH 6.0, was added a solution of 400 mg (0.7 mmoles) of N-CBZ-phe-gly-gly-phe-OMe in 20 mL methanol. The milky-white mixture was rapidly stirred at room temperature, and began to clear almost immediately. The mixture was allowed to react for one hour, keeping pH 6.0 constant with the use of a pH-stat and 0.1N NaOH as titrant. At this point, HPLC analysis indicated that the ester hydrolysis was completed. The reaction mixture was filtered, the filtrate stripped of methanol in vacuo, acidified to pH 2.0 and extracted with EtOAc (3×200 mL). The organic extract was dried over anh. Na$_2$SO$_4$, and the solvent evaporated to yield 300 mg of a clear residue. Crystallization from EtOAc/hexane gave 220 mg (60%) of N-CBZ-phe-gly-gly-phe-OH, white crystals, m.p. 134°-136° C.; $[\alpha]_D^{22}= +6.8°$ (c 1.74; MeOH). Analysis. Calc,d for C$_{30}$H$_{32}$N$_4$O$_7$: C, 64.27; H, 5.75; N, 9.99. Found: C, 63.83; H, 5.80; N, 9.88. $^{13}$C-NMR and $^1$H-NMR spectra substantiated the structure.

HPLC analysis under the conditions described above indicated the presence of only one compound of retention time 4.16 minutes, alone or mixed with the product of papain-catalyzed proteosynthesis.

EXAMPLE 13

Papain-catalyzed proteosynthesis of a derivative of the pentapeptide [leu]$^5$-enkephalin To a solution of 21 mg papain in 160 mL McIlvaine buffer pH 6.0, containing 0.5 mL 2-mercaptoethanol, was added a solution of 363 mg (1 mmole) N-formyl-(O-Bzl)-tyr-gly-OH and 361 mg (1 mmole) gly-phe-leu-OMe in 40 mL methanol. After a brief standing (15 minutes) at room temperature, HPLC analysis indicated the presence of 3.2 mg/L of N-formyl-(O-Bzl)-tyr-gly-gly-phe-leu-OMe already formed. The solution (reaction phase) was then connected to the shell side of a hollow-fiber separator (Bend Research, Inc.), fitted with Celgard fibers containing a 1 ft$^2$ ILM of 50% v/v N,N-diethyldodecanamide in dodecane. The product phase was a solution of 158 mg aminoacylase AMANO in 200 mL 20% MeOH, adjusted to pH 6.0, that was connected to the tube side of the separator. The two phases were circulated countercurrently at 25° C., with the assistance of two peristaltic pumps. The product phase (tube side) was kept at pH 6.0 throughout the run with the help of a pH-stat, using 0.5N NaOH as titrant.

Throughout the experiment, the concentration of the reactant H-gly-phe-leu-OMe in the reaction phase was held approximately constant, by adding an additional 1.284 g (4 mmoles) dissolved in 12 mL methanol, at the rate of mmole/hr to compensate for permeation losses. The formation of the intermediate N-formyl-(O-Bzl)-tyr-gly-gly-phe-leu-OMe and its hydrolysis product N-formyl-(O-Bzl)-tyr-gly-gly-phe-leu-OH was monitored by HPLC, using the instrumentation described in Example 12. The solvent systems used were as follows:

A. N-formyl-(O-Bzl)-tyr-gly-gly-phe-leu-OMe: A v/v mixture of 60% CH$_3$CN and 40% 0.1% KH$_2$PO$_4$ buffer solution containing 0.1% v/v Et$_3$N, adjusted to pH 4.2. Retention time was 5.01 minutes.

B. N-formyl(O-Bzl)-tyr-gly-gly-phe-leu-OH: A v/v mixture of 30% CH$_3$CN and 70% 0.1% KH$_2$PO$_4$ buffer solution containing 0.1% v/v Et$_3$N, adjusted to pH 4.2 was utilized. Retention time was 7.07 minutes.

Figure 16:
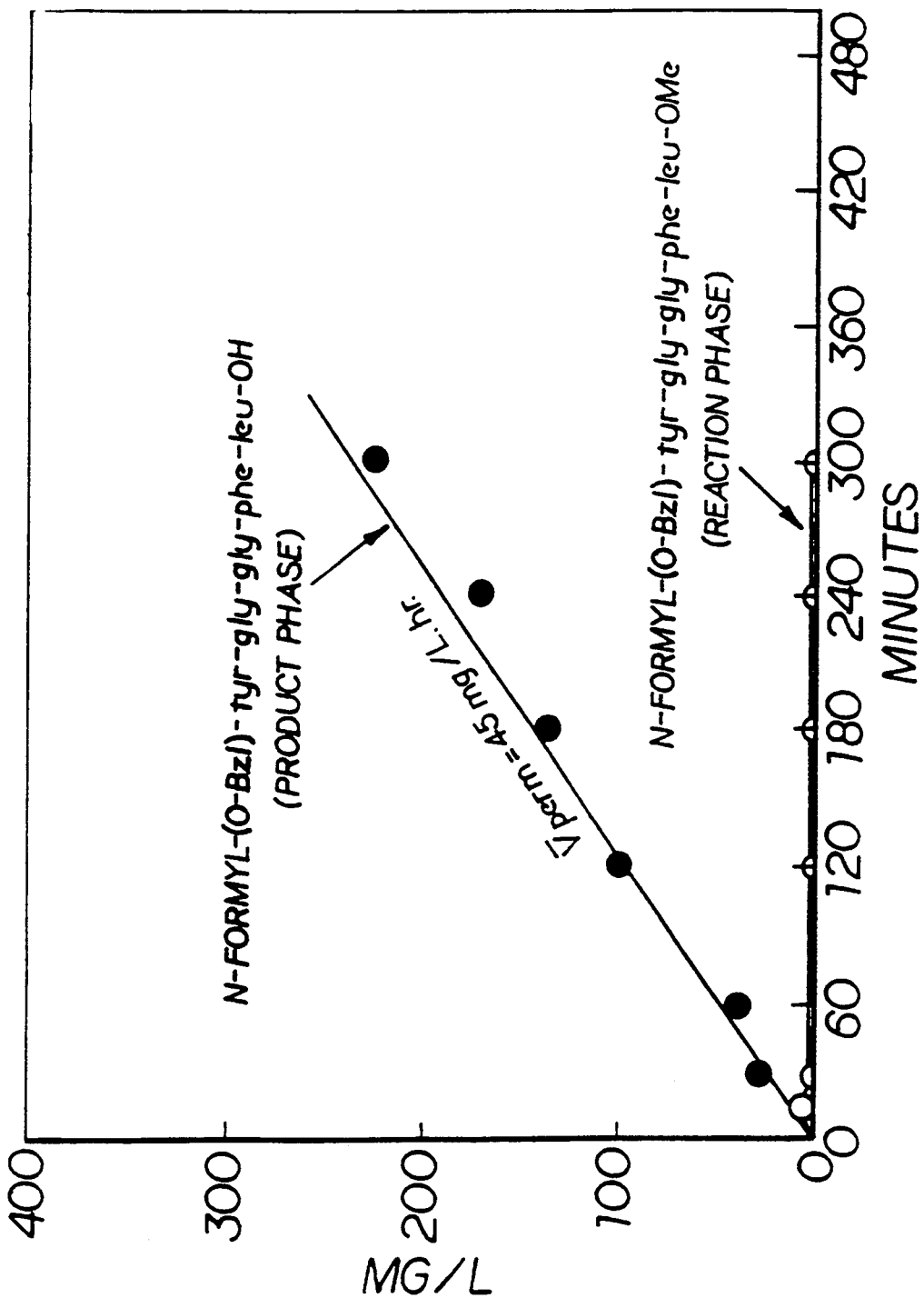
FIG. 16 describes the papain-catalyzed proteosynthesis of N-formyl-(O-Bzl)-tyr-gly-gly-phe-leu-OH.

The data showing the build up of hydrolyzed pentapeptide in the product phase is shown in Table XIV, and plotted in FIG. 16.

TABLE XIV

| Time (min) | N-formyl-(O—Bzl)-tyr—gly—gly—phe—leu—OMe (Reaction phase, mg/L) | N-formyl-(O—Bzl)-tyr—gly—gly—phe—leu—OH (Product phase, mg/L) |
| --- | --- | --- |
| 0 | 3.2 | 0.0 |
| 30 | 5.4 | 30.7 |
| 60 | 0.7 | 39.0 |
| 120 | 1.0 | 101.4 |
| 180 | 0.9 | 136.9 |
| 240 | 1.0 | 174.4 |
| 300 | 1.2 | 227.0 |

As experienced in previous examples, the average hourly rate of pentapeptide formation (FIG. 16, $\overline{V}_{perm}$=45 mg/L. hr) was in agreement with the rate of N-formyl-(O-Bzl)-tyr-gly-gly-phe-leu-OMe synthesis measured in a parallel batch incubation of N-formyl-(O-Bzl)-tyr-gly-OH and H-gly-phe-leu-OMe with papain at pH 6.0, and found to be $V_{syn}$=34.2 mg/L/hr. at 25° C.

The product phase (200 mL) was adjusted to pH 2 and extracted twice with 200 mL EtOAc each. The organic extract was evaporated to dryness and the residue, containing N-formyl-(O-Bzl)-tyr-gly-gly-phe-leu-OH and N-formyl-(O-Bzl)-tyr-gly-OH (HPLC), was redissolved in 10 mL EtOAc and introduced into a Ito Multilayer Coil Separator-Extractor, already filled with a stationary phase of 400 mL 0.01M phosphate buffer pH 5.4. The separation by countercurrent distribution was done with 400 ML of EtOAc saturated with 0.01M phosphate buffer pH 5.4; 20 fractions 20 mL each of the EtOAc phase were collected. HPLC analysis indicated the presence of the pentapeptide acid in fractions 3–10, and the dipeptide acid in fractions 16–18. The presence of N-formyl-(O-Bzl)-[leu]$^5$-enkephalin in the pooled 3–10 fractions was confirmed through deprotection with 1 NHCl at 50° C. to remove the formyl group, followed by hydrogenation over Pd/charcoal to remove the benzyl group. The product was found identical to H-tyr-gly-gly-phe-leu-OH by HPLC comparison with an authentic sample of synthetic [leu]$^5$-enkephalin acetate salt (Sigma Chemical Catalog, 1988, catalog number L-9133, p. 280).

EXAMPLE 14

Use of cellulose hollow-fiber contactors to support hydrophobic liquids—Application to proteosynthesis The thermolysin-catalyzed proteosynthesis described in Example 5 was practiced with equal success in a membrane contactor embodiment, comprising packed cellulose hollow fibers having their lumens filled with a hydrophobic liquid and their walls embedded in water. Forced countercurrent circulation of the tube phase between two membrane modules in series provides a high surface contactor, able to transfer uncharged organic molecules between an aqueous reaction phase and an aqueous phase. This arrangement, useful for the practice of proteosynthesis according to this invention, is sketched in FIG. 17. Circulation by a first pump 64 of the aqueous reaction phase 63 from the thermolysin reactor 61 to the first membrane module 67 allows for the transfer of the permeable intermediate N-formyl-($\beta$-methyl)-asp-phe-OMe into the hydrophobic phase (oil) reservoir 65 via descending oil line 81. This enriched oil is circulated from the hydrophobic phase reservoir 65 via transfer line 82 by a second pump 66 via pump line 83 into the second membrane module 68, where the intermediate dipeptide ester diffuses out into an aqueous product phase 80 in a product reservoir 69. The intermediate dipeptide ester is circulated to a membrane separator such as a reverse osmosis membrane RO 62 by a third pump 70. The intermediate dipeptide ester is irreversibly trapped by the reverse osmosis membrane RO 62 in the rententate 77. The filtrate 78 from the RO 62 is returned 73 the product reservoir 69. The retentate 77 from the RO 62 is recycled 79 to the product reservoir 69. The pure water 71 leaving the RO unit is returned to the second membrane module 68, while the spent oil leaving the second membrane module 68 is recycled via line 72 into the first membrane module 67, where it gets reloaded with fresh intermediate produced by proteosynthesis in the reaction vessel 61. The oil loop 84 (water-immiscible hydrophobic phase) comprises hydrophobic phase reservoir 65 and line 82, pump 66, oil line 83, line 72 and line 81 comprising first contactor 67, second contactor 68, RO 62, aqueous reaction phase 63, aqueous product phase 80 and oil loop 84, thus closing the cycle. A first membrane contactor 74 is shown. The process can be enhanced by utilizing a second membrane contactor 75 (not shown, but identical to 74) utilizing a bleedstream 76. Generally, a plurality of membrane contactors can be utilized repeatedly to enhance recovery of product.

Figure 27:
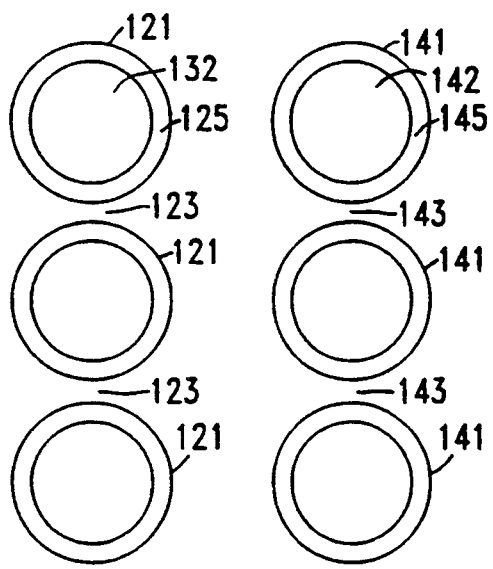
FIG. 27 is a partial schematic view (enlarged) of a cross section of hollow fibers in a membrane contactor.

FIG. 27 is a partial schematic view (enlarged) of a cross section of hollow fibers in a membrane contactor. The partial view shows hydrophilic hollow fibers 121 in a first membrane module and hydrophilic hollow fibers 141 in a second membrane module. In the first membrane module hydrophilic hollow fibers 121 are shown having a lumen (bore) 122 and hydrophilic polymeric material 125. The lumen 122 is filled with water-immiscible organic liquid comprising the tube phase (e.g., hydrophobic phase). The space 123 between the hydrophilic hollow fibers 121 comprises the shell phase (e.g., aqueous reaction phase). Similarly, in the second membrane module hydrophilic hollow fibers 141 are shown having a lumen (bore) 142 and hydrophilic polymeric material 145. The lumen 142 is filled with water-immiscible organic liquid comprising the tube phase (e.g., hydrophobic phase). The space 143 between the hydrophilic hollow fibers 141 comprises the shell phase (e.g., aqueous reaction phase).

Figure 28:
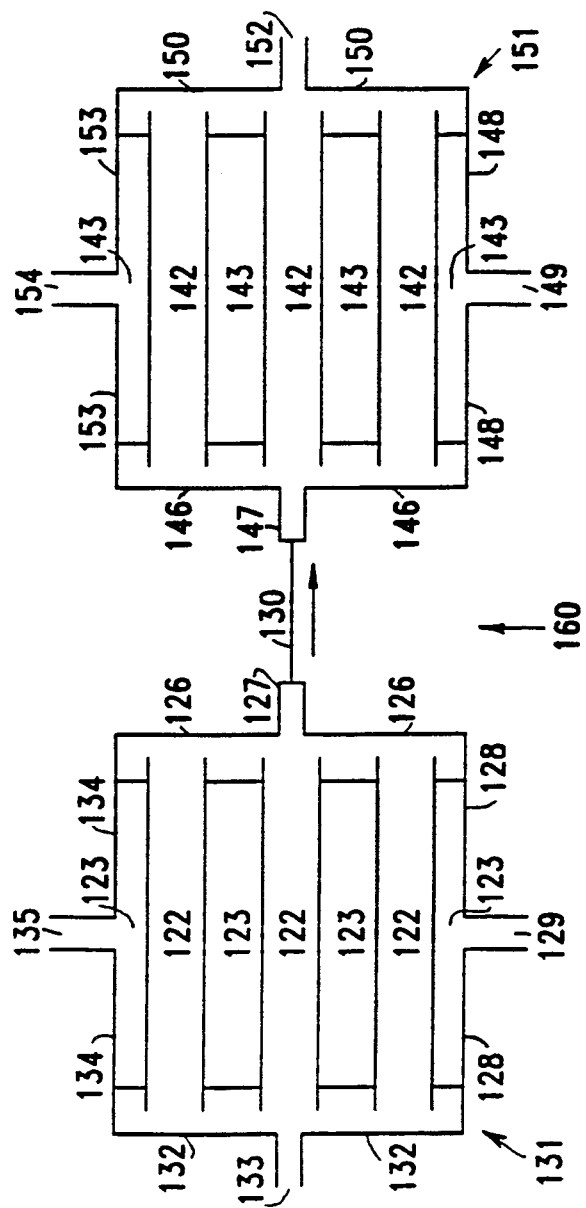
FIG. 28 is a partial schematic view (enlarged) of a membrane contactor.

FIG. 28 is a partial schematic view (enlarged) of a membrane contactor 160 comprising a first membrane module 131, a second membrane module 151 and a connecting means (tube) 130. In the first membrane module 131 hydrophilic hollow fibers 121 are potted in a resinous material (potting compound). The aqueous reaction phase is circulated through space 123, through opening 129 on first wall 128 and returned through opening 135 on third wall 134. The aqueous reaction phase does not mix with the water-immiscible liquid. The water-immiscible liquid is circulated through lumen 121, through opening 127 on the second wall 126 to the second membrane module 151 through connecting tube 130 and returned to the first membrane module 131 through opening 133 on the fourth wall 132. Similarly, in the second membrane 151 hydrophilic hollow fibers 141 are potted in a resinous material (potting compound). The aqueous product phase is circulated through space 143, through opening 149 on first wall 148 and returned through opening 154 on third wall 153. The aqueous product phase does not mix with the water-immiscible liquid. The water immiscible liquid is circulated from connecting tube 130 through opening 147 on fourth wall 146 through lumen 142 and returned to the first membrane module 131 through opening 152 on second wall 150. The first and second membrane modules, 131 and 151, of the membrane contactor 160 each comprise many hydrophilic hollow fibers, 121 and 141, respectively, although only three are shown in each such membrane module.

The use of membrane contactors in conjunction with reverse osmosis as described will cause the desired displacement of the proteosynthetic equilibrium, without affecting the kinetics of peptide synthesis in the thermolysin reactor. This approach is considered as a viable alternative to the use of a second enzyme for the purpose of driving the proteosynthesis to completion. Using this membrane arrangement, an experiment was conducted in which the enzyme thermolysin catalyzed the coupling of N-formyl-($\beta$-methyl)-H-phe-OMe(A) and asp-OH (B), and the resulting peptide N-formyl-($\beta$-methyl)-asp-phe-OMe(C) was continually trapped in the RO retentate (FIG. 17). The conditions used in this experiment were as follows:

A. Thermolysin reactor. 300 mL, pH 5.0, 50° C., [B]=340 mM, [A]=627 mM, [thermolysin]=21 g/L, [CaCl$_2$]=10 mM. The initial rate of C synthesis under these conditions was V$_{syn}$=13 g/L.hr (37.5 mM/hr).

B. Membrane contactor. 0.8 ft$^2$, loaded with 2-undecanone.

C. RO Membrane. 2 ft$^2$ TW-30 spiral-wound module. Manufactured by FilmTec Corporation, Minnetonka, Minn., (polyamide type membranes as described in U.S. Pat. No. 4,277,344)

D. Product reservoir. 700 mL, pH 5.0, 50° C.

Figure 18:
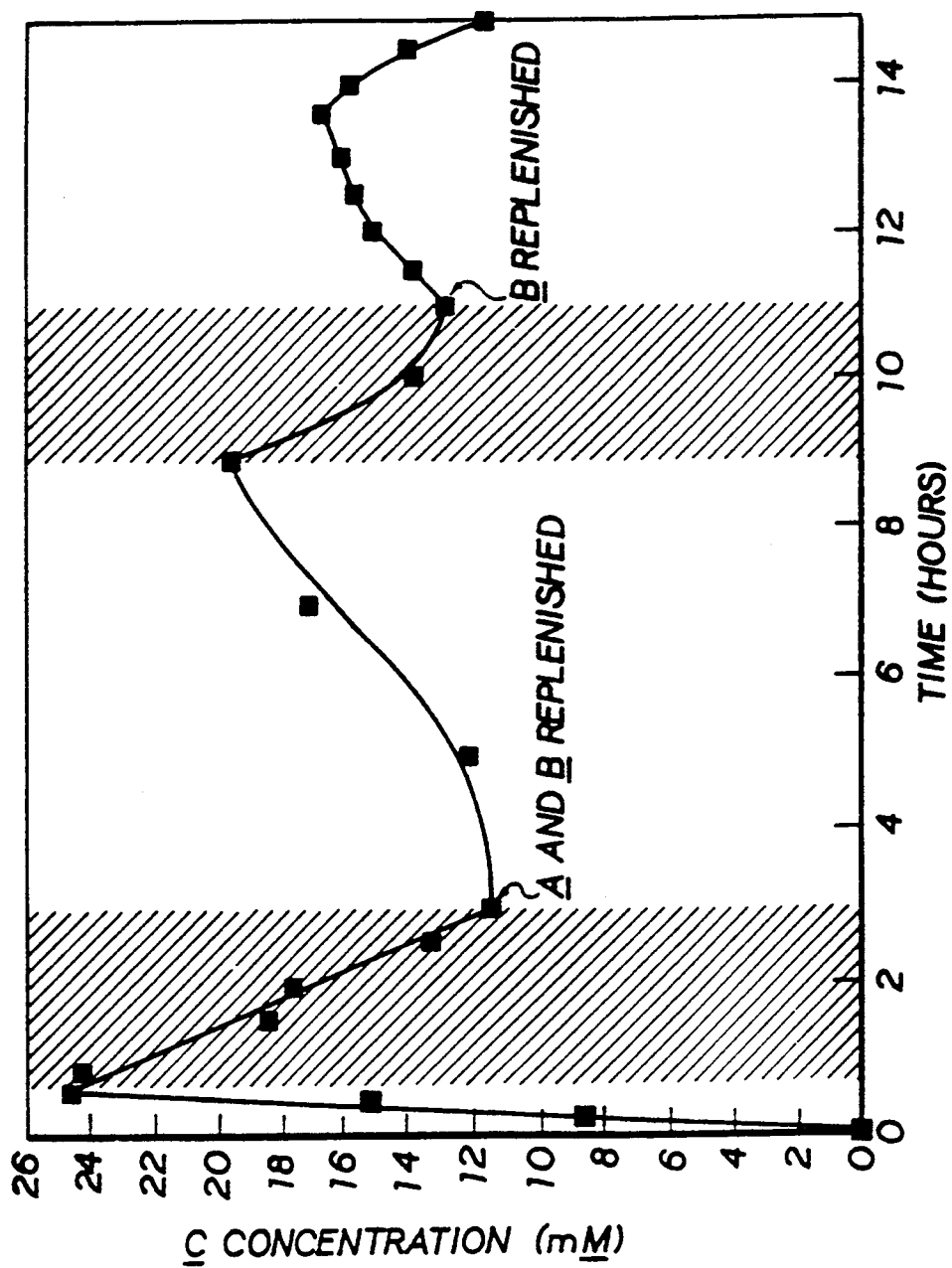
FIG. 18 describes the concentration of C in the thermolysin reactor during the long-term run.

The results from the operation of the first stage of this run are shown in FIG. 18, which plots the concentration of C in the thermolysin reactor as a function of time. The data clearly shows the continuous removal of C from the reactor by the membrane contactor, and the recovery of the chemical equilibrium upon stopping the flow of undecanone and the simultaneous addition of enough A and B to restore the original reactant concentrations. The system was run for 15 hours, at which time the concentrations of A and C in the product reservoir were 40 mM and 15 mM, respectively. (A:C molar ratio=3:1). This product solution was concentrated about 10-fold using a combination of RO and evaporation. The concentrate (100 mL), containing 5.0 g A and 3.59 g C in the solution at pH 4.0, was then placed in the feed reservoir of the membrane-contactor system, and the system was operated at 25° C. against 100 mL water, pH 4.0 placed in the product reservoir (FIG. 17), until approximately 50% of C had been removed from the feed solution. The product from this second stage, which contained about 0.6 g A and 1.8 g C (A:C molar ratio=2:3), was evaporated down to 25 mL and chilled, to yield 1.64 g (81%) pure C, white crystals m.p. 105°-107° C. [α]$_D^{25}$=−32.3° (c, 0.65; MeOH). An authentic sample of N-formyl-($\beta$-methyl)-asp-phe-OMe had m.p. 108°-109° C. [α]$_D^{25}$=−33.9° c, 0.59; MeOH). Based on the optical rotation, the purity of the recovered dipeptide C was 95%.

EXAMPLE 15

This example describes the thermolysin-catalyzed proteosynthesis of the dipeptide N-formyl-($\beta$-methyl)-asp-phe-O-<, and its synchronous hydrolysis to the acidic dipeptide N-formyl-($\beta$-methyl)-asp-phe-OH, across an ILM including N,N-diethyldodecanamide. The symbol "-<" is utilized herein to indicate isopropyl.

To a solution of 13.09 g (54 mmoles) of L-phe-O-<.HCl and 6.64 g (38 mmoles) of N-formyl-($\beta$-methyl)-asp-OH in 200 mL water at pH 5.0, was added 385 mg of thermolysin (Thermoase, Daiwa, 40,000 PU/g) and 150 mg CaCl$_2$. The solution was incubated at 25° C. for one hour at which time it was found by HPLC analysis to contain 148.9 mg/L of the dipeptide N-formyl-($\beta$-methyl)-asp-phe-O-<. The solution was then connected to the shell side of an experimental hollow-fiber separator (Bend Research, Inc.), that provided 1 ft$^2$ (900 cm2) surface of an ILM of N,N-diethyldodecanamide. The tube side of the separator was connected to the product vessel containing a solution of 0.162 g of the enzyme aminoacylase (AMANO Pharmaceutical Co., Nagoya, Japan) dissolved in 200 mL water at pH 6.0. The two phases were circulated countercurrently at 25° C. at the rates of 100 mL/min (tube phase) and 250 mL/min (shell phase), with the assistance of two centrifugal pumps (FIG. 2). The product (tube) phase was kept at pH 6.0 constant, by using a pH stat with 0.5N NaOH as titrant.

The formation of the intermediate and product peptides was monitored by HPLC, using a Perkin-Elmer System consisting of a 410 LC Pump, LC 235 Diode Array detector set at 210 nm, and a LCI-100 Laboratory Computing Integrator for data analysis. The analytical column chosen was a NOVA-PAK $C_{18}$ cartridge (8 mm×10 cm, 4µ) housed in a Millipore/Waters RCM-100 radial compression unit. The mobile phase for the N-formyl-($\beta$-methyl)-asp-phe-O-< was a v/v mixture of $CH_3CN$ and 50% 0.1% $KH_2PO_4$ buffer solution containing 0.1% v/v triethylamine, adjusted to pH 4.2. Flow rate was 1 mL/min. Retention time was 5.65 minutes. The mobile phase for the N-formyl-($\beta$-methyl)-asp-phe-OH was a v/v mixture of 30% $CH_3CN$ and 70% 0.1% $KH_2PO_4$ buffer solution containing 0.1% v/v triethylamine, adjusted to pH 4.2. Flow rate: 1 mL/min. Retention time: 3.52 minutes.

Figure 19:
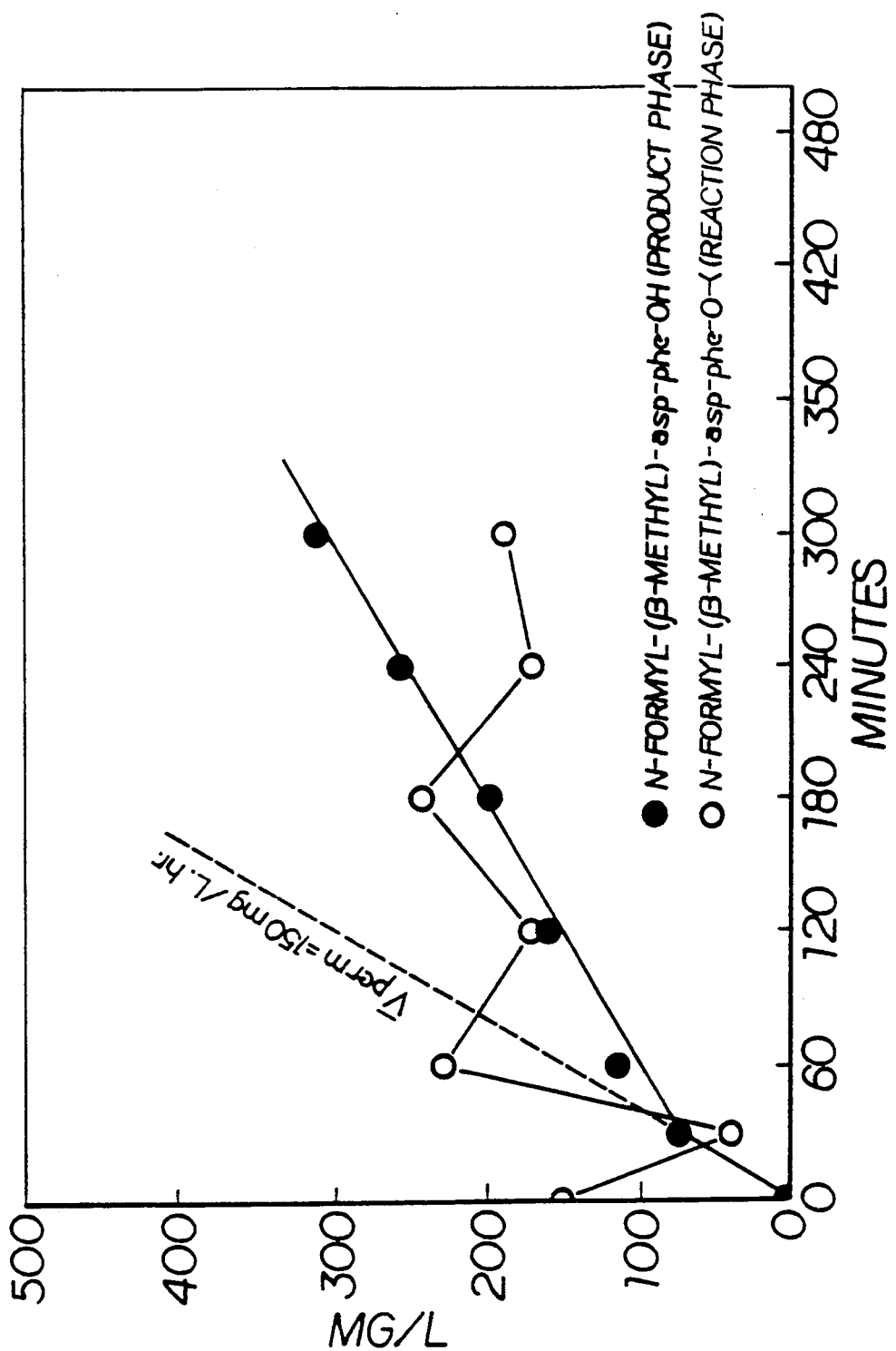
FIG. 19 describes the thermolysin-catalyzed proteosynthesis of N-formyl-($\beta$-methyl)-asp-phe-OH.

The results of this experiment are shown in Table XV and FIG. 19.

TABLE XV

| Time (min) phase, mg/L | N-formyl-($\beta$-methyl)-asp—phe—O—< (Reaction phase, mg/L) | N-formyl-($\beta$-methyl)-asp—phe—OH (Product phase, mg/L) |
|---|---|---|
| 0 | 148.9 | 0 |
| 30 | 41.1 | 75.8 |
| 60 | 228.9 | 115.7 |
| 120 | 172.8 | 163.3 |
| 180 | 246.2 | 199.1 |
| 240 | 172.8 | 262.1 |
| 300 | 192.7 | 314.8 |
| | + Δ = 43.8 mg | + Δ = 314.8 mg |

Synthesized dipeptide: 358.6 mg/L.
Hourly rate = $\frac{358.6}{5}$ = 72 mg/L/hr.

Figure 20:
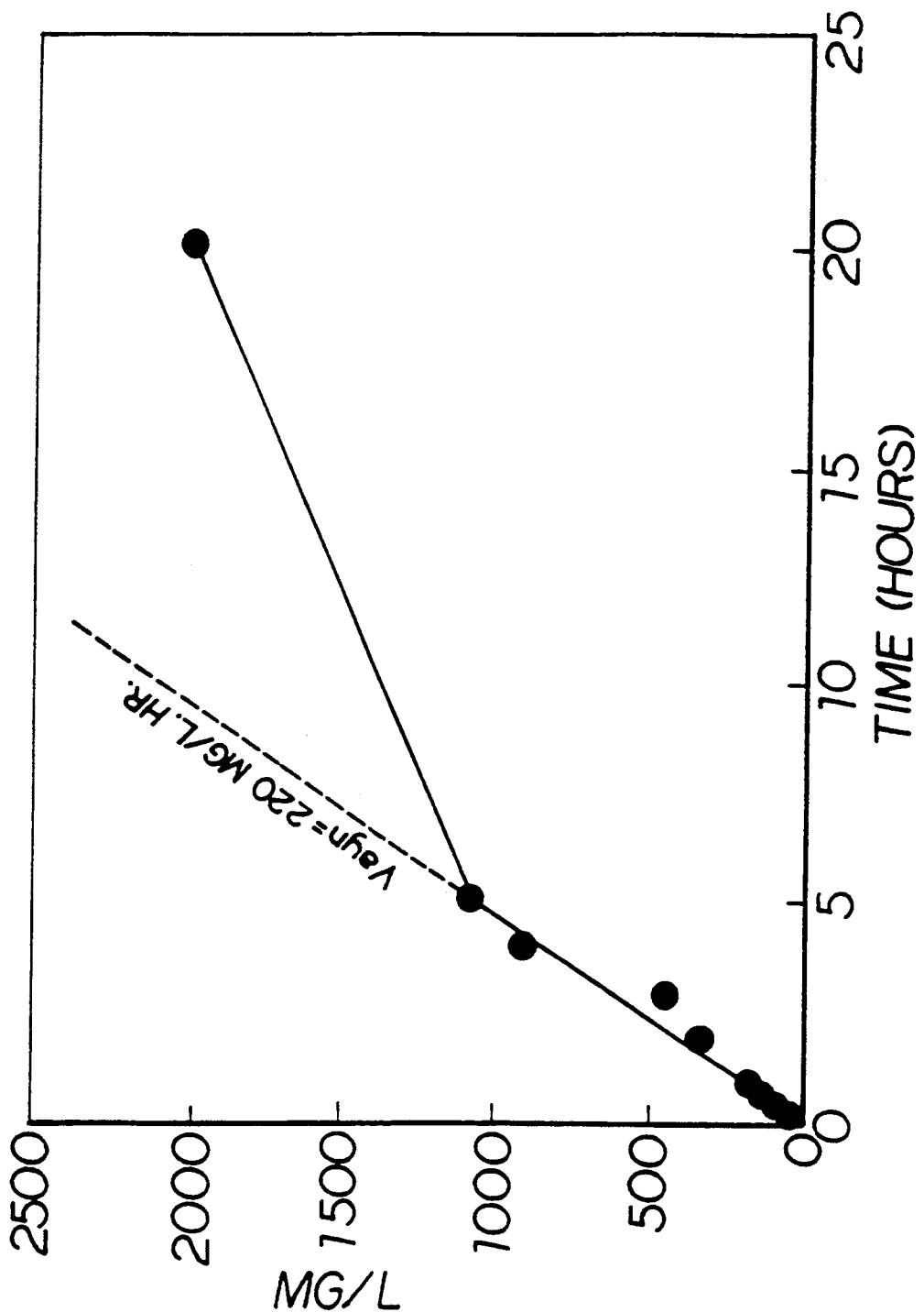
FIG. 20 describes the kinetics of synthesis of N-formyl-($\beta$-methyl)-asp-phe-O-<.

This overall hourly rate is in line with the initial permeation rate of 150 mg/L. hr measured at the first hour (FIG. 19), and with the initial synthesis rate of 220 mg/L/hr. measured independently for a batch incubation (FIG. 20) run at the same conditions of pH, temperature and reagent concentrations, The dipeptide acid N-formyl-($\beta$-methyl)-asp-phe-OH present in the 200 mL product phase (63 mg) was isolated by concentrating the solution in vacuo to 50 mL, removal of the enzyme by ultrafiltration over an Amicom PM-10 membrane (molecular weight cut-off: 10 Kdalton), acidification of the ultrafiltrate to pH 2.0 and extraction with EtOAc (3×50 mL). The organic extract was evaporated to dryness, the residue dissolved in 2 mL water pH 6.0, and the dipeptide was crystallized by acidification to pH 2.0. Yield: 11 mg (17%), identical by HPLC comparison to an authentic sample of N-formyl-($\beta$-methyl) -asp-phe-OH prepared according to the following procedure.

A. Synthesis of N-formyl-($\beta$-methyl)-asp-phe-OMe. To 21.0 g (97.3 mmoles) L-phe-OMe.HCl dissolved in 300 mL dioxane was added 14.9 mL (107 mmoles) $Et_3N$. To this mixture was added 16.0 g (98 mmoles) N-formyl-($\beta$-methyl)-asp-OH, the solution was cooled to 0° C., and 20.0 g (97 mmoles) dicyclohexylcarbodiimide were added, followed by 16.0 g N-hydroxy-5-norbornene-2,3-dicarboximide. After stirring overnight at room temperature, the dicyclohexylurea precipitated was filtered off, and the filtrate concentrated to a syrup by evaporation. It was dissolved in 500 mL EtOAc, and washed sequentially with 5% citric acid, 5% $NaHC_3$, water, and dried over anhydrous $Na_2SO_4$. Removal of the solvent gave a white solid, which was recrystallized twice from EtOAc/hexane to yield 17.0 g (53%) of N-formyl-($\beta$-methyl)-asp-phe-OMe, m.p. 108°–109° C. $[\alpha]_D^{25°} = -36.9°$ (c=0.6, MeOH).

$^1$H-NMR ($CD_3OD$): 7.6 δ (s) formyl; 6.8 δ (s) phenyl; 4.0–4.4 δ0 (M) 2 CH; 3.3 δ0 (s) 2 $CH_3$ (6 protons, superimposed); 2.3–2.8 δ0 (M) 2 $CH_2$ (4 protons).

$^{13}$C-NMR ($CDCl_3$): 35.52, 37.56 ppm (—$CH_2$—, t); 47.59, 53.54 ppm (

d); 52.09, 52.28 ppm ($CH_3$—, q); 127.08, 128.51, 129.19 ppm (phenyl, d); 135.62 ppm (phenyl, s); 160.93 ppm (

d); 169.60, 171.34, 172.09 ppm (

(NH), s).

Analysis: Calculated for $C_{16}H_{20}O_6N_2$: C, 57.17; H, 5.95; N, 8.33. Found: C, 57.29; H, 6.02; N, 8.32.

B. Synthesis of N-formyl-($\beta$-methyl)-asp-phe-OH. A solution of 2.0 g (5.9 mmoles) of N-formyl-($\beta$-methyl)-asp-phe-OMe in 50 mL MeOH was added to a solution of 0.2 g aminoacylase AMANO in 450 mL 0.05% $KH_2PO_4$ buffer pH 7.5, contained in a beaker fitted with a mechanical stirrer. The solution was stirred overnight at room temperature, and the pH was kept constant at 7.5 with the assistance of a pH stat, using 1N NaOH as titrant. After filtration of any unreacted starting material, the solution was washed with EtOAc (2×100 mL), then adjusted to pH 2.0 and the hydrolyzed dipeptide was extracted with EtOAc (3×200 mL). The combined extracts were dried over anhydrous $Na_2SO_4$ and evaporated to dryness. The yield of N-formyl-($\beta$-methyl)-asp-phe-OH was 1.3 g (68%), m.p. 185°–186° C. $[\alpha]_D^{25°} = -14.3°$ (c=1.0; MeOH)

$^{13}$C-NMR ($CD_3OD$): 37.37, 38.76 ppm (—$CH_2$—, t); 50.21, 55.68 ppm (—CH—, d); 52.21 ppm ($CH_3$—, q); 128.31, 129.90, 130.90 ppm (phenyl, d); 138.63 ppm (phenyl, s); 163.99 ppm (

, d); 172.38, 172.83, 174.77 ppm (

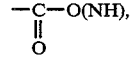

s).

Analysis: Calculated for $C_{15}H_{18}O_6N_2$: C,55.93; H, 5.59; N, 8.69. Found: C,55.22; H, 5.71; N, 8.51.

EXAMPLE 16

This example shows the rate effect caused by the hydrolytic enzyme upon the permeation $V_{perm}$ of the intermediary peptide during synchronous proteosynthesis. The measured rate increase is particularly important for those highly hydrophobic peptides showing high partition coefficients towards the hydrophobic membrane. The chemical transformation catalyzed by the aminoacylase, that is the conversion of a C-terminal isopropyl ester into the free carboxylate, occurs at the interface oil/water and assists positively in the transport of dipeptide across the boundary. The increase in permeation of the intermediary peptide caused by the countercurrent sweeping of the oil surface with the aminoacylase is an additional effect to the equilibrium displacement resulting from the chemical transformation to a non-permeable product.

To a solution of 13.7 g (56 mmoles) of L-phe-O-<.HCl and 6.6 g (38 mmoles) of N-formyl-($\beta$-methyl)-asp-OH in 200 mL water at pH 5.0, was added 397 mg Thermoase Daiwa (40,000 PU/g) and 150 mg $CaCl_2$. The solution was incubated at 25° C. for one hour, at that time it was found by HPLC analysis to contain 347.0 mg/L of the dipeptide N-formyl-($\beta$-methyl)-asp-phe-O-<. The solution was circulated at 25° C. through the shell side of an hollow-fiber separator, containing 0.5 ft² ILM of N,N-diethyldodecanamide, against 200 mL water pH 6.0 circulating countercurrently through the tube side (FIG. 2). The rate of permeation across the ILM was measured for the dipeptide-O-< and L-phe-O-< by HPLC, following the details discussed in Example 15.

Figure 22:
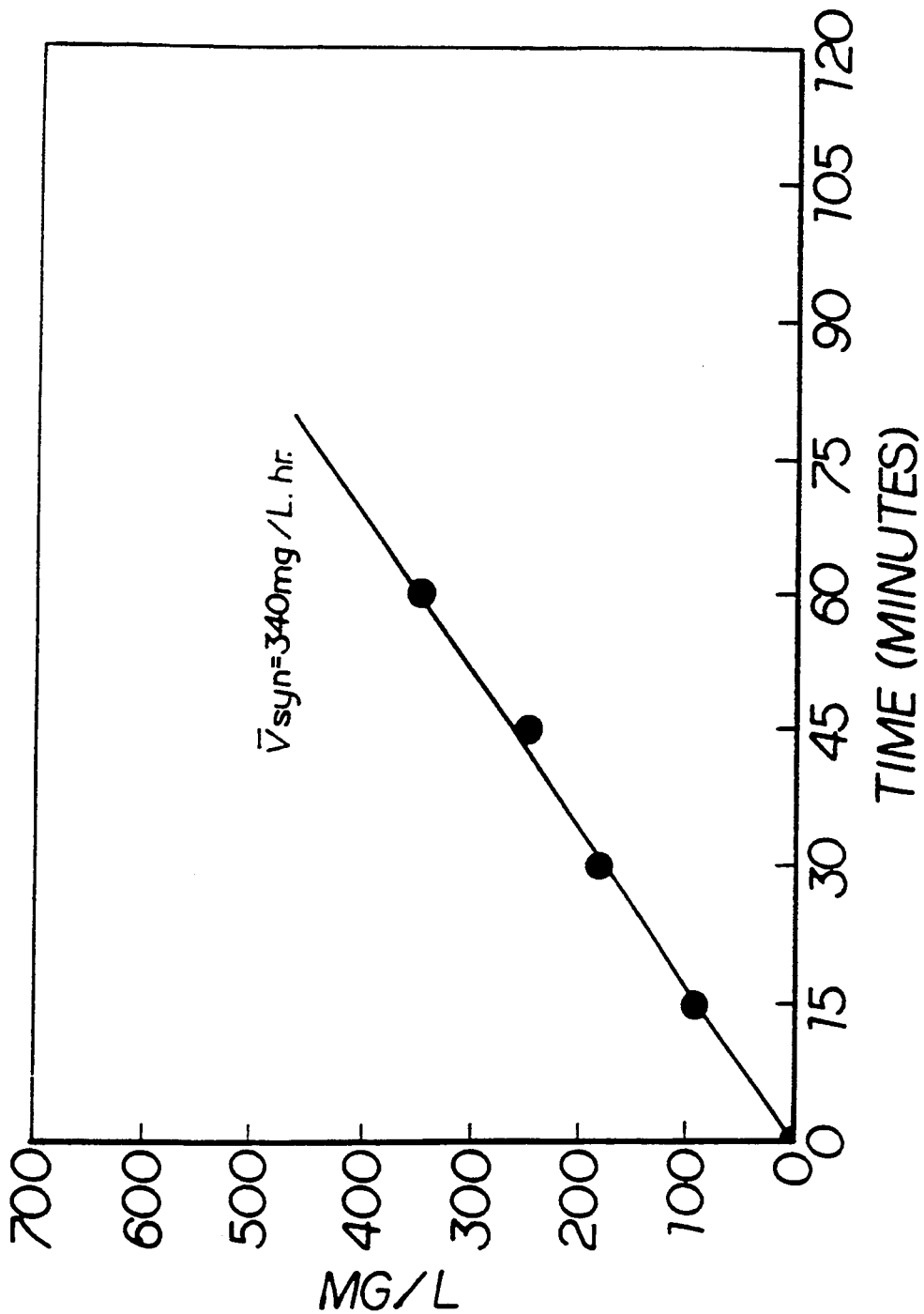
FIG. 22 describes the thermolysin-catalyzed proteosynthesis of N-formyl-($\beta$-methyl)-asp-phe-O-< in a ILM module.

After two hours the circulation was interrupted, the product (tube) phase was removed, and replaced by 200 mL water pH 6.0 containing 160 mg aminoacylase AMANO in solution. The countercurrent circulation of both aqueous phases was reinitiated, and the rate of permeation $V_{perm}$ of the dipeptide N-formyl-($\beta$-methyl)-asp-phe-OH was measured by HPLC again, together with L-phe-OH and L-phe-O-<. The results appear in Table XVI and FIG. 21.

period (FIG. 22), under identical conditions of pH, temperature and reactant concentrations.

It is also shown in Table XVI that the rate effect exerted by the aminoacylase is resulting from the hydrolysis of the dipeptide isopropyl ester. The rate of permeation of L-phe-O-<, a poor substrate for the aminoacylase, is insensitive to the presence of the enzyme in the product phase.

EXAMPLE 17

This Example 17 illustrates the effect of operating the process of this invention at elevated temperatures and effectiveness at higher temperatures in a range of from 20° C. to 65° C. of lower alkyl ester reactants [B'] wherein the alkyl group is selected to enhance stability of that reactant, e.g., esters derived from secondary alcohols having 3 to 6 carbon atoms.

The thermolysin-catalyzed proteosynthesis of the dipeptide N-formyl-($\beta$-methyl)-asp-phe-O-< (C') described in Example 15, was successfully practiced, at 50° C. utilizing the cellulose hollow-fiber contactor described in Example 14, in place of the ILM module used in Example 15.

The set-up used in this experiment is outlined in FIG. 17, and the conditions for achieving the condensation equilibrium between N-formyl-($\beta$-methyl)-asp-OH (B'), L-phe-O-< (A') and the resulting dipeptide C' were as follows:

A. Thermolysin Reactor. 500 ml, pH 5.0, 50° C., containing 42 g/l thermolysin, 10 mM $CaCl_2$, 230 mM B' 450 mM A'.
B. Membrane Contactors. 0.4 ft² of membrane area in each membrane contactor module, with 75 mL of N,N-diethyldodecanamide as the circulating organic oil.
C. RO Membrane. 2 ft² TW-30 spiral-wound module previously described in Example 14.
D. Product Reservoir. 750 mL water, pH 5.0, 50° C., circulating throught the RO module, the membrane contactor and the reservoir.

Figure 23:
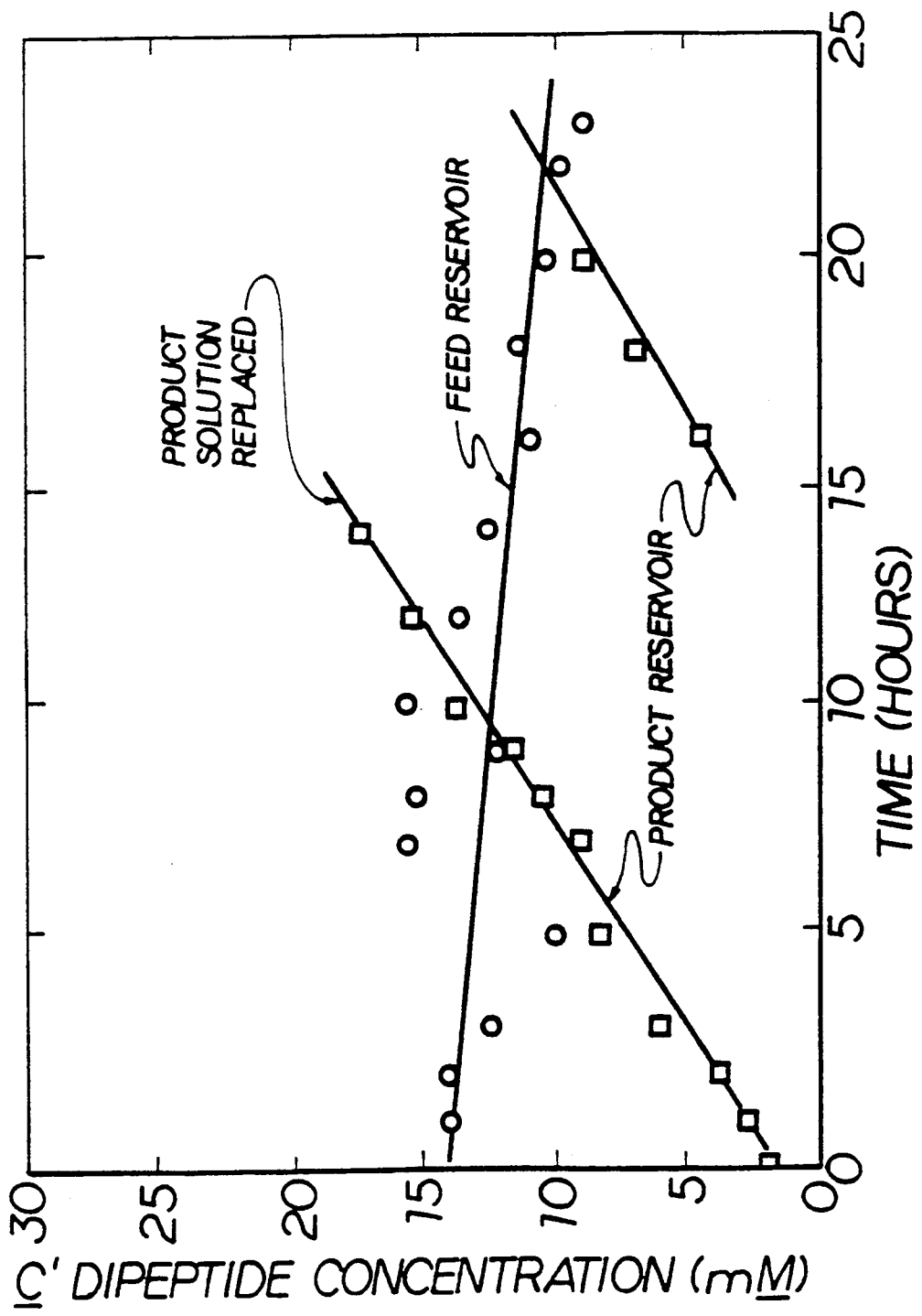
FIG. 23 describes the synthesis of N-formyl-($\beta$-methyl)-L-asp-L-phe-O-< in a membrane contactor.

The accumulation of product C' in the reservoir as a function of time is shown in FIG. 23. The data shows

TABLE XVI

| | REACTION PHASE | PRODUCT PHASE | | | |
|---|---|---|---|---|---|
| Time (min) | N-formyl-($\beta$-methyl)-asp—phe—O-< (mg/L) | N-formyl-($\beta$-methyl)-asp—phe—O-< (mg/L) | L—phe—O-< (mg/L) | N-formyl-($\beta$-methyl)-asp—phe—OH (mg/L) | L—phe—OH (mg/L) |
| Part I: | | | | | |
| 30 | 283.0 | 89.7 | 899.2 | — | — |
| 60 | 245.3 | 120.3 | 1051.5 | — | — |
| 90 | 322.4 | 155.7 | 1813.6 | — | — |
| 120 | 262.8 | 174.6 | 1600.2 | — | — |
| Part II: | | | | | |
| 30 | 248.8 | — | 701.0 | 213.9 | 141.7 |
| 60 | 545.2 | — | 649.2 | 295.4 | 181.6 |
| 90 | 817.7 | — | 1036.3 | 658.3 | 231.8 |
| 120 | 519.2 | — | 1089.6 | 946.9 | 286.6 |

Figure 21:
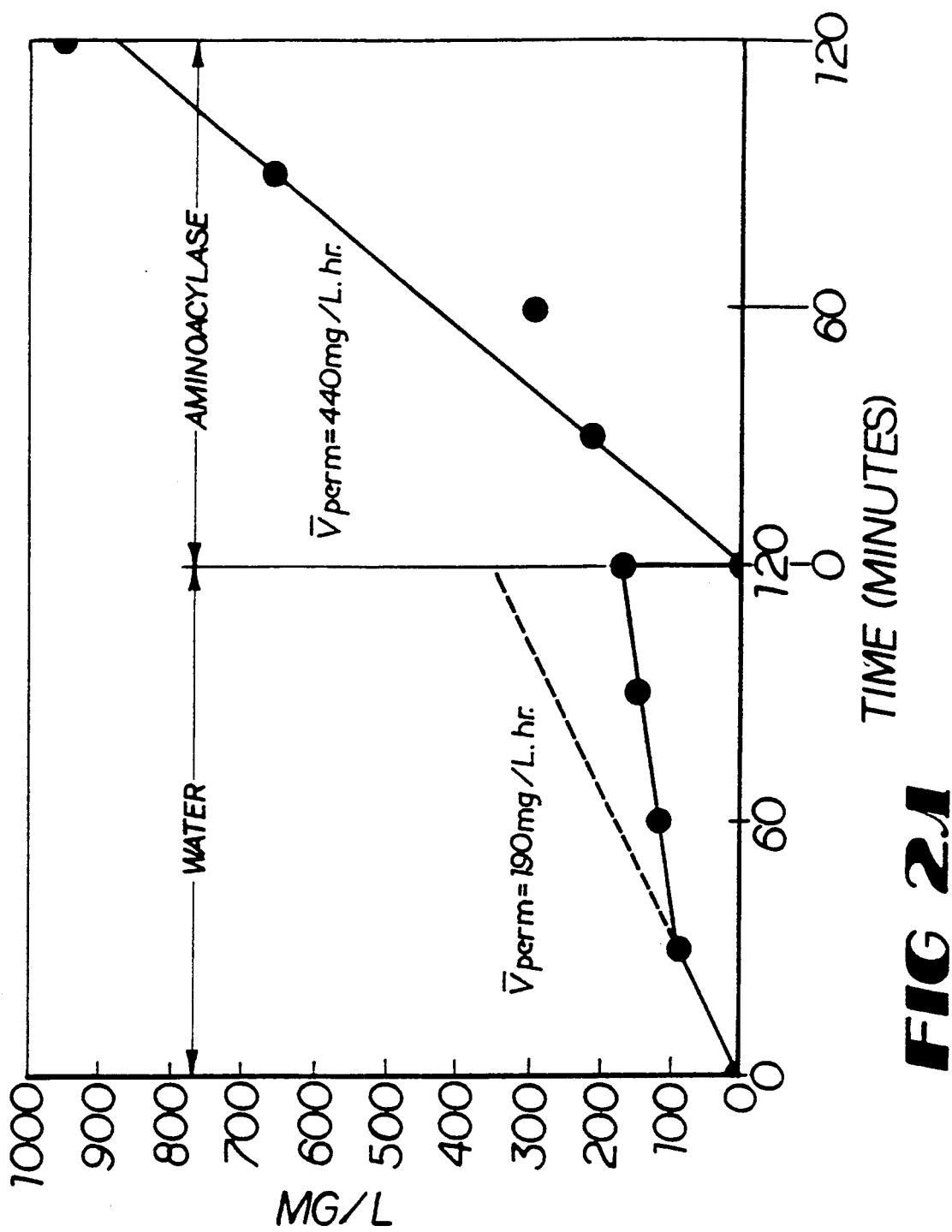
FIG. 21 describes the effect of the enzyme aminoacylase on the rate of permeation of N-formyl-($\beta$-methyl)-asp-phe-O-< across an ILM including N,N-diethyl-dodecanamide.

FIG. 21 shows that the peptide permeation in the presence of aminoacylase ($V_{perm}$=440 mg/L/hr.) is 2.3 times faster than in water ($V_{perm}$=190 mg/L/hr.). This rate effect caused by the direct contact of the ILM with the soluble enzyme would be lost if the same enzyme is used in the immobilized form.

The data also show that only under the "enzyme sweeping" conditions indicated in Part II the proteosynthetic process becomes synchronous, that is, the dipeptide $V_{perm}$ (440 mg/L.hr) reaches the $V_{syn}$ value (340 mg/L.hr) measured during the batch incubation that the concentration of C' in the thermolysin-driven equilibrium is maintained at 15 mM upon addition of A' to keep [A'] constant, while the [C'] in the product reservoir increases steadily as the dipeptide is trapped by the RO membrane, thus providing the constant driving force needed to displace the chemical equilibrium A'+B'⇌C'.

After 15 hours operation the reactor was stopped, and the product solution (20 mM C', 160 mM A') was collected, adjusted to pH2, concentrated 10x by evaporation and cooled, to yield 3.9 g (70% yield) of N-formyl-($\beta$-methyl)-asp-phe-O<, white crystals, m.p. 68°–69° C., $[\alpha]_D^{25°} = -22.7°$ (C, 3.6; MeOH).

Analysis: Calculated for $C_{18}H_{24}O_6N_2$: C, 59.37; H,6.59; N, 7.69. Found: C, 59.31; H, 6.66; N, 7.65.

Purity: (HPLC): 97%. After purification by chromatography on a $C_{18}$-reverse phase column the pure dipeptide had m.p. 101°–102° C., $[\alpha]_D^{25} = -32.6°$ (C, 0.9; MeOH), and was identical in all respects (IR, $^{13}C$-NMR) to an authentic sample of N-formyl-($\beta$-methyl)-asp-phe-O-<, m.p. 100°–101° C., $[\alpha]_D^{25°} = -31.3°$ (C, 3.0; MeOH), prepared by the DCC coupling of N-formyl-($\beta$-methyl)-asp-OH and L-phe-O-< in dioxane.

The chemical stability of L-phe-O-< over L-phe-OMe measured seven times higher at 50° C., in water pH 5.0, which is an important advantage for the practice of this invention. Economic benefits deriving from operating at about 50° C., in preference over processing at lower temperatures are: a) the shift of the chemical equilibrium towards peptide formation that occurs with increasing temperature; and b) the increase of peptide permeability across hydrophobic membranes with increasing temperature.

Successful operation of the process of this invention at elevated temperatures depends at least in part on the thermal stability of the lower alkyl ester reactant [B'] and minimizing or avoiding undesirable side reactions, such as hydrolysis of the ester to produce the corresponding acid. It is not possible to efficiently operate the process described in this Example when using L-phenylalanine methyl ester because under the described process conditions at 50° C. that ester is not very stable, i.e., it slowly hydrolizes to L-phenylalanine. The stable isopropyl ester, quickly reacts at 50° C. to provide an effective yield of the desired peptide product and avoids or minimizes undesirable side reactions.

Other L-phenylalanine esters with branched aliphatic alcohols, e.g., 2-butanol and 3-methyl-2-butanol are also expected to have high thermal stability, and to show minimal formation of L-phe-OH by ester hydrolysis in water at pH 5.0 and 50° C.

EXAMPLE 18

Pepsin-catalyzed proteosynthesis of N-CBZ-asp-phe-OMe

To a solution of 85.46 g (320 mmoles) N-CBZ-L-asp-OH and 19.45 g (90 mmoles) L-phe-OMe.HCL in 400 mL water pH 4.0 was added 9.63 g crystalline pepsin (Sigma) dissolved in 100 mL water pH 4.0. The resulting solution (500 mL) was incubated at 38° C. for 48 hrs, at the end of which it was shown by HPLC to contain 3208 mg/L (7.5 mM) of N-CBZ-asp-phe-OMe. The HPLC analyses were done on a Perkin-Elmer System consisting of a 410 LC pump, LC 235 Diode Array detector set at 210 run, and a LCI-100 Laboratory Computing Integrator for data analysis. The analytical column chosen was a NOVA-PAK $C_{18}$ cartridge (8 mm×10 cm, 4$\mu$ bore) housed in a Millipore/Waters RCM-100 radial compression unit. The mobile phase was a v/v mixture of 40% $CH_3CN$ and 60% 0.1% $KH_2PO_4$ buffer containing 0.1% v/v triethylamine, adjusted to pH 4.2. Flow rate was 1 mL/min. Under these conditions, N-CBZ-asp-phe-OMe had a retention time of 7.78 min.

The above reaction mixture (500 mL) was placed in a jacketed vessel kept at 38° C., and it was circulated through the shell side of a hollow fiber separator made of Celgard fibers, containing 1 ft² (900 cm²) ILM of 50% v/v isohexadecanol (Hoechst) in dodecane. The product phase (500 mL) was deionized water pH 7.0, that was circulated countercurrently through the tube side of the module while keeping the pH constant at 7.0 with the assistance of a pH-stat unit, using 0.5N NaOH as titrant.

The synthesis of N-CBZ-asp-phe-OMe in the reaction phase (shell) and the accumulation of the same dipeptide in the product phase (trapped at pH 7.0 as the ionized $\beta$-carboxylate) were measured by HPLC, as described above. After a 5 hr run the circulation of the two phases was interrupted, the product solution was removed and replaced with 500 mL of fresh water pH 7.0 solution. Following a second incubation at 38° C. for 24 hrs, the reaction mixture contained 4170 mg/L of N-CBZ-asp-phe-OMe (HPLC). The countercurrent circulation was reassumed, and the permeation of peptide was monitored for another 5 hr period.

Figure 24:
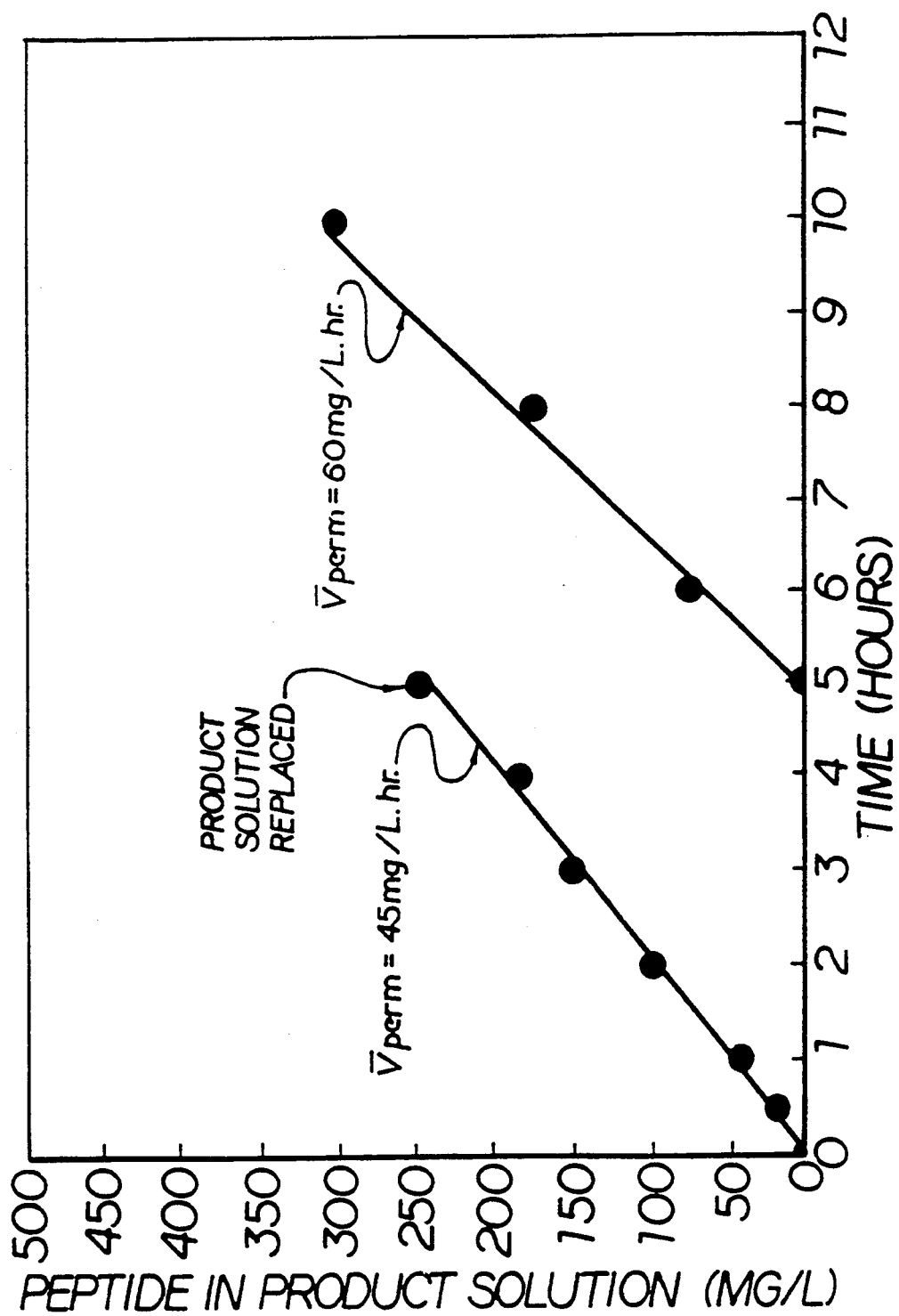
FIG. 24 describes the pepsin-catalyzed proteosynthesis of N-CBZ-asp-phe-OMe in a ILM module.

The results of this experiment are shown in Table XVII and FIG. 24. It is evident from Table XVII that active proteosynthesis has taken place in the enzyme reaction phase, while newly synthesized peptide was being transported across the membrane. Computation of the total N-CBZ-asp-phe-OMe accumulated in the product phases (542 mg in 10 hr) indicates an average permeation rate of 54 mg/L hr, in agreement with the individual $V_{perm}$ rates shown in FIG. 24 for part I and part II.

The isolated peptide product, 220 mg, m.p. 120°–125° C., $[\alpha]_D^{22} = -12.0°$ (c 1.0. MeOH) was identified as N-CBZ-asp-phe-OMe by chromatographic (HPLC, TLC) and $^1H$-NMR comparisons with an authentic sample prepared by the Schotten-Baumann acylation (water, pH 7.5) of aspartame with benzyloxycarbonyl chloride, to yield crystals m.p. 122°–124° C. (from EtOAc/hexane) $[\alpha]_D^{22} = -13.0°$ (c 0.8; MeOH) Literature [D. D. Petkov and I. B. Stoineva, *Tetrahedron Lett* 25, 3754 (1984)] reported m.p. 120°–124° C. $[\alpha]_D^{25} = -14.4°$; (c, 1.0; MeOH).

TABLE XVII

| Time (Hr) | Reaction Phase N—CBZ—asp—phe—OMe (mg/L) | Product Phase N—CBZ—asp—phe—OMe (mg/L) |
|---|---|---|
| PART I | | |
| 0 | 3208.0 | — |
| 1 | 2726.8 | 42.5 |
| 2 | 2887.2 | 99.5 |
| 3 | — | 150.8 |
| 4 | — | 176.4 |
| 5 | 2887.2 | 243.8 |
| PART II | | |
| 0 | 4170.4 | — |
| 1 | — | 75.4 |
| 2 | — | — |
| 3 | — | 170.0 |
| 4 | — | 181.2 |
| 5 | 3528.8 | 298.3 |

While specific embodiments of the invention have been shown and described in detail to illustrate the application of the inventive principles, it will be understood that the invention may be embodied otherwise without departing from such principles.

What is claimed is:

1. A method for the enzymatic synthesis of a peptide, comprising the steps of:

reacting N-acyl-($\beta$-substituted) aspartic acid having an alpha carboxylate group with L-phenylalanine lower alkyl ester having an alpha ammonium group in the presence of thermolysin, in an aqueous reaction phase under conditions in which the alpha carboxylate group and the alpha ammonium group condense forming a protected, uncharged, peptide product;

transporting the protected, uncharged, peptide product across a water-immiscible hydrophobic phase into an aqueous product phase, wherein the water-immiscible hydrophobic phase functions as an ion rejection membrane separating the aqueous reaction phase from the aqueous product phase creating an oil/water interface with each of the aqueous phases, and separating the protected, uncharged, peptide product from the aqueous product phase to prevent that product from back-diffusing across the water-immiscible hydrophobic phase.

2. The method recited in claim 1, wherein the protected, uncharged, peptide product is separated from the aqueous product phase by reverse osmosis.

3. The method recited in claim 1, wherein the aqueous reaction phase is maintained at a temperature in a range of from about 20° C. to about 65° C.

4. The method recited in claim 1, wherein the phenylalanine reactant is a lower alkyl ester derived from secondary alcohol having 3 to 6 carbon atoms.

5. The method recited in claim 4, wherein the temperature of the aqueous reaction phase is about 25° C.

6. The method recited in claim 5, wherein the aspartic acid reactant is N-formyl-($\beta$-methyl)-asp-OH and wherein the phenylalanine reactant is L-phenylalanine isopropyl ester.

7. The method recited in claim 1, wherein the water-immiscible hydrophobic phase is an organic liquid immobilized by capillarity in pores in a microporous support.

8. The method recited in claim 7, wherein the microporous support comprises polypropylene hollow fibers.

9. The method recited in claim 1 wherein the water-immiscible hydrophobic phase comprises an organic liquid located within a lumen defined by the walls of a hollow fiber comprising hydrophilic material.

10. The method recited in claim 9, wherein the hydrophilic material is cellulose.

11. The method recited in claim 9, wherein hollow fibers comprise a membrane module and wherein the water-immiscible hydrophobic phase is located within lumens of the hollow fibers.

12. The method recited in claim 11, further including the steps of providing:

a first membrane module for transferring the protected, uncharged, peptide product from the aqueous phase into the water-immiscible hydrophobic phase;

a second membrane module for transferring the protected, uncharged, peptide product from the water-immiscible hydrophobic phase into the aqueous product phase; and a connecting means between the water-immiscible hydrophobic phase in the first membrane module and the water-immiscible hydrophobic phase in the second membrane module.

13. The method recited in claim 12, wherein the aqueous reaction phase in the first membrane module is located outside of the hollow fibers and wets the walls of the hollow fibers creating an oil/water interface between the aqueous reaction phase and the water-immiscible hydrophobic phase; and wherein the aqueous product phase in the second membrane module is located outside of the hollow fibers and wets the walls of the hollow fibers creating an oil/water interface between the aqueous product phase and the water-immiscible hydrophobic phase.

14. The method recited in claim 12, wherein circulation of aqueous phases at the oil/water interfaces is countercurrent.

15. The method recited in claim 12, further comprising the steps of processing the aqueous product phase through a plurality of membrane contactors.

16. The method recited in claim 6, where in the pH of the reaction mixture is about 5.0.

17. A method for the enzymatic synthesis of a peptide, comprising the steps of:

reacting N-acyl-($\beta$-substituted) aspartic acid having an alpha carboxylate group with L-phenylalanine lower alkyl ester having an alpha ammonium group in the presence of pepsin in an aqueous reaction phase under conditions in which the alpha carboxylate group and the alpha ammonium group condense forming a protected, uncharged, peptide product;

transporting the protected, uncharged, peptide product across a water-immiscible hydrophobic phase, into an aqueous product phase, wherein the water-immiscible hydrophobic phase functions as an ion rejection membrane separating the aqueous reaction phase from the aqueous product phase creating an oil/water interface with each of the aqueous phases, and separating the protected, uncharged, peptide product from the aqueous product phase to prevent that product from back-diffusing across the water-immiscible hydrophobic phase.

18. The method recited in claim 17, wherein the protected, uncharged, peptide is separated from the aqueous product phase by reverse osmosis.

19. The method recited in claim 17, wherein the pH of the aqueous reaction phase is about 4.

20. The method recited in claim 19, wherein the acyl group in the first reactant is carbobenzoxy.

21. The method recited in claim 17, wherein the aqueous reaction phase is maintained at a temperature in a range from about 20° C. to about 65° C.

22. The method recited in claim 17, wherein the phenylalanine reactant is a lower alkyl ester derived from a secondary alcohol having 3 to 6 carbon atoms.

23. The method recited in claim 17, wherein the temperature of the reaction phase is about 25° C.

24. The method recited in claim 17 wherein the water-immiscible hydrophobic phase is an organic liquid immobilized by capillary in pores in a microporous support.

25. The method recited in claim 24, wherein the microporous support comprises polypropylene hollow fibers.

26. The method recited in claim 17, wherein the water-immiscible hydrophobic phase is an organic liquid disposed within a lumen defined by the walls of a hollow fiber comprising hydrophilic material.

27. The method recited in claim 26, wherein the hydrophilic material is cellulose.

28. The method recited in claim 26, wherein hollow fibers comprise a membrane module and wherein the water-immiscible hydrophobic phase is disposed within lumens of the hollow fibers.

29. The method recited in claim 28, further including the steps of providing:
- a first membrane module for transferring the protected, uncharged, peptide product from the aqueous phase into the water-immiscible hydrophobic phase;
- a second membrane module for transferring the protenated, uncharged, peptide product from the water-immiscible hydrophobic phase into the aqueous product phase; and
- a connecting means between the water-immiscible hydrophobic phase in the second membrane module.

30. The method recited in claim 29, wherein the aqueous reaction phase in the first membrane module is disposed outside of the hollow fibers and wets the walls of the hollow fibers creating an oil/water interface between the aqueous reaction phase and the water-immiscible hydrophobic phase; and wherein the aqueous product phase in the second membrane module is disposed outside of the hollow fibers and wets the walls of the hollow fibers creating an oil/water interface between the aqueous product phase and the water-immiscible hydrophobic phase.

31. The method recited in claim 29, wherein the circulation of aqueous phases at the oil/water interfaces is countercurrent.

32. The method recited in claim 29, further comprising the steps of processing the aqueous product phase through a plurality of membrane contactors.

* * * * *

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 10 | 32 | After "limitations" insert --, it--. |
| 12 | 6 | Change "reactants A and B" to --reactants $\underline{A}$ and $\underline{B}$--. |
| 12 | 9 | Change "peptide C" to --peptide $\underline{C}$--. |
| 12 | 16 | Change "C" to --$\underline{C}$--; change "D" to --$\underline{D}$--. |
| 12 | 19 | Change "C." to --$\underline{C}$.--. |
| 12 | 26 | Change "A$^+$" to --$\underline{A}^+$--; change "B$^-$" to --$\underline{B}^-$-- |
| 12 | 30 | Change "C." to --$\underline{C}$.--. |
| 12 | 32 | Change "C." to --$\underline{C}$.--. |
| 12 | 34 | Change "A$^+$" to --$\underline{A}^+$--; change "B$^-$" to --$\underline{B}^-$-- |
| 12 | 35 | Change "C" to --$\underline{C}$--. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 12 | 37 | Change "C" to --$\underline{C}$--. |
| 12 | 41 | Change "C" to --$\underline{C}$--. |
| 12 | 42 | Change "D" to --$\underline{D}$--. |
| 12 | 46 | Change "C" to --$\underline{C}$--; change "D" to --$\underline{D}$--. |
| 12 | 51 | Change "C" to --$\underline{C}$--. |
| 16 | 33 | Change "(C)" to --($\underline{C}$)--. |
| 16 | 34 | Change "A$^+$" to --($\underline{A}^+$--. |
| 16 | 35 | Change "B$^-$" to --$\underline{B}^-$--. |
| 16 | 42 | Change "C" to --$\underline{C}$--. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

Column    Line

16, Table I (last three lines):  Change "N-formyl-isoAPM" to
   --N-formyl-_iso_APM-- (three occurrences).

17, Table I - continued:  Change from                to

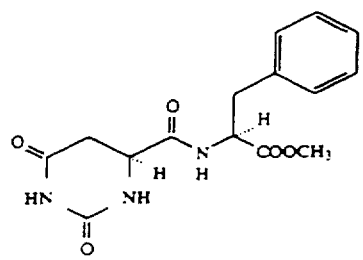 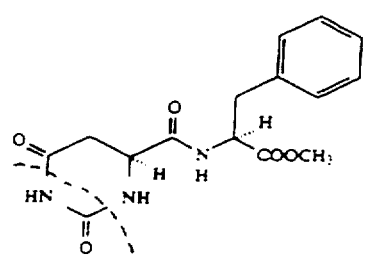

17, Table I - continued (line before last):  Change
   "N-CBZ-isoAPM" to --N-CBZ-_iso_APM--.

17, line 40:  Change "racemate" to --racemic--.

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 19 | 34 | Change "B" to --$\underline{B}$--. |
| 19 | 35 | Change "A" to --$\underline{A}$--. |
| 19 | 37 | Change "A" to --$\underline{A}$--. |
| 19 | 39 | Change "C" to --$\underline{C}$--. |
| 19 | 47 | Change "$\underline{B}$(charged)" to --$\underline{B}$(uncharged)--. |
| 19 | 68 | Change "[3.1.1.1]" to --[EC 3.1.1.1]--. |
| 20 | 64 | Change "sp." to --Sp.--. |
| 21 | 21 | After "50% of a" insert --1%--. |
| 23 | 19 | Change "(N-CBZ-iso-APM)" to --(N-CBZ-$\underline{iso}$-APM)--. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 23 | 20 | Change "EtOH), identical" to --EtOH), identical--. |
| 23 | 21 | Change "N-CBZ-iso-APM" to --N-CBZ-_iso_-APM--. |
| 23 | 36 | Change "N-CBZ-iso-APM" to --N-CBZ-_iso_-APM--. |
| 23 | 38 | Change "N-CBZ-iso-APM" to --N-CBZ-_iso_-APM--. |
| 26 | 4 | Change "Areano" to --Amano--. |
| 26 | 5 | Change "80" to --30--. |
| 26 | 45 | Change "(c2;" to --(c,2;--. |

UNITED STATES PATENT AND TRADEMARK OFFICE
CERTIFICATE OF CORRECTION

PATENT NO. : 5,350,681

DATED : 27 September 1994

INVENTOR(S) : Guillermo A. IACOBOCCI et al.

It is certified that error appears in the above-indentified patent and that said Letters Patent is hereby corrected as shown below:

| Column | Line | |
|---|---|---|
| 26, TABLE VIII, line 4: | | Change "2.46" to --2.66--. |
| 28 | 27 | Change "IT." to --[T.--. |
| 30 | 5 | Change "through out" to --throughout--. |
| 30 | 38 | Change "to time" to --of time--. |
| 30 | 66 | Change "a ice" to --an ice--. |
| 31 | 7 | After "acid," insert -- 5% --. |
| 31 | 10 | After "mg" insert -- (78% --. |
| 31 | 12 | Change "$[\alpha]D^{22}$" to -- $[\alpha]^{22}_D$ -- and align with left margin. |
| 31 | 35 | Align with left margin. |
| 31 | 59 | After "of" insert -- 50% --. |
| 31 | 61 | Before "MeOH" insert -- 10% --. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|--------|------|---|
| 33 | 44 | Change "contained." to --contained--. |
| 33 | 60 | After "containing" insert -- 1% --. |
| 34 | 31 | After "HCl" insert -- in --. |
| 36 | 58 | After "73" insert -- to --. |
| 37 | 67 | Change "...OMe(A)" to --...OMe(A)--. |
| 37 | 68 | Change "asp-OH(B)," to --asp-OH(B),--. |
| 38 | 1 | Change "...OMe(C)" to --...OMe(C)--. |
| 38 | 5 | Change "[B]" to --[B]--; change "[A]" to --[A]--. |
| 38 | 6 | Change "C" to --C--. |
| 38 | 17 | Change "C" to --C--. |
| 38 | 19 | Change "C" to --C--. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 38 | 22 | Change "A" to --$\underline{A}$--; change "B" to --$\underline{B}$--. |
| 38 | 24 | Change "A" to --$\underline{A}$--; change "C" to --$\underline{C}$--. |
| 38 | 25 | Change "(A:C molar" to --($\underline{A}$:$\underline{C}$ molar--. |
| 38 | 28 | Change "A" to --$\underline{A}$--. |
| 38 | 29 | Change "C" to --$\underline{C}$--. |
| 38 | 33 | Change "C" to --$\underline{C}$--. |
| 38 | 35 | Change "A" to --$\underline{A}$--; change "C (A:C molar" to --$\underline{C}$ ($\underline{A}$:$\underline{C}$ molar--. |
| 38 | 37 | Change "C," to --$\underline{C}$,--. |
| 38 | 42 | Change "C" to --$\underline{C}$--. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 40 | 8 | Change "% 0" (two occurrences) to -- $\delta$ --. |
| 40 | 9 | Change "% 0" to -- $\delta$ --. |
| 40 | 11-31 | Delete entirely and insert therefor --47.59, 53.54 ppm (-CH-, d); 52.09, 52.28 ppm ($CH_3$-, q); 127.08, 128.51, 129.19 ppm (phenyl, d); 135.62 ppm (phenyl, s); 160.93 ppm (H-C(=O)-, d); 169.60, 171.34, 172.09 ppm (-C(=O)-O(NH), s). |

UNITED STATES PATENT AND TRADEMARK OFFICE
CERTIFICATE OF CORRECTION

PATENT NO. : 5,350,681

DATED : 27 September 1994

INVENTOR(S) : Guillermo A. IACOBOCCI et al.

It is certified that error appears in the above-indentified patent and that said Letters Patent is hereby corrected as shown below:

| Column | Line | |
|---|---|---|
| 40 | 54-66 | Delete entirely and insert therefor: --(phenyl, s); 163.99 ppm ($H-\underset{\underset{O}{\|}}{C}-$, d); 172.38, 172.83, 174.77 ppm ($-\underset{\underset{O}{\|}}{C}-O(NH)$, s).-- |
| 41 | 10 | After "that is" insert --,--. |
| 42 | 14 | Change "[B']" to --[$\underline{B}$']--. |
| 42 | 19 | Change "(C')" to --($\underline{C}$')--. |
| 42 | 26 | Change "(B')," to --($\underline{B}$'),--. |
| 42 | 27 | Change "(A')" to --($\underline{A}$')--; change "C'" to --$\underline{C}$'--. |

UNITED STATES PATENT AND TRADEMARK OFFICE
CERTIFICATE OF CORRECTION

PATENT NO. : 5,350,681
DATED : 27 September 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 42 | 30 | Change "B'" to --$\underline{B}$'--. |
| 42 | 31 | Change "A'" to --$\underline{A}$'--. |
| 42 | 41 | Change "C'" to --$\underline{C}$'--. |
| 42 | 60 | Change "A'" to --$\underline{A}$'--. |
| 42 | 61 | Change "[A']" to --[$\underline{A}$']--; change "[C']" to --[$\underline{C}$']--. |
| 42 | 67 | Change "C'" to --$\underline{C}$'--; change "A')" to --$\underline{A}$')--. |
| 43 | 27 | Change "[B']" to --[$\underline{B}$']--. |
| 44 | 37 | Change "(c 0.8;" to --(c, 0.8;--. |

UNITED STATES PATENT AND TRADEMARK OFFICE
CERTIFICATE OF CORRECTION

PATENT NO. : 5,350,681
DATED : 27 Spetember 1994
INVENTOR(S) : Guillermo A. IACOBOCCI et al.

It is certified that error appears in the above-indentified patent and that said Letters Patent is hereby corrected as shown below:

| Column | Line | |
|---|---|---|
| 44 | 38 | Change "*Lett*" to --*Lett.*--. |
| 45 | 26 | After "from" insert --a--. |
| 46 | 13 | Change "where in" to --wherein--. |
| 46 | 54 | Change "capillary" to --capillarity--. |

Signed and Sealed this

Seventh Day of January, 1997

Attest:

BRUCE LEHMAN

Attesting Officer

Commissioner of Patents and Trademarks